United States Patent [19]

Singh et al.

[11] Patent Number: 5,342,846
[45] Date of Patent: Aug. 30, 1994

[54] 7-SUBSTITUTED-6-FLUORO-1,4-DIHYDRO-4-OXO-QUINOLINE-3-CARBOXYLIC ACID COMPOUNDS AND 7-(SUBSTITUTED TRIAZOLYL PYRROLIDIN-1-YL) 4-OXOQUINOLINE-3-CARBOXYLIC ACID DERIVATIVES USEFUL AS ANTIBACTERIAL AGENTS

[75] Inventors: Rajeshwar Singh; Rakhshandeh Fathi-Afshar; Inder P. Singh; George Thomas; Thomas R. Doerksen; Maya P. Singh, all of Edmonton; Ronald G. Micetich, Sherwood Park, all of Canada

[73] Assignee: SynPhar Laboratories, Inc., Alberta, Canada

[21] Appl. No.: 913,505

[22] Filed: Jul. 14, 1992

Related U.S. Application Data

[63] Continuation-in-part of Ser. No. 621,716, Dec. 5, 1990, abandoned, Ser. No. 802,665, Dec. 5, 1991, abandoned, and Ser. No. 891,262, Jun. 1, 1992, abandoned, which is a continuation-in-part of Ser. No. 802,665, Jun. 1, 1992, which is a continuation-in-part of Ser. No. 621,716, Jun. 1, 1992.

[51] Int. Cl.⁵ ..................... A61K 31/47; C07D 401/14
[52] U.S. Cl. ........................................ 514/312; 546/156
[58] Field of Search ........................ 546/156; 514/312

[56] References Cited

U.S. PATENT DOCUMENTS

| | | | |
|---|---|---|---|
| 4,556,658 | 12/1985 | Grohe et al. | 514/254 |
| 4,665,079 | 5/1987 | Culbertson et al. | 514/312 |
| 4,855,292 | 8/1989 | Ueda et al. | 514/312 |
| 4,990,517 | 2/1991 | Petersen et al. | 514/300 |
| 4,997,943 | 3/1991 | Iwata et al. | 544/363 |
| 5,059,597 | 10/1991 | Petersen et al. | 514/224.5 |
| 5,104,884 | 4/1992 | Korodi et al. | 514/312 |

FOREIGN PATENT DOCUMENTS

| | | |
|---|---|---|
| 2012223 | 9/1990 | Canada . |
| 0119087 | 9/1984 | European Pat. Off. . |
| 0172651 | 2/1986 | European Pat. Off. . |
| 0203488 | 12/1986 | European Pat. Off. . |
| 0221463 | 5/1987 | European Pat. Off. . |
| 0230295 | 7/1987 | European Pat. Off. . |
| 0287951 | 10/1988 | European Pat. Off. . |
| 0304087 | 2/1989 | European Pat. Off. . |
| 0347851 | 12/1989 | European Pat. Off. . |
| 0350733 | 1/1990 | European Pat. Off. . |
| 0362759 | 4/1990 | European Pat. Off. . |
| 0387802 | 9/1990 | European Pat. Off. . |
| 0388298 | 9/1990 | European Pat. Off. . |
| WO88/02627 | 4/1988 | PCT Int'l Appl. . |
| WO92/10492 | 6/1992 | PCT Int'l Appl. . |

OTHER PUBLICATIONS

Journal of Medicinal Chemistry vol. 35, No. 2, 1992, Washington US pp. 361-367 J. P. Sanchez et al. "New 8-(trifluoromethyl)–substittuted quinolones".
Mitscher et al., "Chiral DNA Gyrase Inhibitors.", Jour. of Med. Chem., vol. 30, No. 12, pp. 2283–2286, 1987.
Chemical Abstracts, vol. 104, p. 712, 1986, abstract No. 104: 109, 495.
Miyamoto et al., "Synthesis and Stucture", J. Med. Chem., vol. 33, No. 6, pp. 1645–1656, 1990.
Hagen et al., "New Quinolone Antibacterial Agents", Jour. of Med. Chem., vol. 33, No. 2, pp. 849–854, 1990.
Chu et al., "Synthesis and Structure", J. Med. Chem., vol. 30, No. 3, pp. 504–509, 1987.
Rosen et al., "Design, Synthesis and Properties", J. Med. Chem., vol. 31, No. 8, pp. 1598–1611, 1988.
Koga et al., "Structure–Activity Relationships", J. Med. Chem., vol. 23, No. 12, pp. 1358–1363, 1980.
Domagala et al., "1–Substituted", J. Med. Chem., vol. 31, No. 5, pp. 991–1000, 1988.
Alpagiani et al., Bioorganic & Medicinal Chemistry Letters, vol. 2, No. 9, pp. 1127–1132, 1992.
Cooper, et al., "Quinlones Containing Novel Substituents at the 7–Position and Theri In Vitro Activity", pp. 1–4 (date not known).

*Primary Examiner*—Patricia L. Morris
*Attorney, Agent, or Firm*—Nikaido Marmelstein Murray & Oram

[57] ABSTRACT

Substituted quinoline compounds and intermediates thereto, processes for producing those compounds and intermediates, pharmaceutical compositions using those compounds, methods for treating bacterial infections using those compounds, and methods for disinfecting using those compounds.

68 Claims, No Drawings

7-SUBSTITUTED-6-FLUORO-1,4-DIHYDRO-4-OXO-QUINOLINE-3-CARBOXYLIC ACID COMPOUNDS AND 7-(SUBSTITUTED TRIAZOLYL PYRROLIDIN-1-YL) 4-OXOQUINOLINE-3-CARBOXYLIC ACID DERIVATIVES USEFUL AS ANTIBACTERIAL AGENTS

This is a continuation-in-part of U.S. patent application Ser. No. 07/621,716, filed Dec. 5, 1990 (now abandoned).

This is also a continuation-in-part of U.S. patent application Ser. No. 07/802,665, filed Dec. 5, 1991 (now abandoned), which in turn is a continuation-in-part of U.S. patent application Ser. No. 07/621,716, filed Dec. 5, 1990.

This is also a continuation-in-part of U.S. patent application Ser. No. 07/891,262, filed Jun. 1, 1992 (now abandoned), which in turn is a continuation-in-part of U.S. patent application Ser. No. 07/802,665, filed Dec. 5, 1991, which in turn is a continuation-in-part of U.S. patent application Ser. No. 07/621,716, filed Dec. 5, 1990.

BACKGROUND OF THE INVENTION

Many clinically important antibacterial agents, collectively known as fluoroquinolones, have been discovered. Quinolones which possess a substituted 1,4-dihydro-4-oxo-quinoline-3-carboxylic acid moiety and which have the general structural formula given below are described in J. Med. Chem. 23, 1358 (1980).

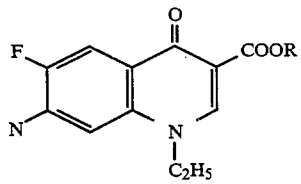

wherein N may be piperazinyl or the like. Belgian Patent 899399 discloses 1-cyclopropyl-7-piperazinyldihydroquinoline carboxylic acid compounds of the formula

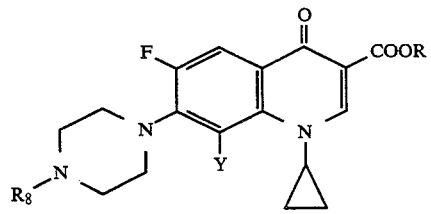

wherein $R_8$ is H or $CH_3$ and Y is Cl, F or $CH_3$.

Japanese Patent No. 174367/1983, South African Patent No. 8502369, European Patent Nos. 172651 and 221463, 119087, U.S. Pat. No. 4,556,658, 1985 and J. Med. Chem. 1990, 33 (1645–1656), disclose compounds represented by the following general formula having an amino group at position 5.

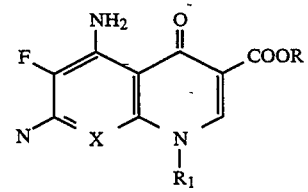

wherein $R_1$ is ethyl, cyclopropyl; X is CH, CF, C—$CH_3$; and N is piperazinyl or the like.

The 7- (3-aminopyrrolidinyl) quinolones which are represented by general formula given below:

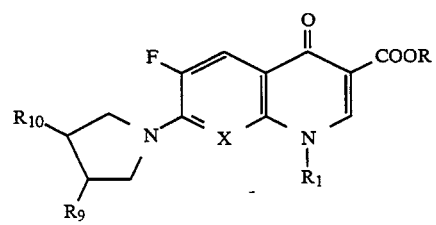

wherein X is N, CH or CF; $R_1$ is ethyl, cyclopropyl, 2,4-difluorophenyl or 4-fluorophenyl; $R_9$ is $NH_2$, $CH_2NH_2$, pyrrole, imidazole or pyrrolidine group and $R_{10}$ is —$OCH_3$, $CH_3$, $C_6H_5$ or =$CH_2$ are disclosed in J. Med. Chem. 1988, 31 (1598–1611); J. Med. Chem. 1990, 33 (849–854); EP 347851, EP 362759, Abstracts of the 30th Interscience Conference on Antimicrobial Agents and Chemotherapy, Atlanta, Oct. 21–24, 1990, Abstract No. 395.

Some of the above disclosed compounds are clinically useful. However, there exists a continuing need to develop new antibacterial agents because the effectiveness of existing antibacterial agents diminish as strains of pathogens develop resistance. In addition, certain antibiotics exhibit unsuitable pharmaceutical properties and exert serious adverse side effects in humans.

SUMMARY OF THE INVENTION

The first aspect of the present invention is based on the discovery that certain 7-substituted-6-fluoro-1,4-dihydro-4-oxoquinoline-3-carboxylic acid compounds exhibit excellent activity against sensitive and resistant Gram-positive and moderate activity against Gram-negative bacteria.

In accordance with the first aspect of the present invention there is provided a 7-substituted-6-fluoro-1,4-dihydro-4-oxo-quinoline-3-carboxylic acid compound of the formula:

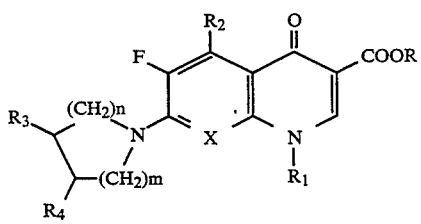

wherein (A) R is hydrogen or $C_1$–$C_4$ alkyl group; $R_1$ is (i) a $C_3$–$C_6$ cycloalkyl group which may be substituted with one or two halogen atoms, or (ii) a phenyl group which may be substituted with one or two halogen atoms, (iii) a $C_1$–$C_4$ alkyl group which may be substituted with one or two halogen atoms; R₂ is hydrogen, a halogen atom, a C₁-C₄ alkyl group, a hydroxy group or an amino group; R₃ is hydrogen, a hydroxy or an amino group; R₄ is a 1,2,3-triazol-1-yl group, a 1,2,4-triazol-1-yl group, a 1,2,3,4-tetrazol-1-yl group or a 1,2,3,4-tetrazol-2-yl group, each of which may have 1 to 2 substituents selected from the group consisting of C₁-C₄ alkyl, COOH, CH₂NH₂, amino and phenyl groups; and X is N, CH, C—F or C—OCH₃; m is 1 or 2; n is 0, 1 or 2; or (B) R, R₂, R₃, R₄, m and n are as defined above and X and R₁ are such that

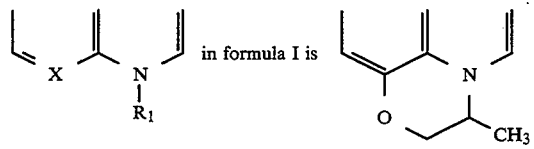

, or a pharmaceutically acceptable salt of any such compound.

Preferably the C₁-C₄ alkyl groups for R, R₁, and R₂ are independently selected from methyl, ethyl, propyl, isopropyl, butyl, isobutyl, and t-butyl; the C₃-C₆ cycloalkyl group is selected from cyclopropyl, cyclobutyl, cyclopentyl and cyclohexyl and the optionally substituted phenyl is selected from phenyl, 4-fluorophenyl and 2,4-difluorophenyl. The groups which may be substituted with one or two halogen atoms, as discussed above, may preferably be substituted with chlorine, bromine or fluorine or a pharmaceutically acceptable salt thereof.

The compounds of the first aspect of the present invention include those wherein the azetidine, pyrrolidine or piperidine moiety at the 7-position has an asymmetric carbon atom or atoms and can be in optically active forms. Hence, this invention includes the R isomer, the S isomer and mixtures thereof. Some of the compounds of this invention have two asymmetric carbon atoms on the azetidine, pyrrolidine or piperidine moiety and therefore exist as stereoisomers having different configurations (i.e., cis- and trans-configurations). Such stereoisomers and their mixtures are also included within this invention.

The compounds of the first aspect of this invention exhibit excellent antimicrobial activity against both sensitive and resistant Gram-positive bacteria. Compounds of formula I may be utilized as antibacterial active compounds in medicaments formulated with pharmaceutically acceptable carriers.

The second aspect of the present invention is based on the discovery that certain 7-substituted-6-fluoro-1,4-dihydro-4-oxo-quinoline-3-carboxylic acid compounds exhibit excellent activity against sensitive and resistant Gram-positive and moderate activity against Gram-negative bacteria. In accordance with the second aspect of the present invention, there is provided a 7-substituted-6-fluoro-1,4-dihydro-4-oxo-quinoline-3-carboxylic acid compound of the general formula A1:

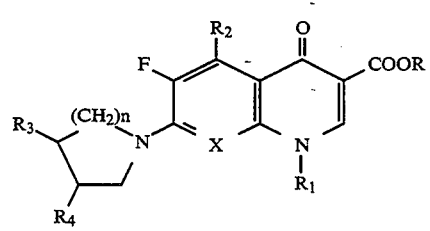

wherein

R is hydrogen or a C₁-C₄ alkyl group;

R₁ is an optionally substituted C₁-C₄ alkyl group, an optionally substituted C₃-C₆ cycloalkyl group or an optionally substituted phenyl group;

R₂ is hydrogen, a halogen, a C₁-C₄ alkyl group, NR⁵R⁶, OH, OC₁-C₄ alkyl or O₂C-phenyl group;

R₃ is hydrogen, C₁-C₄ alkyl, C₃-C₆ cycloalkyl, halo, COOR, CH₂COOR, NR⁵R⁶, CH₂NR⁵R⁶, OH, OC₁-C₄ alkyl, COCH₃ or phenyl;

n=0, 1 or 2;

X is N, C—F, CH, C—CH₃, C—CF₃ or C—OCH₃;

wherein R₄ is

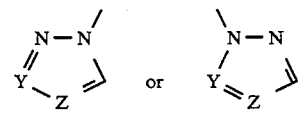

Y and Z are N or CH, provided that at least one of Y and Z is N, preferably forming a 1,2,3-triazol-1-yl a 1,2,4-triazol-1-yl, a 1,2,3,4-tetrazol-1-yl or a 1,2,3,4-tetrazol-2-yl ring, optionally substituted by halogen, C₁-C₄ alkyl, C₃-C₆ cycloalkyl, COCH₃, COOR, CH₂COOR, CSC₁-C₄ alkyl, NR⁵R⁶, CH₂NR⁵R⁶ or phenyl; and R⁵ and R⁶ are hydrogen, a C₁-C₄ alkyl group, or a C₃-C₆ cycloalkyl group;

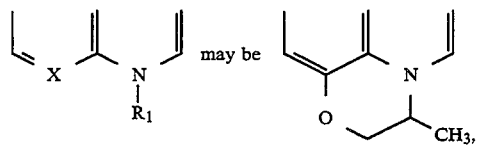

or a pharmaceutically acceptable salt thereof.

Preferably the C₁-C₄ alkyl group is selected from methyl, ethyl, propyl, isopropyl, butyl, isobutyl or t-butyl; the C₃-C₆ cycloalkyl group is selected from cyclopropyl, cyclobutyl, cyclopentyl or cyclohexyl and the optionally substituted phenyl is selected from phenyl, 4-fluorophenyl or 2,4-difluorophenyl. The groups which may be substituted, as discussed above, may be substituted with chlorine, bromine, fluorine or a methoxy group.

In accordance with a preferred embodiment of the second aspect of the present invention there is provided a 7-substituted-6-fluoro-1,4-dihydro-4-oxo-quinoline-3-carboxylic acid compound of the formula:

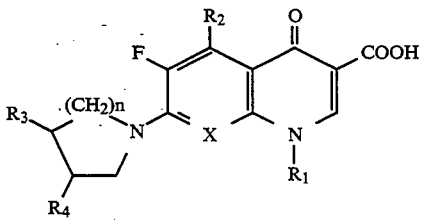

wherein
$R_1$ is a $C_3$–$C_6$ cycloalkyl group of a phenyl group which may be substituted by a halogen atom;
$R_2$ is hydrogen a halogen atom a $C_1$–$C_4$ alkyl group, a hydroxy group or an amino group;
$R_3$ is hydrogen, hydroxy or amino;
$R_4$ is a 1,2,3-triazol-1-yl group or 1,2,4-triazol-1-yl group each of which may have 1 to 2 substituents selected from the group consisting of $C_1$–$C_4$ alkyl, —COOH, —$CH_2NH_2$, amino and phenyl group; and
X is N, CH, C—F or C—$OCH_3$;
n is 0, 1 or 2; or

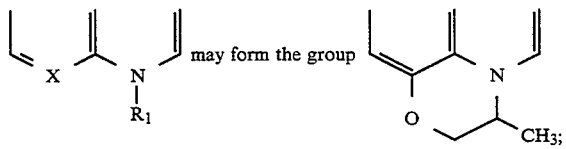

or a pharmaceutically acceptable salt thereof.

The compounds of the second aspect of the present invention include those wherein the azetidine, pyrrolidine or piperidine moiety at the 7-position has an asymmetric carbon atom or atoms and can exist in optically active forms. Hence, this aspect of the invention includes the R isomer, the S isomer and mixtures thereof. Some of the compounds of this invention have two asymmetric carbon atoms on the azetidine, pyrrolidine or piperidine moiety and therefore exist as stereoisomers having different configurations (i.e., cis- and transconfigurations). Such stereoisomers and their mixtures are also included within the compounds of this invention.

More specifically, the most preferred embodiments of the second aspect of the present invention include the following compounds:

6,8-Difluoro-1-(4-fluorophenyl)-7-[3-(1,2,3-triazol-1-yl)pyrrolidin -1-yl]-1,4-dihydro-4-oxo-quinoline-3-carboxylic acid;

1-(2,4-Difluorophenyl )-6-fluoro-7-[3-(1,2,3-triazol-1-yl) -pyrrolidin-1-yl]-1,4-dihydro-4-oxo-1,8-naphthyridin-3-carboxylic acid;

1-Cyclopropyl-6-fluoro-7-[3-( 1,2,3-triazol-1-yl) -pyrrolidin-1-yl]-1,4-dihydro-4-oxo-quinoline-3-carboxylic acid;

1-Cyclopropyl-6,8-difluoro-7-[3-(1,2,3-triazol-1-yl)pyrrolidin-1-yl]-1,4-dihydro-4-oxo-quinoline-3-carboxylic acid;

5-Amino-1-cyclopropyl-6,8-difluoro-7-[3-( 1,2,3-triazol-1-yl) -pyrrolidin-1-yl]-1,4-dihydro-4-oxo-quinoline-3-carboxylic acid;

5-Amino-1-cyclopropyl-6,8-difluoro-7-[3S-( 1,2,3-triazol-1-yl) -pyrrolidin- 1-yl]-1,4-dihydro-4-oxo-quinoline-3-carboxylic acid;

5-Amino-1-cyclopropyl-6,8-difluoro-7-[3R-( 1,2,3-triazol-1-yl) -pyrrolidin-1-yl]-1,4-dihydro-4-oxoquinoline-3-carboxylic acid;

5-Amino-1-(2,4-difluorophenyl)-6,8-difluoro-7-[3-( 1,2,3-triazol-1-yl )-pyrrolidin-1-yl]-1,4-dihydro-4-oxoquinoline -3-carboxylic acid;

5-Amino-1-(2,4-difluorophenyl )-6,8-difluoro-7-[3 S-(1,2,3-triazol -1-yl )-pyrrolidin-1-yl]-1,4-dihydro-4-oxoquinoline -3-carboxylic acid;

5-Amino-1-(2,4-difluorophenyl )-6,8-difluoro-7-[3R -(1,2,3-triazol-1-yl)-pyrrolidin-1-yl]-1,4-dihydro-4-oxoquinoline -3-carboxylic acid;

7-[cis-3-Amino-4-(1,2,3-triazol-1-yl)-pyrrolidin-1-yl]-1-cyclopropyl-6,8-difluoro-1,4-dihydro-4-oxo-quinoline-3-carboxylic acid;

5-Amino-7-[cis-3-amino-4-(1,2,3-triazol-1-yl)-pyrrolidin -1-yl]-1-cyclopropyl-6,8-difluoro-1,4-dihydro-4-oxoquinoline -3-carboxylic acid;

5-Amino-7-[cis-3-amino-4-(1,2,3-triazol-1-yl)-pyrrolidin -1-yl]-1-(2,4-difluorophenyl)-6,8-difluoro-1,4-dihydro-4-oxo-quinoline-3-carboxylic acid;

5-Amino-7-[trans-3-hydroxy-4-(1,2,3-triazol-1-yl)pyrrolidin -1-yl]-1-cyclopropyl-6,8-difluoro-1,4-dihydro-4-oxo-quinoline-3-carboxylic acid.

The compounds of the second aspect of this invention exhibit excellent antimicrobial activity against both ,sensitive and resistant Gram-positive bacteria especially when the $R_1$ substituent is cyclopropyl, $R_2$ is amino and $R_3$, $R_4$ and $R_5$ are hydrogen. Compounds of formula A1 may be utilized as antibacterial active compounds in medicaments formulated with pharmaceutically acceptable carriers.

The third aspect of the present invention is based on the discovery that certain 7-(substituted triazolylpyrrolidin-1-yl)-1,4-dihydro-4-oxo-quinoline-3-carboxylic acid derivatives exhibit excellent activity against sensitive and resistant Gram-positive and moderate activity against Gram-negative bacteria.

In accordance with the third aspect of the present invention, there is provided a 7-(substituted triazolyl pyrrolidin-1-yl)-4-oxo-quinoline-3-carboxylic acid derivative of general formula B1:

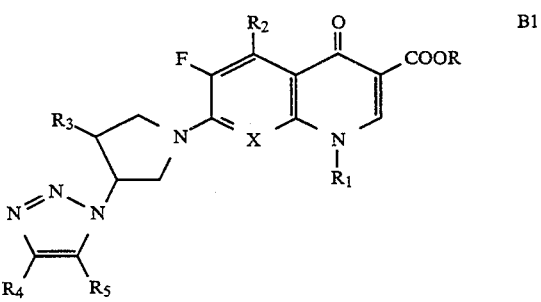

wherein
R is hydrogen or $C_1$–$C_4$ alkyl group or a pharmaceutically acceptable salt, such as from a metal ion or an amine;
$R_1$ is an optionally substituted $C_1$–$C_4$ alkyl group or an optionally substituted $C_3$–$C_6$ alicyclic hydrocarbon group or an optionally substituted or unsubstituted phenyl group;
$R_2$ is hydrogen or halogen or $C_1$–$C_4$ alkyl group or $NHR_6$;
$R_3$ is hydrogen, $OR_6$, F, $CH_3$ or $NHR_6$;

$R_4$ and $R_5$ are independently hydrogen or $NHR_6$ or $CH_2NHR_6$ or $COOR_6$ or $CH_2OR_6$ or $CH_3$ or ethyl;

$R_6$ is hydrogen, $C_1$–$C_4$ alkyl group or $C_3$–$C_6$ cycloalkyl group or acetyl group; and X is nitrogen or C—F or CH or C—$CH_3$ or C—$CF_3$ or C—$OCH_3$.

Preferably a $C_1$–$C_4$ alkyl group is selected from methyl, ethyl, propyl, isopropyl, butyl, isobutyl or t-butyl; a $C_3$–$C_6$ alicyclic hydrocarbon group is selected from cyclopropyl, cyclobutyl, cyclopentyl or cyclohexyl and the substituted or unsubstituted phenyl is selected from phenyl, 4-fluorophenyl or 2,4-difluorophenyl. The groups which may be substituted, as discussed above, may be substituted with chlorine, bromine, fluorine or a methoxy group.

In accordance with a second embodiment of the third aspect of the present invention there is provided a 7-(substituted triazolyl pyrrolidin-1-yl)-4-oxo-quinoline -3-carboxylic acid derivative of the general formula I wherein:

R is hydrogen or a pharmaceutically acceptable base salt, such as a metal ion or an amine;

$R_1$ is ethyl, cyclopropyl, 4-fluorophenyl or 2,4-difluorophenyl;

$R_2$ is hydrogen, F or $NH_2$;

$R_3$ is hydrogen, $NH_2$ or OH;

$R_4$ and $R_5$ are hydrogen;

X is nitrogen, or C—F or CH or C—$CH_3$ or C—$CF_3$ or C—$OCH_3$.

The compounds of the invention include those which have asymmetric carbon atoms on the pyrrolidine ring at the 7-position and therefore exist in optically active form. Hence this invention includes the D isomer, the L isomer and mixtures thereof. Some of the compounds of this invention have two asymmetric carbon atoms on the pyrrolidine ring at the 7-position and therefore exist as stereoisomers having different configurations (i.e., cis and trans configurations). Therefore, stereoisomers and their mixtures are also included within the compounds of this invention.

DESCRIPTION OF THE PREFERRED EMBODIMENTS

In general, the 7-substituted-6-fluoro-1,4-dihydro-4-oxo-quinoline-3-carboxylic acid compounds of formula I are prepared as follows:

Compounds having the general formula II are reacted with compounds having the general formula III under the conditions described hereinafter.

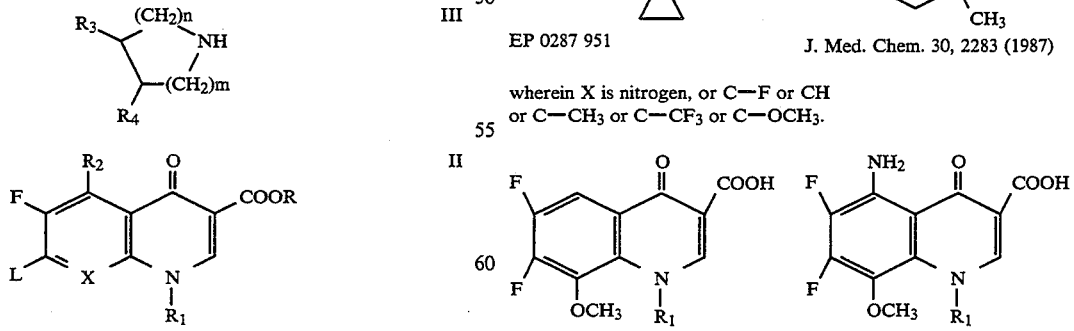

L is a suitable leaving group, such as chlorine, bromine, fluorine, $SO_2R_{11}$, wherein $R_{11}$ is a $C_1$–$C_4$ alkyl group or an unsubstituted or substituted phenyl group. The starting compounds having the formula II can be prepared from known starting materials using standard procedures or variations thereof within the skill of the art. Various starting compounds of formula II are known and are shown below in association with a reference citation:

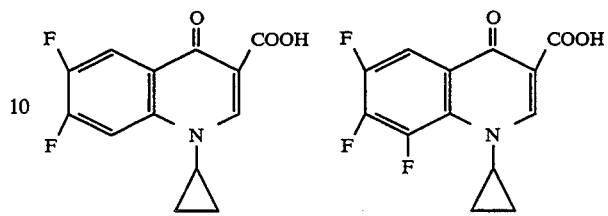

J. Med. Chem. 31, 983 (1988)

U.S. Pat. No. 4,665,079
J. Med. Chem. 31, 991 (1988)

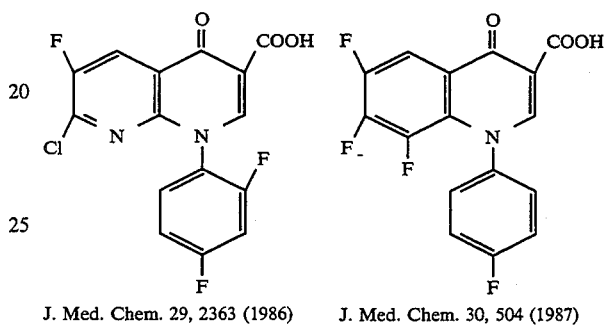

J. Med. Chem. 29, 2363 (1986)

J. Med. Chem. 30, 504 (1987)

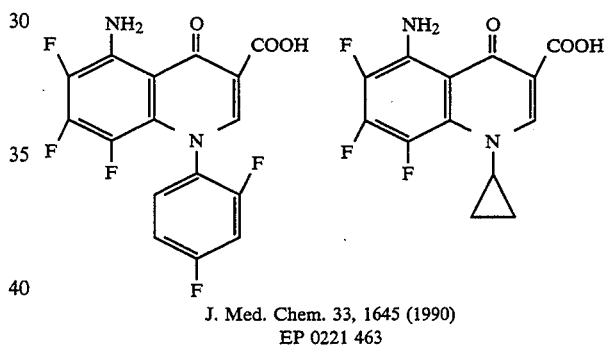

J. Med. Chem. 33, 1645 (1990)
EP 0221 463

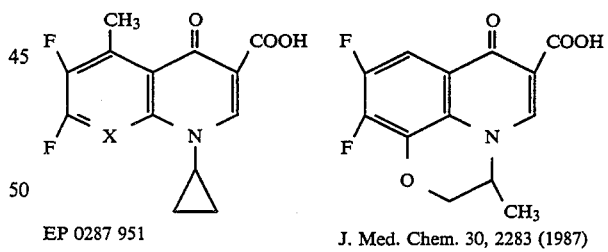

EP 0287 951

J. Med. Chem. 30, 2283 (1987)

wherein X is nitrogen, or C—F or CH or C—$CH_3$ or C—$CF_3$ or C—$OCH_3$.

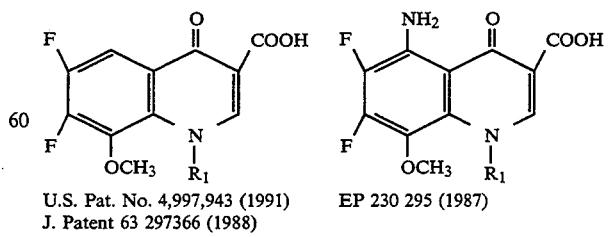

U.S. Pat. No. 4,997,943 (1991)
J. Patent 63 297366 (1988)

EP 230 295 (1987)

A schematic route for the preparation of compounds of formula III wherein the azole ring is a 1,2,3-triazol-1-yl is given below:

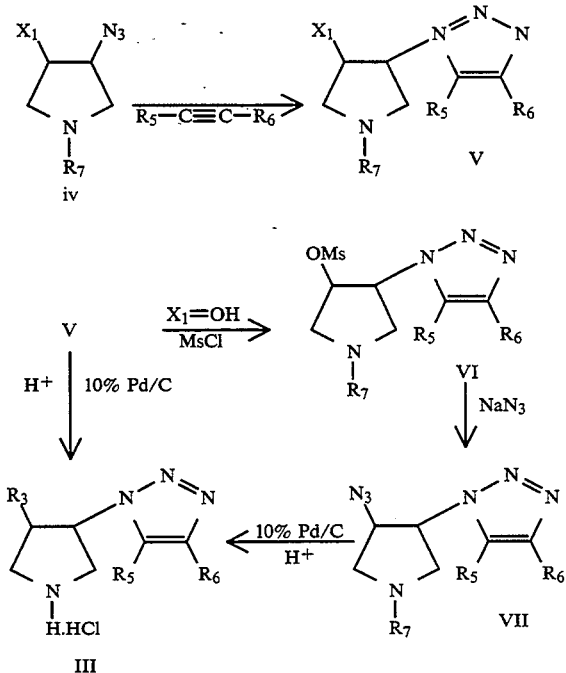

wherein X₁ is hydrogen or hydroxy; $R_3$ is hydrogen or a hydroxy group or an amino group; $R_5$ and $R_6$ are hydrogen, $C_1$–$C_4$ alkyl, COOH, $CH_3NH_2$, amino or phenyl; $R_7$ is benzyl or t-BOC protective group.

The reaction of compound IV and a substituted acetylene as shown is carried out in a suitable solvent such as acetone, methanol, ethanol, benzene, toluene or xylene, either in a high pressure vessel or at normal pressure. The reaction is usually carried out at a temperature from room temperature to 150° C., preferably from 60° C. to 140° C., for 2 to 96 hours. Substituted acetylenes are usually used in an amount of at least 1 mole, preferably 1 to 15 moles, for every one mole of compound IV.

Deprotection of the N-protective group of compound V is carried out either by hydrogenation in presence of an acid such as hydrochloric acid, acetic acid, etc. or by hydrolysis with mineral acid such as HCl, $HNO_3$, $H_2SO_4$, $CF_3COOH$ or $CH_3COOH$ in a solvent such as methanol, ethanol or propanol. The deprotection reaction is usually carried out at a temperature from 0° C. to 100° C., usually at 0° C. to 40° C., for 10 minutes to 48 hours. The hydrogenation reaction is usually carried out in the presence of metal catalyst such as Pd, Pt or Rh on charcoal under normal pressure to high pressure.

The reaction of compound V and methyl sulfonyl chloride (MSCl) is carried out in a suitable solvent, for example, dichloromethane, chloroform, carbon tetrachloride, benzene, toluene, DMF or DMSO in the presence of a base such as triethylamine, $NaHCO_3$, $K_2CO_3$, $CsCO_3$, sodium alkoxide ($NaOCH_3$ or $NaOC_2H_5$), potassium tertbutoxide or pyridine. The reaction temperature is in the range from 0° C. to 100° C., preferably 0° C. to 35° C., and reaction times vary from 1 hour to 48 hours. The methylsulfonyl chloride is usually used in an amount of at least 1 mole preferably 1 to 5 moles per mole of compound V.

The reaction of compound VI and a metal azide such as $NaN_3$ in the presence of phase transfer catalyst such as $NH_4Cl$, $(NH_4)_2CO_3$, $(Bu)_4NBr$ is carried out in a polar solvent such as DMF or DMSO, etc. or in a mixture of solvents such as $DMF-H_2O$, $DMSO-H_2O$ in a ratio of 4:1. The reaction temperature ranges from room temperature to 180° C., preferably from 40° C. to 100° C. The reaction time ranges from 1 hour to 48 hours, and a molar ratio of from 1 to 5 moles of metal azide per mole of compound VI is preferred. The phase transfer catalysts are used in same ratio as the metal azide ratio.

The reaction condition for conversion of compound VII to compound III is the same as described for conversion of compound V to compound III.

Compounds of the formula III wherein the azole ring is a 1,2,4-triazol-1-yl can be prepared by the reaction of potassium-1,2,4-triazolide with N-benzhydryl -3[(methylsulphonyl)oxy]azetidine or N-benzyl-3-[(methylsulphonyl) -oxy]pyrrolidine. The N-blocking groups are then removed in the usual manner by catalytic hydrogenation with palladium on charcoal, as illustrated in Examples U, V, W and X.

Compounds of the formula III wherein the azole ring is a 1,2,3,4-tetrazol-1-yl or 1,2,3,4-tetrazol-2-yl moiety are prepared in an analogous manner as illustrated in Examples JJ, KK and LL.

Compounds of the formula III wherein n=0 (azetidines) or n=2 (piperidines) are prepared in analogous manner to those wherein n=1 (pyrrolidines).

The starting compounds of II and III are reacted together in the presence of solvents at elevated or reduced temperatures for a sufficient time to allow the reaction to proceed to completion. Reaction conditions will depend upon the nature of the leaving group L of the compounds of formula II and the degree of reactivity of compound III.

The reaction is preferably carried out in the presence of a proton acceptor such as pyridine, diazabicycloundecane (DBU), N-methylpyrrolidine-2-one or picoline.

The solvents of choice for this reaction are nonreactive solvents such as acetonitrile, tetrahydrofuran (THF), ethanol, methanol, chloroform, methylene chloride, pyridine, picoline, N-methylpyrrolidine-2-one, water, dimethyl sulfoxide, dimethylformamide or the like. Mixtures of these solvents may also be utilized.

Reaction temperatures will generally range from between about 50° C. to 150° C. The preferred molar ratio of compounds II and III are 1:2.5 to 5.0. The reaction times generally range from 4 to 96 hours depending on the reactants.

Another method for preparing compounds of formula I is by reacting a compound of general formula II with a compound of formula VIII to form a compound of formula IX followed by substitution of leaving group $L_1$ in IX with the appropriately substituted azoles as shown below.

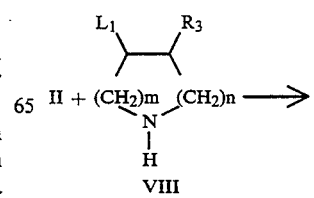

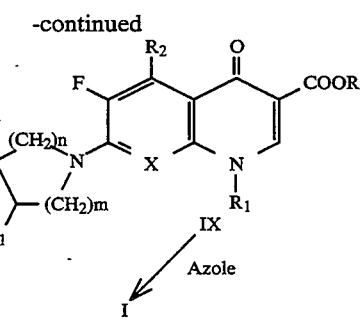

R, $R_1$, $R_2$, $R_3$, X and L are the same as defined above. $L_1$ is the suitable leaving group selected from chlorine, bromine, fluorine or $OSO_2CH_3$ or $OSO_2C_6H_4CH_3(p)$.

An alternate process can also be used for preparing the compound of formula I by reacting the compound of formula II with compound of formula XI followed by reaction with substituted acetylenes as shown in the following schemes:

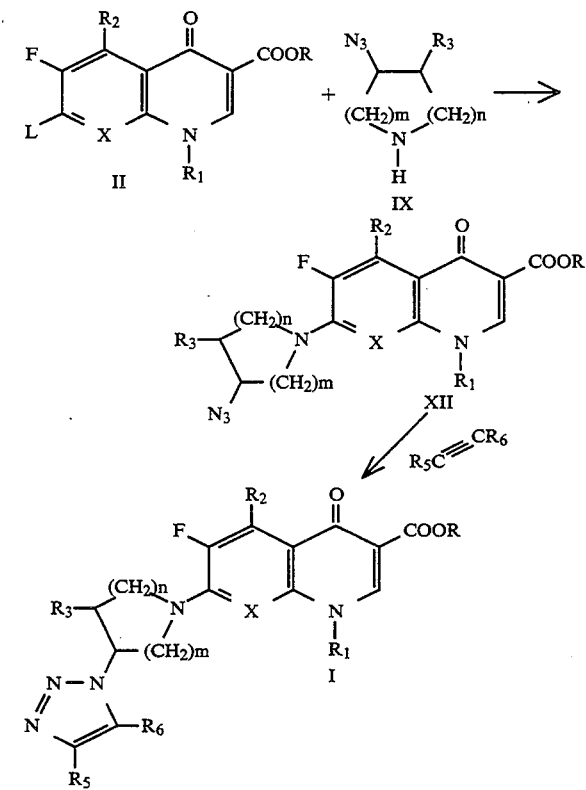

R, $R_1$, $R_2$, $R_3$, $R_5$, $R_6$, X and L are the same as defined above. The reaction time, temperature, molar ratio and solvent for the reaction of the compound of formula II with the compound of formula VIII or reaction of compound of formula II with compound of formula XI are the same as defined for the reaction of compound II with compound III, as described above.

The reaction temperature, time, molar ratio and solvent used for the reaction of compound IX with triazoles are the same as described above for the reaction of compound VI with metal azides ($NAN_3$) or $(C_4H_9)_4NN_3$. The reaction temperature, times, molar ratio and solvent used for the reaction of compound XII with substituted acetylenes are the same as described for the conversion of compound IV to compound V.

The compounds of the first aspect of the present invention are capable of forming both pharmaceutically acceptable acid addition and/or base salts. Base salts are formed with alkali and alkaline earth metals such as sodium, potassium, magnesium, calcium, and the like, and heavy metal salts such as silver, zinc, cobalt, and cerium, and with organic amines such as choline and lysine, either directly or in combination with a physiologically acceptable carrier.

Pharmaceutically acceptable acid addition salts are formed with organic and inorganic acids such as hydrochloric, sulfuric, phosphoric, acetic, citric, oxalic, malonic, salicylic, malic, gluconic, fumaric, succinic, ascorbic, maleic, methanesulfonic, p-toluenesulfonic acid and the like. The salts are prepared by contacting the free base form with a sufficient amount of the desired acid or amine to produce, for example, the mono or di salt in a conventional manner.

The compounds of the first aspect of the present invention can exist in unsolvated as well as solvated forms including hydrated forms and the like. In general, the solvated forms, including hydrated forms, are equivalent to the unsolvated forms for the purpose of the invention.

The compounds of formula I are useful as antibacterial agents. They were found to be very potent in vitro against various sensitive and quinolone resistant Gram positive microbes such as E. faecium, S. aureus Cogve, S. epidermis, S. saprophyticus, and S. pyogenes. Further studies on some of the compounds of this invention revealed that their in vitro MIC values against Gram-positive and Gram-negative organisms are negligibly affected by inoculum size, cations ($Mg^{++}$, $Ca^{++}$), and serum.

Human patients suffering from bacterial infections can be treated by administering to the patient a pharmaceutically effective amount of one or more of the present compounds optionally, but preferably, in the presence of a pharmaceutically acceptable carrier or diluent. There may also be included a pharmaceutically compatible binding agent, and/or adjuvant materials. The active materials can be mixed with other active materials which do not impair the desired action and/or supplement the desired action. The above materials according to the present invention can be administered by any route, for example, orally, parenterally, intravenously, intradermally, subcutaneously or topically in solid or liquid form.

The solid form preparation includes powders, tablets, dispensable granules, capsules, cachets, suppositories and ointments. A solid carrier can be one or more substances which may also act as diluents, flavoring agents, solubilizers, lubricants, suspending agents, binders, or tablet disintegrating agents, including magnesium carbonate, magnesium stearate, talc, sugar, lactose, pectin, dextrin, starch, gelatin, gum tragacanth, methyl cellulose, sodium carboxymethyl cellulose, low melting wax, cocoa butter and the like.

Liquid form preparations include solutions, suspensions and emulsions. The liquid preparation for parenteral injection may be water or water-propylene glycol solution or the like, so long as it is acceptable to biological systems (isotonicity, pH, etc.). Aqueous solutions suitable for oral use can be prepared by dissolving the active component in water and adding suitable colorant, flavors, stabilizing and thickening agents as desired. Aqueous suspensions suitable for oral use can be made by dispersing the finely divided active component in water with viscous material, i.e. natural or synthetic gum, resins, methyl cellulose, sodium carboxymethyl cellulose and other well known suspending agents.

The quantities of active compound in a unit dose of a preparation may be varied depending on the particular application and the potency of the active ingredient. Determination of the proper dosage for a particular situation is within the skill of the art. The dosage of the pharmaceutical preparation is generally in the range of 0.2 to 100 mg of the compound of formula I and salts thereof per kilogram of body weight of the patient per day. Preferably this daily dose is administered 2–4 times per day in fractions of the daily dose.

In general, the 7-substituted-6-fluoro-1,4-dihydro-4-oxo-quinoline-3-carboxylic acid compounds of formula A1 are prepared as follows:

Compounds having the general formula A2 are reacted with compounds having the general formula A3 under the conditions described hereinafter.

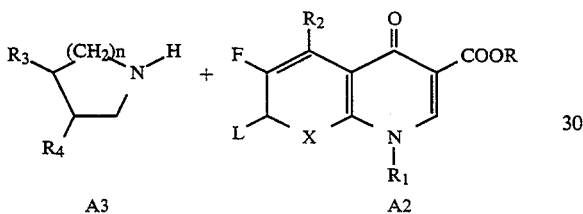

L is a suitable leaving group and may be chlorine, bromine, fluorine, $SO_2R_{11}$, wherein $R_{11}$ is a $C_1$–$C_4$ alkyl group or an unsubstituted or substituted phenyl group. The starting compounds having the formula A2 can be prepared from known starting materials using standard procedures or variations thereof within the skill of the art. Various starting compounds of formula A2 are known and are shown below in association with a reference citation:

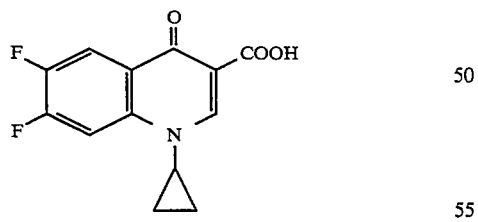

J. Med. Chem. 31, 903 (1988)

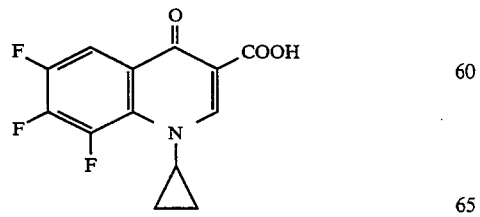

U.S. Pat. No. 4,665,079
J. Med. Chem. 31, 99 (1988)

-continued-

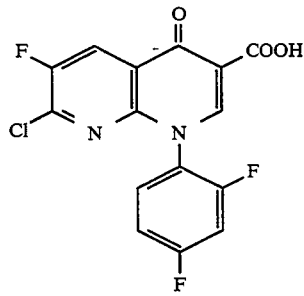

J. Med. Chem. 29, 2363 (1986)

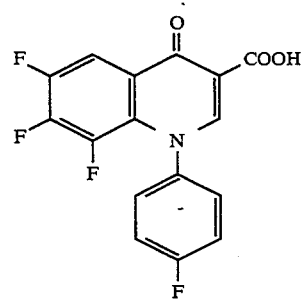

J. Med. Chem. 30, 504 (1987)

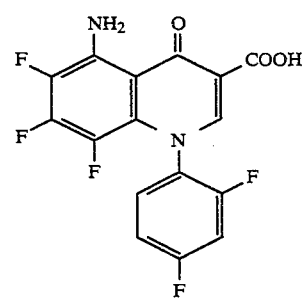

J. Med. Chem. 33, 1645 (1990)
EP 0221 463

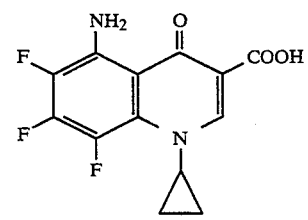

J. Med. Chem. 33, 1645 (1990)
EP 0221 463

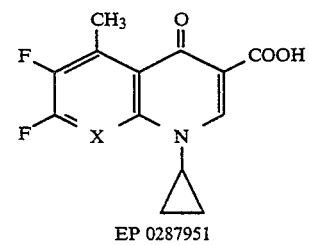

EP 0287951 wherein X is nitrogen, or C—F or CH or C—$CH_3$ or C—$CF_3$ or C—$OCH_3$.

A schematic route for the preparation of compounds of formula A3 wherein the azole ring is a 1,2,3-triazole is given below:

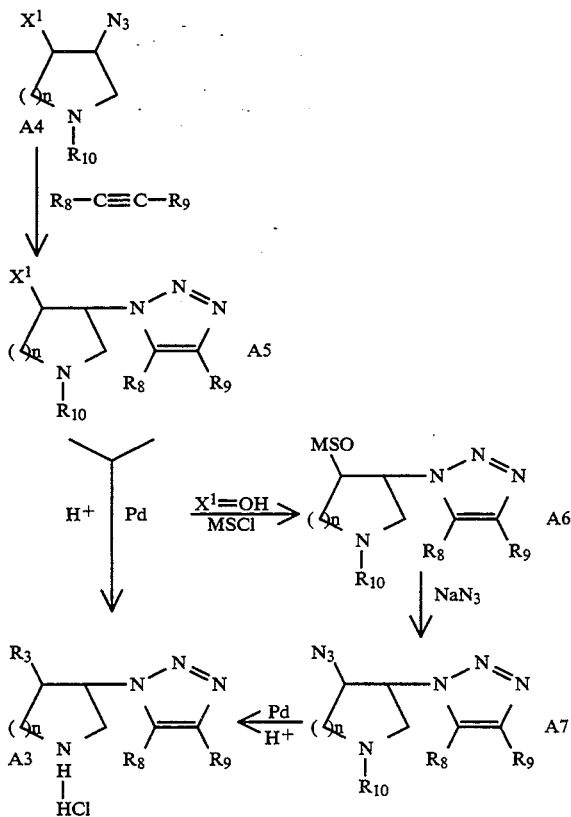

wherein $X^1$ is hydrogen or hydroxy,
$R_3$ is hydrogen or hydroxy or amino group,
$R_8$ and $R_9$ are hydrogen, $C_1$-$C_4$ alkyl, COOH, $CH_2NH_2$,
$NH_2$ or phenyl,
$R_{10}$ is benzyl or t-BOC protective group,
n=0, 1 or 2.

The reaction of compound A4 and a substituted acetylene as shown is carried out in a suitable solvent such as acetone, methanol, ethanol, benzene, toluene or xylene, either in a high pressure vessel or at normal pressure. The reaction is usually carried out at temperature from room temperature to 150° C., preferably from 60° C. to 140° C., for 2 to 96 hours. Substituted acetylenes are usually used in an amount of at least 1 mole, preferably 1 to 15 moles, for every one mole of compound A4.

Deprotection of the N-protective group of compound v is carried out either by hydrogenation in presence of an acid such as hydrochloric acid, acetic acid etc. or by hydrolysis with mineral acid such as HCl, $HNO_3$, $H_2SO_4$, $CF_3COOH$ or $CH_3COOH$ in a solvent such as methanol, ethanol or propanol. The deprotection reaction is usually carried out at a temperature from 0° C. to 100° C., usually at 0° C. to 40° C., for 10 minutes to 48 hours. The hydrogenation reaction is usually carried out in presence of metal catalyst such as Pd, Pt or Rh under normal pressure to high pressure.

The reaction of compound A5 and methane sulfonyl chloride (MSCl) is carried out in a suitable solvent, for example, dichloromethane, chloroform, carbon tetrachloride, benzene, toluene, DMF or DMSO in the presence of a base such as triethylamine, $NaHCO_3$, $K_2CO_3$, $CsCO_3$, sodium alkoxide ($NaOCH_3$ or $NaOC_2H_5$), potassium tert-butoxide or pyridine. The reaction temperature is in the range from 0° C. to 100° C., preferably 0° C. to 35° C., and reaction times vary from 1 hour to 48 hours. The methanesulfonyl chloride is usually used in an amount of at least 1 mole, preferably 1 to 5 moles per mole of compound A5.

The reaction of compound A6 and a metal azide such as $NaN_3$ in the presence of phase transfer catalyst such as $NH_4Cl$, $(NH_4)_2CO_3$, $(Bu)_4NBr$ is carried out in a polar solvent such as DMF or DMSO, etc. or in a mixture of solvents such as $DMF-H_2O$, $DMSO-H_2O$ in a ratio of 4:1. The reaction temperature ranges from room temperature to 180° C., preferably from 40° C. to 100° C. The reaction time ranges from 1 hour to 48 hours, and a molar ratio of from 1 to 5 moles of metal azide per mole of compound A6 is preferred. The phase transfer catalysts are used in same ratio as the metal azide ratio.

The reaction condition for conversion of compound A7 to compound A3 is the same as described for conversion of compound A5 to compound A3.

Compounds of the formula A3 wherein the azole ring is a 1,2,4-triazole can be prepared by the reaction of potassium-1,2,4-triazolide with N-benzhydryl-3-mesyloxyazetidine or N-benzyl-3-mesyloxypyrrolidine. The N-blocking groups are then removed are in the usual manner by catalytic hydrogenation with palladium on charcoal, as illustrated in Examples U, V, W and X.

Compounds of the formula A3 wherein the azole ring is a 1,2,3,4-tetrazole moiety are prepared in an analogous manner as illustrated in Examples JJ, KK and LL.

Compounds of the formula A3 wherein n=0 (azetidines) or n=2 (piperidines) are prepared in analogous manner to those wherein n=1 (pyrrolidines).

The starting compounds A2 and A3 are reacted together in the presence of solvents at elevated or reduced temperatures for a sufficient time to allow the reaction to proceed to completion. Reaction conditions will depend upon the nature of the leaving group L of the compounds of formula A2 and the degree of the reactivity of compound A3.

The reaction is preferably carried out in the presence of a proton acceptor such as pyridine, diazabicycloundecane (DBU), N-methyl pyrrolidine-2-one or picoline.

The solvents of choice for this reaction are nonreactive solvents such as acetonitrile, tetrahydrofuran (THF), ethanol, methanol, chloroform, methylene chloride, pyridine, picoline, N-methylpyrrolidine-2-one, water, dimethyl sulfoxide, dimethylformamide or the like. Mixtures of these solvents may also be utilized.

Reaction temperatures will generally range from between about 50° C. to 150° C. The preferred molar ratio of compounds A2 and A3 are 1:2.5 to 5.0. The reaction times generally range from 4 to 50 hours depending on the reactants.

Another method for preparing compounds of formula A1 is by reacting a compound of the general formula A2 with a compound of formula A8 to form a compound of formula A9 followed by substitution of leaving group $L_1$ in A9 with the appropriately substituted azoles as shown below.

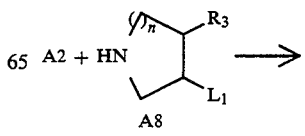

-continued

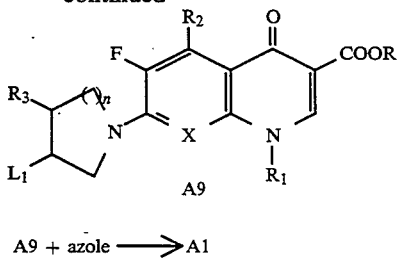

A9 + azole ⟶ A1

R, $R_1$, $R_2$, $R_3$, X, n and L are the same as defined above. $L_1$ is the suitable leaving group selected from chlorine, bromine, fluorine or $SO_2CH_3$ or $SO_2$ $C_6H_4$ $CH_3(p)$.

An alternate process can also be used for preparing the compound of formula A1 by reacting the compound of formula A2 with compound of formula A9 followed by reaction with substituted acetylenes as shown in the following scheme:

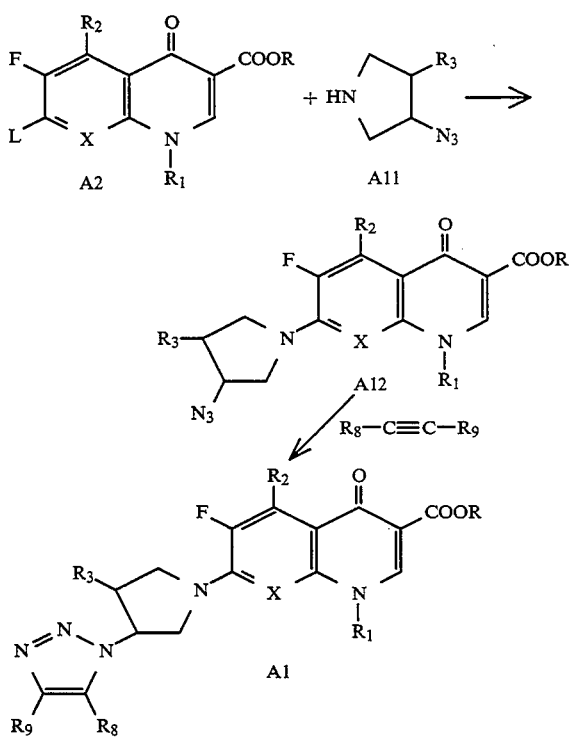

R, $R_1$, $R_2$, $R_3$, $R_8$, $R_9$, n, X and L are the same as defined above. The reaction time, temperature, molar ratio and solvent for the reaction of the compound of formula A2 with the compound of formula A8 or reaction of compound of formula A2 with compound of formula A11 are the same as defined for the reaction of compound A2 with compound A3, as described above.

The reaction temperature, time, molar ratio and solvent used for the reaction of compound A9 with triazoles are the same as described above for the reaction of compound A6 with metal azides ($NAN_3$) or $(C_4H_9)_4NN_3$. The reaction temperature, times, molar ratio and solvent used for the reaction of compound A12 with substituted acetylenes are the same as described for the conversion of compound A4 to compound A5.

The pyrido-benzoxazine compounds of the invention are prepared as illustrated in Examples 41, 42 and 43 using the procedure described by Mitschef et al J. Med. Chem. 30, 2283-2286 (1987) to prepare the pyridobenzoxazine intermediate compounds of formula A2.

The compounds of the second aspect of the present invention are capable of forming both pharmaceutically acceptable acid addition and/or base salts. Base salts are formed with alkali and alkaline earth metals such as sodium, potassium, magnesium, calcium, and the like, and heavy metal salts such as silver, zinc, cobalt, and cerium, and with organic amine salts such as choline, lysine and ethanolamine, either directly or in combination with a physiologically acceptable carrier.

Pharmaceutically acceptable acid addition salts are formed with organic and inorganic acids such as hydrochloric, sulfuric, phosphoric, acetic, citric, oxalic, malonic, salicylic, malic, gluconic, fumaric, succinic, ascorbic, maleic, methanesulfonic, p-toluenesulfonic acid and the like. The salts are prepared by contacting the free base form with a sufficient amount of the desired acid or amine to produce, for example, the mono or di salt in a conventional manner.

The compounds of the second aspect of the present invention can exist in unsolvated as well as solvated forms including hydrated forms and the like. In general, the solvated forms, including hydrated forms, are equivalent to the unsolvated forms for purpose of the invention.

The compounds of formula A1 are useful as antibacterial agents. They were found to be very potent in vitro against various sensitive and quinoline resistant Gram positive microbes such as *E. faecium*, *S. aureus* Cog.-ve, *S. epidermidis*, *S. saprophyticus*, and *S. pyogenes*. Further studies on some of the compounds of this invention revealed that their in vitro MIC values against Gram-positive and Gram-negative organisms are negligibly affected by inoculum size, cations ($Mg^{++}$, $Ca^{++}$), and serum.

Human patients suffering from bacterial infections can be treated by administering to the patient a pharmaceutically effective amount of one or more of the present compounds optionally, but preferably, in the presence of a pharmaceutically acceptable carrier or diluent. There may also be included a pharmaceutically compatible binding agent, and/or adjuvant materials. The active materials can also be mixed with other active materials which do not impair the desired action and/or supplement the desired action. The above materials according to the present invention can be administered by any route, for example, orally, parenterally, intravenously, intradermally, subcutaneously or topically in solid or liquid form.

The solid form preparation includes powders, tablet, dispensable granules, capsules, cachets, suppositories and ointments. A solid carrier can be one or more substances which may also act as diluents, flavoring agents, solubilizers, lubricants, suspending agents, binders, or tablet disintegrating agents, including magnesium carbonate, magnesium stearate, talc, sugar, lactose, pectin, dextrin, starch, gelatin, gum tragacanth, methyl cellulose, sodium carboxymethyl cellulose, low melting wax, cocoa butter and the like.

Liquid form preparations include solutions, suspensions and emulsions. The liquid preparation for parenteral injection may be water or water-propylene glycol solution or water-polyethylene glycol solution or the like, so long as it is acceptable to biological systems (isotonicity, pH etc.). Aqueous solutions suitable for oral use can be prepared by dissolving the active component in water and adding suitable colorant, flavors, stabilizing and thickening agents as desired. Aqueous suspensions suitable for oral use can be made by dispersing the finely divided active component in water with viscous material, i.e. natural or synthetic gum, resins, methyl cellulose, sodium carboxymethyl cellulose and other well known suspending agents.

The quantities of active compound in a unit dose of a preparation may be varied depending on the particular application and the potency of the active ingredient. Determination of the proper dosage for a particular situation is within the skill of the art. The dosage of the pharmaceutical preparation is generally in the range of 0.2 to 100 mg of the compound of formula I and salts thereof per kilogram of body weight of the patient per day. Preferably this daily dose is administered 2–4 times per day in fractions of the daily dose.

In general, the 7-(substituted triazolyl pyrrolidin-1-yl)-4-oxo-quinoline-3-carboxylic acid derivatives having the formula B1:

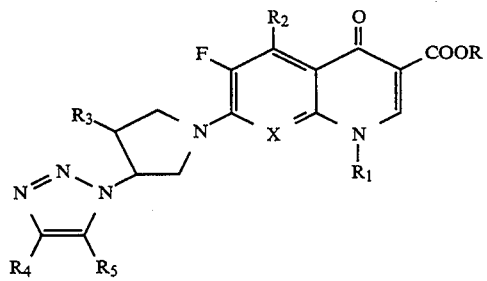

are prepared as follows:

Compounds having the general formula B2 are reacted with compounds having the general formula B3 under the conditions described hereinafter.

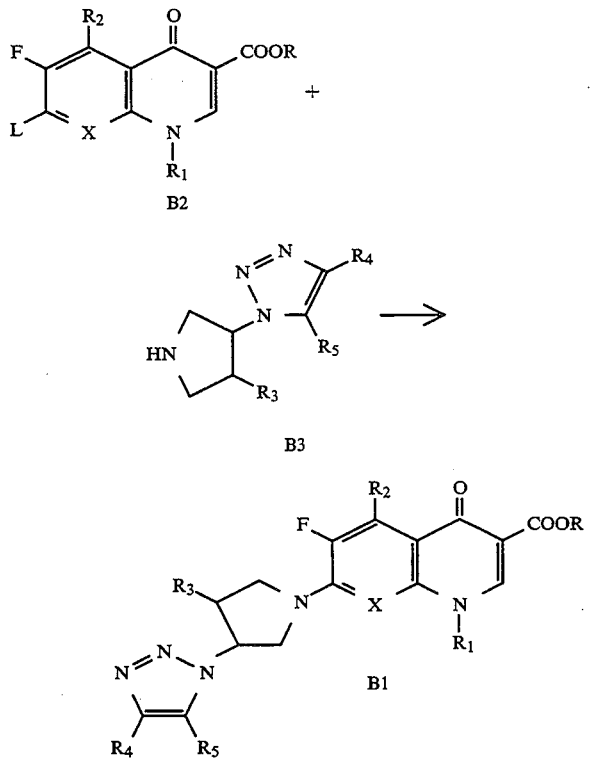

L is a suitable leaving group and may be chlorine, bromine, fluorine, $SO_2R_{11}$, wherein $R_{11}$ is a $C_1$–$C_4$ alkyl group or an unsubstituted or substituted phenyl group. The starting compounds having the formula B2 can be prepared from known starting materials using standard procedures or variations thereof within the skill of the art. Various starting compounds of formula B2 are known and are shown below in association with a reference citation:

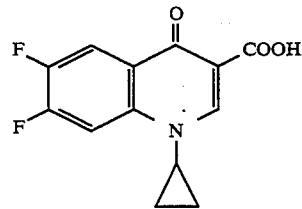

J. Med. Chem. 31, 903 (1988)

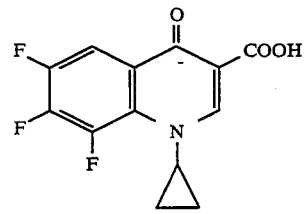

U.S. Pat. No. 4,665,079
J. Med. Chem. 31, 99 (1988)

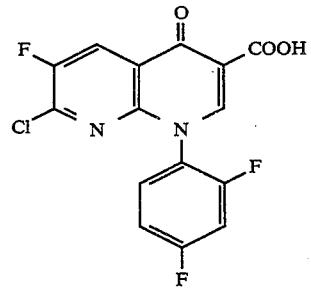

J. Med. Chem. 29, 2363 (1986)

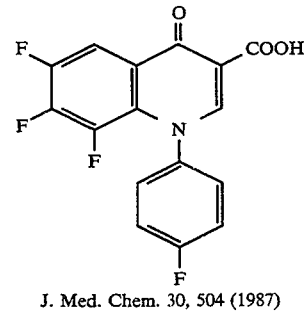

J. Med. Chem. 30, 504 (1987)

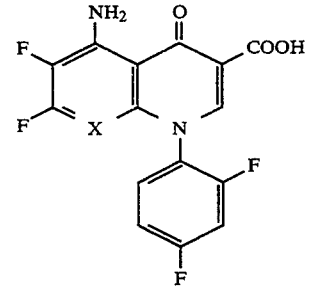

J. Med. Chem. 33, 1645 (1990)
EP 0221 463

-continued

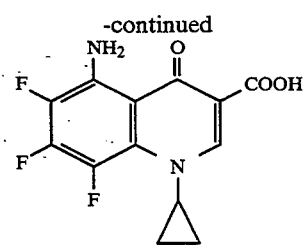

J. Med. Chem. 33, 1645 (1990)
EP 0221 463

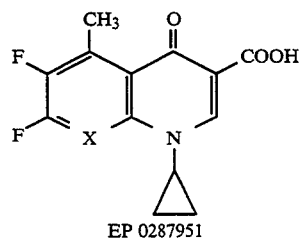

EP 0287951 wherein X is nitrogen, or C—F or CH or C—CH$_3$ or C—CF$_3$ or C—OCH$_3$.

The starting compounds having formula B3 are not commercially available and can be prepared from known starting materials under the conditions described hereinafter. The schematic route for the preparation of compounds of formula B3 is given below:

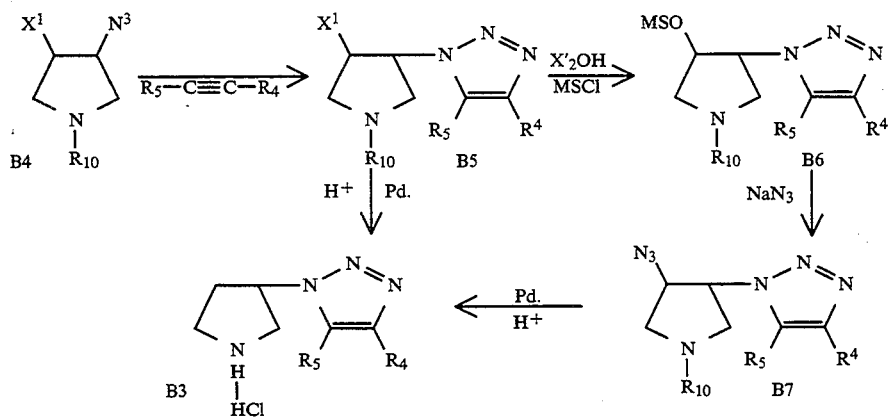

wherein;

X$^1$ is hydrogen or hydroxy,

R$_3$ is hydrogen or hydroxy or amino group,

R$_4$ and R$_5$ are hydrogen,

R$_{10}$ is benzyl or t-BOC protective group.

The reaction of compound B4 and a substituted acetylene as shown is carried out in a suitable solvent such as acetone, methanol, ethanol, benzene, toluene or xylene, either in a high pressure vessel or at normal pressure. The reaction is usually carried out at temperature from room temperature to 150° C., preferably from 60° C. to 140° C., for 2 to 96 hours. Substituted acetylenes are usually used in an amount of at least 1 mole, preferably 1 to 15 moles, for every one mole of compound B4.

The deprotection of the N-protective group of compound B5 is carried out either by hydrogenation in presence of an acid such as hydrochloric acid, acetic acid etc. or by hydrolysis with mineral acid such as HCl, HNO$_3$, H$_2$SO$_4$, CF$_3$COOH or CH$_3$COOH in a solvent such as methanol, ethanol or propanol. The deprotection reaction is usually carried out at a temperature from 0° C. to 100° C., usually at 0° C. to 40° C., for 10 minutes to 48 hours. The hydrogenation reaction is usually carried out in presence of metal catalyst such as Pd, Pt or Rh under normal pressure to high pressure.

The reaction of compound B5 and methane sulfonyl chloride (MSCl) is carried in a suitable solvent, for example, dichloromethane, chloroform, carbon tetrachloride, benzene, toluene, DMF or DMSO in the presence of a base such as triethylamine, NaHCO$_3$, K$_2$CO$_3$, CsCO$_3$, sodium alkoxide (NaOCH$_3$ or NaOC$_2$H$_5$), potassium tert-butoxide or pyridine. The reaction temperature is in the range from 0° C. to 100° C., preferably 0° C. to 35° C., and reaction times vary from 1 hour to 48 hours. The methanesulfonyl chloride is usually used in an amount of at least 1 mole preferably 1 to 5 moles per mole of compound B5.

The reaction of compound B6 and a metal azide such as NaN$_3$ in the presence of phase transfer catalyst such as NH$_4$Cl, (NH$_4$)$_2$CO$_3$, (Bu)$_4$NBr is carried out in a polar solvent such as DMF or DMSO, etc. or in a mixture of solvents such as DMF-H$_2$O, DMSO-H$_2$O in a ratio of 4:1. The reaction temperature ranges from room temperature to 180° C., preferably from 40° C. to 100° C. The reaction time ranges from 1 hour to 48 hours, and a molar ratio of from 1 to 5 moles of metal azide per mole of compound B6 is preferred. The phase transfer catalysts are used in same ratio as the metal azide ratio.

The reaction condition for conversion of compound B7 to compound B3 is the same as described for conversion of compound B5 to compound B3.

The starting compounds B2 and B3 are reacted together in the presence of solvents at elevated or reduced temperatures for a sufficient time to allow the reaction to proceed to completion. Reaction conditions will depend upon the nature of the leaving group L of the compounds of formula B2 and the degree of the reactivity of compound B3.

The reaction is preferably carried out in the presence of a proton acceptor such as pyridine, diazabicycloundecane (DBU), N-methyl pyrrolidine-2-one or picoline.

The solvents of choice for this reaction are nonreactive solvents such as acetonitrile, tetrahydrofuran (THF), ethanol, methanol, chloroform, methylene chloride, pyridine, picoline, N-methylpyrrolidine-2-one, water, dimethyl sulfoxide, dimethylformamide or the like. Mixtures of these solvents may also be utilized.

Reaction temperatures will generally range from between about 50° C. to 150° C. The preferred molar ratio of compounds B2 and B3 are 1:2.5 to 5.0. The reaction times generally range from 4 to 50 hours depending on the reactants.

Another method for preparing 7-(substituted triazo-lylpyrrolidin-1-yl)-1,4-dihydro-4-oxo-quinoline-3-carboxylic acid derivatives of the general formula B1 can be accomplished by reacting a compound of the general formula B2 with compound of formula B8 followed by substitution of leaving group L₁ with substituted triazoles as shown below.

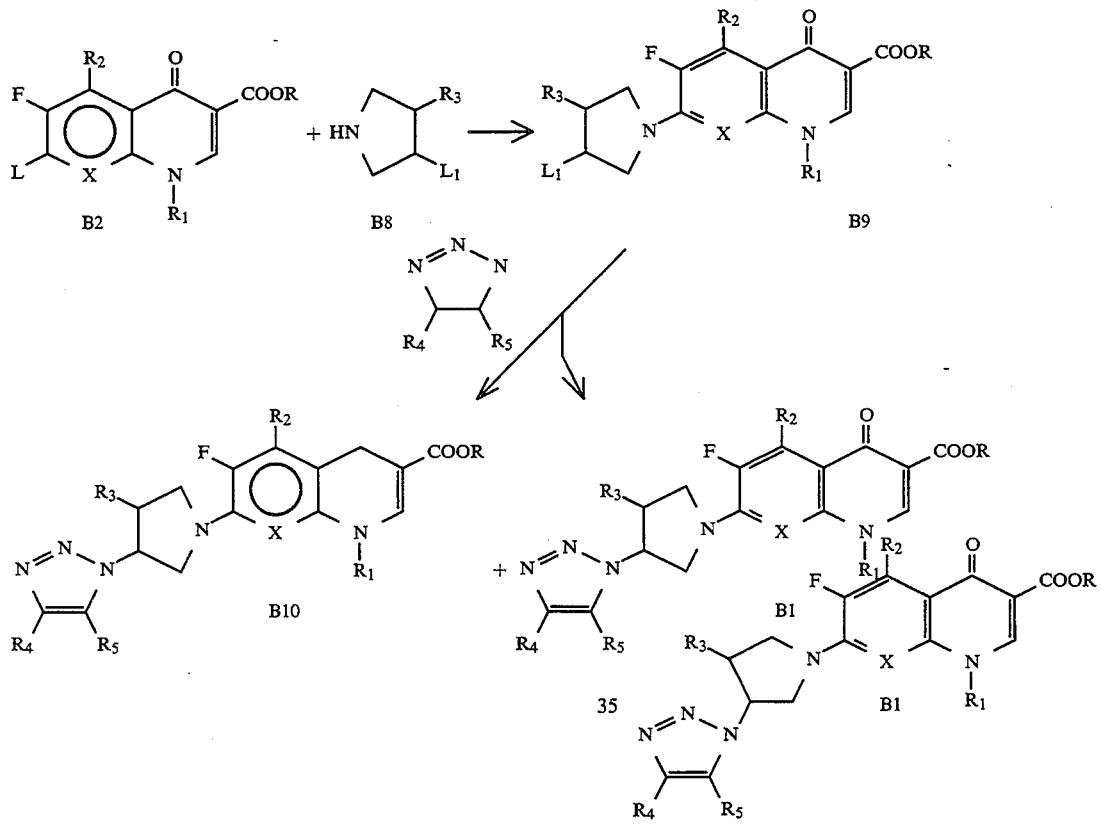

R, R₁, R₂, R₃, R₄, R₅ and L are the same as defined above. L₁ is the suitable leaving group selected from chlorine, bromine, fluorine or SO₂CH₃ or SO₂ C₆H₄ CH₃(p).

An alternate process can also be used for preparing the compound of formula B1 by reacting the compound of formula B2 with compound of formula B11 followed by reaction with substituted acetylenes as shown in the following scheme:

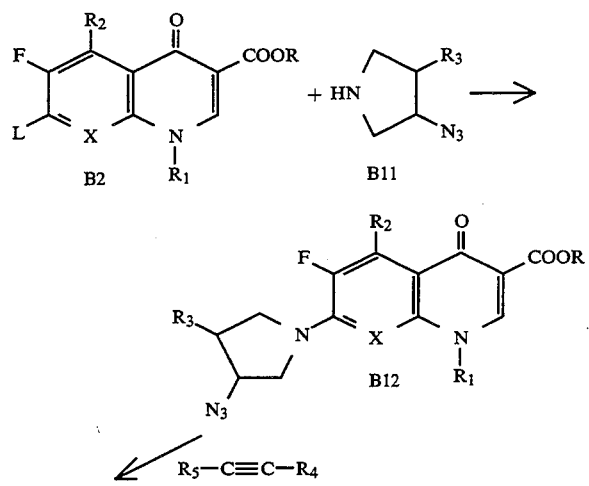

R, R₁, R₂, R₃, R₄, R₅ and L are same as defined above.

The reaction time, temperature, molar ratio and solvent for the reaction of the compound of formula B2 with the compound of formula B8 or reaction of compound of formula B2 with compound of formula B11 are the same as defined for the reaction of compound B2 with compound B3, as described above.

The reaction temperature, time, molar ratio and solvent used for the reaction of compound B9 with triazoles are the same as described above for the reaction of compound B6 with metal azides (NAN₃) or (C₄H₉)₄NN₃. The reaction temperature, times, molar ratio and solvent used for the reaction of compound B12 with substituted acetylenes are the same as described for the conversion of compound B4 to compound B5.

The structures of the compounds of the invention were established by the modes of synthesis and by extensive high field nuclear magnetic resonance spectral techniques.

The compounds of formula B1 display antimicrobial activities against various pathogenic microorganisms and may be useful for the treatment of diseases caused by such microorganisms in humans and other mammals.

The active compounds or the pharmaceutical preparations can be administered locally, orally, parenterally, intraperitoneally and/or rectally, preferably orally or parenterally as well as intravenously or intramuscularly.

Our invention is further illustrated by means of the following non-limiting examples:

EXAMPLE 1

Ethyl 6,8-difluoro-1-(4-fluorophenyl)-7-[3-(1,2,3-triazol-1-yl)pyrrolidin-1-yl]-1,4-dihydro-4-oxo-quinoline-3-carboxylate A solution of ethyl 1-(4-fluorophenyl)-6,7,8-trifluoro-1,4-dihydro-4-oxo-quinoline-3-carboxylate (180 mg, 0.5 mmol), 3-(1,2,3-triazol-1-yl)-pyrrolidine hydrochloride (259 mg, 1.4 mmol) and DBU (384 mg, 2.5 mmol) in acetonitrile (20 ml) was heated at 75° C for 3 h, cooled to r.t. and stirred for another 15 h. The separated solid was filtered, successively washed with acetonitrile and ether. The white crystalline solid thus obtained was dried in vac-oven at 40° C. Yield: 135 mg, 56.7%. $^1$H NMR (CDCl$_3$) δ: 1.35 (t, 3H), 2.50 (m, 2H), 3.70 (m, 1H), 3.85 (m, 2H), 4.10 (m, 1H), 4.35 (q, 2H), 5.25 (m, 1H), 7.20 (m, 2H), 7.40 (m, 2H), 7.63 (d, 1H), 7.72 (d, 1H), 7.90 (dd, 1H), 8.25 (s, 1H).

EXAMPLE 2

6,8-Difluoro-1-(4-fluorophenyl)-7-[3-(1,2,3-triazol-1-yl)pyrrolidin-1-yl]-1,4-dihydro-4-oxo-quinoline-3-carboxylic acid A suspension of ethyl 6,8-difluoro-1-(4-fluorophenyl)-7-[3-(1,2,3-triazol-1-yl)-pyrrolidin-1-yl]-1,4-dihydro-4-oxo-quinoline-3-carboxylate (180 mg, 0.37 mmol) in 20 ml NaOH solution (containing 15 mg NaOH) and THF (20 ml) was heated at 90° C. for 3.5 h. The THF was evaporated and the separated solid was redissolved in water layer by heating and acidified to pH 6.0. The precipitate was filtered, washed with water and dried in vac-oven at 40° C., gave the title compound as a light yellow solid. Yield: 89 mg, 52.7%; m.p. 303° C. $^1$H NMR (TFA) δ: 2.82 (m, 2H), 4.14–4.64 (m, 4H), 5.74 (m, 1H), 7.37 (m, 2H), 7.60 (m, 2H), 8.20 (dd, 1H), 8.54 (d, 1H), 8.65 (d, 1H), 9.03 (s, 1H).

EXAMPLE 3

Ethyl 1-(2,4-difluorophenyl)-6-fluoro-7-[3-(1,2,3-triazol-1-yl)-pyrrolidin-1-yl]-1,4-dihydro-4-oxo-1,8-naphthyridine-3-carboxylate A mixture of ethyl 1-(2,4-difluorophenyl)-7-chloro-6-fluoro-1,4-dihydro-4-oxo-1,8-naphthyridine-3-carboxylate (91 mg, 0.5 mmol), 3-(1,2,3-triazol-1-yl)pyrrolidine hydrochloride (259 mg, 1.5 mmol), and DBU (380 mg, 2.5 mmol) in CH$_3$CN (20 ml) was heated under reflux for 2 h, cooled to r.t. and stirred further for 18 h, diluted with water. Unreacted starting materials were removed by extraction with chloroform. The water layer was concentrated to give a yellow oil. Yield: 150 mg, 62%. $^1$H NMR (CDCl$_3$) δ: 1.3 (t, 3H), 2.5 (m, 2H), 3.9 (m, 4H), 4.4 (q, 2H), 5.3 (m, 1H), 7.3 (m, 4H), 7.8 (d, 1H), 8.0 (d, 1H), 8.4 (s, 1H).

EXAMPLE 4

Ethyl 1-cyclopropyl-6-fluoro-7-[3(S)-(1,2,3-triazol-1-yl)pyrrolidin-1-yl]-1,4-dihydro-4-oxo-1,8naphthyridine-3-carboxylate Ethyl 7-chloro-1-cyclopropyl-6-fluoro-1,4-dihydro-4-oxo-1,8-naphthyridine-3-carboxylate (250 mg, 0.8 mmol) was reacted with 350 mg (2 mmol) of 3(S)-(1,2,3-triazol-1-yl)pyrrolidine hydrochloride in 8 ml of pyridine in the presence of 305 mg (2 mmol) of DBU at 80°–90° C. for 6 h. The reaction was then stirred at r.t. for 4 days. The solvent was then evaporated under reduced pressure and to the residue, water was added and extracted with chloroform. The organic layer was dried and evaporated to dryness. The residue was then chromatographed over alumina (neutral, activity III) using chloroform as solvent to yield 80 mg (24%) of the desired product. $^1$H NMR (CDCl$_3$) δ: 8.48 (s, 1H), 8.05 (d, 1H), 7.76 (d, 1H), 7.71 (d, 1H), 5.46–5.32 (m, 1H), 4.46–4.26 (m, 4H), 4.15–4.0 (m, 2H), 3.56–3.42 (m, 1H), 2.71–2.57 (m, 2H), 1.4 (t, 3H), 1.26–0.95 (m, 4H).

EXAMPLE 5

1-Cyclopropyl-6-fluoro-7-[3(S)-(1,2,3-triazol-1-yl)pyrrolidin-1-yl[1,4-dihydro-4-oxo-1,8-naphthyridine-3-carboxylic acid Ethyl 1-cyclopropyl-6-fluoro-7-[3(S)-(1,2,3-triazol-1-yl)pyrrolidin-1-yl]-1,4-dihydro-4-oxo-1,8-naphthyridine-3-carboxylate (80 mg, 0.19 mmol) was heated in 16 ml of 6N HCl at 100°–110° C. for 18 h. This was then concentrated to dryness and methanol-ether was added and the formed solid was collected to yield 55 mg (73%) of the desired product after drying. m.p. 268°–270° C. $^1$H NMR (TFA) δ: 9.21 (s, 1H), 8.74 (s, 1H), 8.58 (s, 1H), 8.20 (d, 11.4Hz, 1H), 6.14–5.84 (m, 1H), 4.94–4.3 (m, 4H), 4.18–3.95 (m, 1H), 3.18–2.8 (m, 2H), 1.68–1.18 (m, 4H). Anal. calcd. for C$_{18}$H$_{17}$FN$_6$O$_3$.1/2 H$_2$O; C, 54.96; H, 4.61; N, 21.35. Found: C, 54.66; H, 4.51; N, 20.85.

EXAMPLE 6

Ethyl 7-[cis-3-amino-4-f1,2,3-triazol-1-yl)pyrrolidin-1-yl]-1-cyclopropyl-6-fluoro-1,4-dihydro-4-oxo-1,8-naphthyridine-3-carboxylate Ethyl 7-chloro-1-cyclopropyl-6-fluoro-1,4-dihydro-4-oxo-1,8-naphthyridine-3-carboxylate (243 mg, 0.78 mmol) and cis-3-amino-4-(1,2,3-triazol-1-yl)pyrrolidine (300 mg, 1.96 mmol) were reacted together in 8 ml of pyridine at r.t. for 5 days. The solvent was then evaporated, water was added to the residue and was extracted with chloroform. The organic layer was then dried (Na$_2$SO$_4$) and evaporated to yield 0.23 g of the crude product which upon purification over neutral alumina (activity III) using 4% methanol/chloroform as solvent yielded 200 mg (60%) of the desired product. $^1$H NMR (CDCl$_3$) δ: 8.5 (s, 1H), 8.12 (d, 1H) 7.82 (s, 1H), 7.76 ,f (s, 1H), 5.3–5.15 (s, 1H), 4.55–4.00 (m, 6H) 3.85–3.62 (m, 1H), 3.58–3.4 (m, 1H), 1.43 (t, 3H), 1.32–0.94 (m, 4H).

EXAMPLE 7

7-[cis-3-Amino-4-(1,2,3-triazol-1-yl)pyrrolidin-1-yl)-1-cyclopropyl-6-fluoro-1,4-dihydro-4-oxo-1,8-naphthyridine-3-carboxylic acid hydrochloride Ethyl 7-[cis-3-amino-4-(1,2,3-triazol-1-yl)pyrrolidin-1-yl]-1-cyclopropyl-6-fluoro-1,4-dihydro-4-oxo-1,8-naphthyridine-3-carboxylate (200 mg, 0.47 mmol) was heated with 8 ml of 6N hydrochloric acid at 110° C. for 18 hr. The solution was then evaporated to dryness and the residue was crystallized from methanol-ether to yield 160 mg (85%) of the desired hydrochloride, m.p. 240° C. (dec). $^1$H NMR (TFA) δ: 9.27 (s, 1H), 9.01 (s, 1H), 8.66 (s, 1H), 8.3 (d, 11.6Hz, 1H), 6.64–6.45 (m, 1H), 5.35–4.66 (m, 5H), 4.20–4.02 (m, 1H), 1.7–1.2 (m, 4H). Anal. calcd. for C$_{18}$H$_{19}$ClFN$_7$O$_3$. 1.5 H$_2$O: C, 46.76; H, 4.80; N, 21.2; Cl, 7.67. Found: C, 46.85; H, 4.31; N, 20.62; Cl, 8.36.

EXAMPLE 8

1-(2,4-Difluorophenyl)-6-fluoro-7-[3-(1,2,3-triazol-1-yl)pyrrolidin-1-yl]-1,4-dihydro-4-oxo-1,8-naphthyridine-3-carboxylic acid A mixture of crude ethyl 1-(2,4-difluorophenyl)-6-fluoro-7-[3-(1,2,3-triazol-1-yl)pyrrolidin-1-yl]-1,4-dihydro-4-oxo-1,8-naphthyridine-3-carboxylate (150 mg, 0.31 mmol), THF (15 ml), NaOH (20 mg, 1.5 mmol) and water (15 ml) was heated under reflux for 3 h, cooled and the THF was evaporated. The residue was diluted with water, aqueous solution was acidified and the precipitated yellow solid was filtered, washed with water, dried in vac-oven at 50° C. This solid was washed with ether to get the pure compound. Yield: 50 mg (35.7%), m.p. 253° C. (dec). $^1$H NMR (TFA) δ: 2.85 (m, 2H), 3.70–4.50 (m, 4H), 5.80 (m, 1H), 7.20 (m, 2H), 7.60 (m, 1H), 8.25 (s, 1H), 8.57 (s, 1H), 8.62 (s, 1H), 9.20 (s, 1H).

EXAMPLE 9

1-Cyclopropyl-6-fluoro-7-(3-(1 , 2 , 3-triazol-1-yl)pyrrolidin-1-yl]-1,4-dihydro-4-oxo-quinoline-3-carboxylic acid A mixture of 1-cyclopropyl-6,7-difluoro-1,4-dihydro-4-oxo-quinoline-3-carboxylic acid (120 mg, 0.486 mmol), DBU (190 mg, 1.25 mmol), 3-(1,2,3-triazol-1-yl)pyrrolidine hydrochloride (216 mg, 1.25 mmol) in pyridine (8 ml) was heated at 80° C. for 18 h. The reaction mixture was concentrated and treated with water. The separated solid was collected by filtration, washed with water and acetonitrile to give light brown solid. Yield: 71 mg (38%), m.p. 284° C. (dec). $^1$H NMR (TFA) δ: 1.5 (m, 4H), 3.0 (m, 2H), 4.0 (m, 4H), 4.65 (bs, 1H), 5.9 (bs, 1H), 7.5 (d, 1H), 8.20 (d, 1H), 8.6 (s, 1H), 8.7 (s, 1H), 9.2 (S, 1H).

EXAMPLE 10

1-Cyclopropyl-6,8-difluoro-7-[3-(1,2,3-triazol-1-yl)pyrrolidin -1-yl]-1,4-dihydro-4-oxo-quinoline-3-carboxylic acid A mixture of 1-cyclopropyl-6,7,8-trifluoro-1,4-dihydro-4-oxo-quinoline-3-carboxylic acid (138.5 mg, 0.486 mmol), DBU (190 mg, 1.25 mmol), and 3-(1,2,3-triazol-1-yl)pyrrolidine hydrochloride (216 mg, 1.25 mmol) in pyridine (8 ml) was heated for 20 h at 7580° C. and then pyridine was removed under vacuum. The residue was diluted with acetonitrile. The precipitated solid was washed with acetonitrile, ether and dried at 40° C. Yield: 65 mg (33%), m.p. 244°–246° C. (dec). $^1$H NMR (TFA) δ: 1.5 (m, 4H), 2.8 (m, 2H), 4.5 (m, 4H), 4.75 (bs, 1H), 5.8 (bs, 1H), 8.15 (d, 1H), 8.6 (s, 1H), 8.7 (s, 1H), 9.25 (s, 1H).

EXAMPLE 11

5-Amino-1-cyclopropyl-6,8-difluoro-7-[3-(1-2-3-triazol-1-yl)pyrrolidin-1-yl)-1,4-dihydro-4-oxo-quinoline-3-carboxylic acid A mixture of 5-amino-1-cyclopropyl-6,7,8-trifluoro-1,4-dihydro-4-oxo-quinoline-3-carboxylic acid (190 mg, 0.64 mmol), 3-(1,2,3-triazol-1-yl)pyrrolidine hydrochloride (290 mg, 1.67 mmol) and DBU (255 mg, 1.70 mmol) in pyridine (5 ml) was heated at 110° C. for 20 h. The reaction mixture was then cooled and diluted with methanol. The separated solid was collected and washed successively with methanol, water and acetonitrile. The title compound was obtained upon drying in vac-oven at 40° C. Yield: 168 mg (63%), m.p. 273.5°–275° C. $^1$H NMR (TFA) δ: 1.40 (m, 4H), 2.90 (m, 1H), 4.40 (m, 4H), 4.75 (m, 1H), 5.70 (m, 1H), 8.55 (d, 1H), 8.68 (d, 1H), 9.15 (s, 1H).

EXAMPLE 12

5-Amino-1-cyclopropyl-6,8-difluoro-7-[3S-(1,2,3-triazol-1-yl) pyrrolidin-1-yl]-1,4-dihydro-4-oxo-quinoline-3-carboxylic acid A mixture of 5-amino-1-cyclopropyl-6,7,8-trifluoro-1,4-dihydro-4-oxo-quinoline-3-carboxylic acid (200 mg, 0.67 mmol), 3S-(1,2,3-triazol-1-yl)pyrrolidine hydrochloride (293 mg, 1.68 mmol) and diazabicycloundecane (256 mg, 1.60 mmol) in pyridine (20 ml) was heated at 110° C. for 20 h. The reaction mixture was cooled, diluted with methanol, the separated solid was filtered and washed with H$_2$O and CH$_3$CN, dried to give title product. Yield: 120 mg (43%), m.p. 277°–8° C. $^1$H NMR (TFA) δ: 1.31–1.58 (m, 4H), 2.90 (m, 2H), 4.15–4.54 (m, 4H), 4.75 (m, 1H), 5.86 (m, 1H), 8.55 (d, 1H), 8.69 (d, 1H), 9.15 (s, 1H).

EXAMPLE 13

5-Amino-1-cyclopropyl-6,8-difluoro-7-(3R-(1,2,3-triazol-1-yl) -pyrrolidin-1-yl]-1,4-dihydro-4-oxo-quinoline-3-carboxylic acid Prepared by the same procedure as described in Example 12 by using 5-amino-1-cyclopropyl-6,7,8-trifluoro -1,4-dihydro-4-oxo-quinoline-3-carboxylic acid and 3R -(1,2,3-triazol-1-yl)pyrrolidinehydrochloride. Yield: 41%, m.p. 279°–280° C. $^1$H NMR (TFA) δ: 1.31–1.49 (m, 4H), 2.92 (m, 2H), 4.2–5.1 (m, 4H), 4.73 (m, 1H), 5.82 (m, 1H), 8.56 (d, 1H), 8.68 (d, 1H), 9.10 (s, 1H).

EXAMPLE 14

5-Amino-1-(2,4-difluorophenyl)-6,8-difluoro-7-[3-(1,2,3-triazol-1-yl]pyrrolidin-1-yl]-1,4-dihydro-4-oxoquinoline -3-carboxylic acid A mixture of 5-amino-1-(2,4-difluorophenyl) -6,7,8-trifluoro-1,4-dihydro-4-oxo-quinoline-3-carboxylic acid (200 mg, 0.54 mmol), 3-(1,2,3-triazol-1-yl)pyrrolidine hydrochloride (231 mg, 1.25 mmol) and diazabicycloundecane (200 mg, 1.31 mmol) in acetonitrile (25 ml) was refluxed for 45 h. The separated solid was filtered, washed with acetonitrile and ether to give 150 mg (57%) of desired product, m.p. 307.5°–309° C. $^1$H NMR (TFA) δ: 2.81 (m, 2H), 4.06–4.53 (m, 4H), 5.73 (m, 1H), 7.15–7.23 (m, 2H), 7.59–7.66 (m, 1H), 8.52 (d, 1H), 8.62 (d, 1H), 8.82 (d, 1H).

EXAMPLE 15

5-Amino-1-(2,4-difluorophenyl)-6,8-difluoro-7-[3S-(1,2,3-triazol-1-yl)-pyrrolidin-1-yl]-1,4-dihydro-4-oxo-quinoline-3-carboxylic acid A mixture of 5-amino-1-(2,4-difluorophenyl) -6,7,8-trifluoro-1,4-dihydro-4-oxo-quinoline-3-carboxylic acid (100 mg, 0.27 mmol), 3S-(1,2,3-triazol-1-yl)pyrrolidine hydrochloride (117 mg, 0.67 mmol) and diazabicycloundecane (102 mg, 0.67 mmol) in pyridine (10 ml) was heated at 110° C. for 40 h. The reaction mixture was concentrated and the residue was triturated with water.

The separated solid was filtered, washed with water, acetonitrile and dried under vacuum at 40° C. Yield: 88 mg (67%); m.p. 302–304° C. $^1$H NMR (TFA) δ: 2.82 (m, 2H), 4.0–4.53 (m, 4H), 5.73 (m, 1H), 7.10–7.23 (m, 2H), 7.55–7.70 (m, 1H), 8.52 (d, 1H), 8.62 (d, 1H), 8.82 (d, 1H).

EXAMPLE 16

5-Amino-1-(2,4-difluorophenyl)-6,8-difluoro-7-[3R-(1,2,3-triazol-1-yl)-pyrrolidin-1-yl]-1,4-dihydro-4-oxo-quinoline-3-carboxylic acid Prepared by following the procedure as described in Example 15 by using 5-amino-1(2,4-difluorophenyl)-6,7,8-trifluoro-1,4-dihydro-4-oxo-quinoline-3-carboxylic acid and 3R-(1,2,3-triazol-1-yl)pyrrolidinehydrochloride. Yield: 57%, m.p. 302°-5–304° C. $^1$H NMR (TFA) δ: 2.80–2.90 (m, 2H), 4.05–4.35 (m, 3H), 4.55 (m, 1H), 5.73 (m, 1H), 7.09–7.23 (m, 2H), 7.55–7.70 (m, 1H), 8.53 (d, 1H), 8.62 (d, 1H), 8.82 (d, 1H).

EXAMPLE 17

7-[cis-3-Amino-4-(1,2,3-triazol-1-yl)-pyrrolidin-1-yl]-1-cyclopropyl-6,8-difluoro-1,4-dihydro-4-oxo-quinoline-3-carboxylic acid A mixture of 1-cyclopropyl-6,7,8-trifluoro-1,4-dihydro-4-oxo-quinoline-3-carboxylic acid (44 mg, 0.156 mmol) and cis-3-amino-4-(1,2,3-triazol-1-yl)pyrrolidine (60 mg, 0.39 mmol) in pyridine (5 ml) was heated at 110° C. for 2–3 h under nitrogen and then stirred at room temperature for 20 h. The reaction mixture was concentrated and the residue was washed with water and acetonitrile. The solid was dried under vacuum at 40° C. Yield: 43 mg (66%), m.p. 245°–47° C. $^1$H NMR (TFA) δ: 1.3–1.8 (m, 4H), 4.4–5.25 (m, 6H), 6.40 (m, 1H), 8.15 (d, 1H), 8.62 (s, 1H), 8.90 (s, 1H), 9.40 (s, 1H).

EXAMPLE 18

5-Amino-7-[cis-3-amino-4-(1,2,3-triazol-1-yl)-pyrrolidin-1-yl]-1-cyclopropyl-6,8-difluoro-1,4-dihydro-4-oxo-quinoline-3-carboxylic acid Prepared by following the same procedure as described for Example 17 by using 5-amino-1-cyclopropyl-6,7,8-trifluoro-1,4-dihydro-4-oxo-quinoline-3-carboxylic acid and cis-3-amino-4-(1,2,3-triazol-1-yl)pyrrolidine. Yield: 65%, m.p. 275°–277° C. $^1$H NMR (TFA) δ: 1.33–1.50 (m, 4H), 4.32–5.12 (m, 6H), 6.34 (m, 1H), 8.64 (s, 1H), 8.89 (s, 1H), 9.16 (s, 1H).

EXAMPLE 19

5-Amino-7-[cis-3-amino-4-(1,2,3-triazol-1-yl)-pyrrolidin-1-yl]-1-(2,4-difluorophenyl)-6,8-difluoro-1,4-dihydro-4-oxo-quinoline-3-carboxylic acid Prepared by following the same procedure as described for Example 17 by using 5-amino-1-(2,4-difluorophenyl)-6,7,8-trifluoro-1,4-dihydro-4-oxo-quinoline-3-carboxylic acid and cis-3-amino-4-(1,2,3-triazol-1-yl)-pyrrolidine. Yield: 66%, m.p. 279°–281° C. $^1$H NMR (TFA) δ: 4.48–4.82 (m, 4H), 5.02 (m, 1H), 6.26 (m, 1H), 7.17 (m, 2H), 7.62 (m, 1H), 8.6 (s, 1H), 8.82 (d, 2H).

EXAMPLE 20

5-Amino-7-[trans-3-hydroxy-4-(1,2,3-triazol-1-yl) pyrrolidin-1-yl]-1-cyclopropyl-6,8-difluoro-1,4-dihydro-4-oxo-quinoline-3-carboxylic acid A mixture of 5-amino-1-cyclopropyl-6,7,8-trifluoro-1,4-dihydro-4-oxo-quinoline-3-carboxylic acid (63 mg, 0.21 mmol), trans-3-hydroxy-4-(1,2,3-triazol-1-yl)-pyrrolidine hydrochloride (100 mg, 0.52 mmol) and diazabicycloundecane (79 mg, 0.52 mmol) in pyridine was heated at 110° C. for 20 h. The reaction mixture was concentrated and the residue was triturated with water. The separated solid was filtered, washed with water and acetonitrile and dried under vacuum at 40° C. Yield: 35 mg (40%), m.p. 261°–165.5° C. $^1$H NMR (TFA) δ: 1.33–1.51 (m, 4H), 4.24 (m, 2H), 4.60 (m, 2H), 4.92 (m, 1H), 5.20 (m, 1H), 5.79 (m, 1H), 8.59 (d, 1H), 8.78 (s, 1H), 9.15 (s, 1H).

EXAMPLE 21

1-Cyclopropyl-6,8-difluoro-5-methyl-7-[3-(4-methyl-1,2,3-triazol-1-yl)pyrrolidin-1-yl]-1,4-dihydro-4-oxo-quinoline-3-carboxylic acid A suspension of 50 mg (0.168 mmol) of 1-cyclopropyl-5-methyl-6,7,8-trifluoro-1,4-dihydro-4-oxoquinoline-3-carboxylic acid, 3-(4-methyl-1,2,3-triazol-1-yl)pyrrolidine hydrochloride (79 mg, 0.421 mmol) and 64 mg (0.421 mmol) of DBU (diazabicycloundecane) in dry acetonitrile (5 ml) was refluxed under nitrogen for 46 h. The yellow solution was concentrated to dryness and the residue was triturated with acetonitrile and thus separated solid was filtered. The supernatant was evaporated to dryness and water was added to the residue and separated solid was collected (30 mg, 43%), m.p. 232°–234° C. $^1$H NMR (TFA) δ: 9.26 (s, 1H), 8.37 (s, 1H), 5.78–5.58 (m, 1H) 4.85–4.1 (m, 5H), 3.0–2.7 (m, 5H), 2.68 (s, 3H), 1.65–1.15 (m, 4H). Anal. calcd. for $C_{21}H_{21}F_2N_5O_3$: C, 58.74; H, 4.93; N, 16.31. Found: C, 58.14; H, 5.06; N, 16.08.

EXAMPLE 22

1-Cyclopropyl-6,8-difluoro-7-[3-(1,2,3-triazol-1-yl) azetidin-1-yl]-1,4-dihydro-4-oxoquinoline-3-carboxylic acid 1-Cyclopropyl-6,7,8-trifluoro-1,4-dihydro-4-oxoquinoline-3-carboxylic acid (50 mg, 0.18 mmol) was reacted with 3-(1,2,3-triazol-1-yl) azetidine hydrochloride (72 mg, 0.45 mmol) in 3 ml of dry pyridine in the presence of 68.5 mg (0.45 mmol) of DBU at 80° C. for 16 h. The yellow solution was then evaporated to dryness, water was added to the residue, solid was collected and dried to yield 64 mg (92%) of the desired product. m.p. 315°–316° C. $^1$H NMR (TFA) δ: 9.26 (s, 1H), 8.75 (d, 1.2Hz, 1H), 8.60 (d, 1.2Hz, 1H), 8.10 (d, 11.8Hz, 1H), 6.35–6.0 (m, 1H), 5.8–5.15 (m, 4H), 4.65–4.3 (m, 1H), 1.9–1.3 (m, 4H). Anal. calcd. for $C_{18}H_{15}F_2N_5O_3 \cdot H_2O$: C, 53.33; H, 4.23; N, 17.28. Found: C, 53.68; H, 4.23; N, 17.28.

EXAMPLE 23

5-Amino-1-cyclopropyl-6,8-difluoro-7-[3-(1,2,4-triazol-1-yl)azetidin-1-yl]-1,4-dihydro-4-oxoquinoline-3-carboxylic acid A suspension of 5-amino-1-cyclopropyl-6,7,8-trifluoro-1,4-dihydro-4-oxoquinoline-3-carboxylic acid (75 mg, 0.25 mmol) and 100 mg (0.5 mmol) of 3-(1,2,4- triazol-1-yl)azetidine hydrochloride in 3 ml of dry pyridine, in the presence of 152 mg (1 mmol) of DBU was heated under nitrogen at 75° C. overnight. The suspension was then evaporated to dryness and to the residue water was added and solid collected, washed with water and dried to give 95 mg (94%) of the desired product as a yellow solid. m.p. 293°–295° C. $^1$H NMR (TFA) δ: 9.79 (s, 1H), 9.1 (s, 1H), 8.88 (s, 1H), 6.12–5.88 (m, 1H), 5.45–5.05 (m, 4H), 4.44–4.16 (m, 1H), 1.53–1.18 (m, 4H). Anal. calcd. for $C_{18}H_{16}F_2N_6O_3$: C, 53.74; H, 4.01; N, 20.88. Found: C, 53.60; H, 4.08; N, 20.91.

EXAMPLE 24

1-Cyclopropyl-6,8-difluoro-7-[3-(5-methyl-1,2-3-triazol-1-yl]pyrrolidin-1-yl]-1,4-dihydro-4-oxoquinoline-3-carboxylic acid To 100 mg (0.36 mmol) of 1-cyclopropyl-6,7,8-trifluoro-1,4-dihydro-4-oxoquinoline-3-carboxylic acid and 166 mg (0.9 mmol) of 3-(5-methyl-1,2,3-triazol-1-yl) pyrrolidine hydrochloride in 10 ml of pyridine was added 134 mg (0.9 mmol) of DBU and the resulting solution was heated under nitrogen at 120° C. for 3 days. The very fine suspension was then filtered and evaporation of the supernatant afforded a residue which was crystallized by addition of water. The solid was collected (117 mg), m.p. 199°–200° C. $^1$H NMR (CDCl$_3$) δ: 8.73 (s, 1H), 7.83 (d, 13.7Hz, 1H), 7.5 (s, 1H), 5.1–4.9 (m, 1H), 4.48–3.88 (m, 5H), 2.77–2.45 (m, 2H), 2.4 (s, 3H), 1.4–1.1 (m, 4H). Anal calcd. for $C_{20}H_{19}F_2N_5O_3H_2O$: C, 55.42; H, 4.88; N, 16.16. Found: C, 55.64; H, 4.49; N, 15.73.

EXAMPLE 25

1-Cyclopropyl-6,8-difluoro-5-methyl-7-[3-(1,2,4-triazol-1-yl)-pyrrolidin-1-yl]-1,4-dihydro-4-oxoquinoline-3-carboxylic acid 1-Cyclopropyl-5-methyl-6,7,8-trifluoro-1,4-dihydro-4-oxoquinoline-3-carboxylic acid (30 mg, 0.1 mmol) was reacted with 40 mg (0.2 mmol) of 3-(1,2,4-triazol-1-yl)pyrrolidine hydrochloride in 2 ml of pyridine in the presence of 70 mg (0.45 mmol) of DBU at 95° C. overnight. The orange solution was evaporated to dryness and to the residue water was added. The orange solid was collected and washed with methanol to yield 19 mg of the crude product, which upon further purification from methanol yielded 12 mg of the desired product. m.p. 207°–210° C. $^1$H NMR (TFA) δ: 9.81 (s, 1H), 9.27 (s, 1H), 8.78 (s, 1H), 5.75–5.55 (m, 1H), 4.83–4.12 (m, 5H), 3.0–2.7 (m, 5H), 1.7–1.2 (m, 4H). Anal. calcd. for $C_{20}H_{19}F_2N_5O_3H_2O$: C, 55.43; H, 4.88; N, 16.16. Found: C, 55.72; H, 4.73; N, 15.65.

EXAMPLE 26

1-Cyclopropyl-6,8-difluoro-5-methyl-7-[3-(1,2,3-triazol-1-yl)pyrrolidin-1-yl]-1,4-dihydro-4-oxoquinoline-3-carboxylic acid 1-Cyclopropyl-5-methyl-6,7,8-trifluoro-1,4-dihydro-4-oxoquinoline-3-carboxylic acid (30 mg, 0.1 mmol) was reacted with 35 mg (0.2 mmol) of 3-(1,2,3-triazol-1-yl)pyrrolidine hydrochloride in 2 ml of dry pyridine under nitrogen in the presence of 30.4 mg (0.2 mmol) of DBU under reflux conditions. The solvent was removed under reduced pressure and to the orange viscous oil water was added and the solid was collected which was further purified from methanol to yield 20 mg of the desired product, m.p. 228°–230° C. $^1$H NMR (TFA) δ: 9.28 (s, 1H), 8.68 (s, 1H), 8.57 (d, 1.4Hz, 1H), 5.9–5.75 (m, 4.14 (m, 5H), 3.1–2.72 (m, 5H), 1.7–1.2 (m, 4H).

EXAMPLE 27

5-Amino-1-cyclopropyl-6,8-difluoro-7-[3-(4-methyl-1,2,3-triazol-1-yl)pyrrolidin-1-yl]-1,4,dihydro-4-oxoquinoline-3-carboxylic acid 5-Amino-1-cyclopropyl-6,7,8-trifluoro-1,4-dihydro-4-oxoquinoline-3-carboxylic acid (298 mg, 1 mmol) was reacted with 470 mg (2.5 mmol) of 3-(4-methyl-1,2,3-triazol-1-yl)pyrrolidine hydrochloride in the presence of 380 mg (2.5 mmol) of DBU in 20 ml of dry acetonitrile for two days under reflux conditions and the atmosphere of nitrogen. The yellow suspension was then evaporated to dryness and to the residue water was added. The yellow solid was filtered and crystallized repeatedly (3x) with acetonitrile to free the product from the unreacted starting material. After drying, 200 mg of the desired product was obtained, m.p. 271°–272.5° C. $^1$H NMR (TFA) δ: 9.15 (s, 1H), 8.4 (s, 1H), 5.8–5.6 (m, 1H), 4.8–4.05 (m, 5H), 3.0–2.7 (m, 2H), 2.67 (s, 3H), 1.65–1.2 (m, 4H). Anal. calcd. for $C_{20}H_{20}F_2N_6O_3 \cdot \frac{1}{2} H_2O$: C, 54.67; H, 4.82; N, 19.12. Found: C, 54.91; H, 4.69; N, 18.76.

EXAMPLE 28

1-Cyclopropyl-6,8-difluoro-7-[3-(4,5-dimethyl-1,2,3-triazol-1-yl)pyrrolidin-1-yl]-1,4-dihydro-4-oxoquinoline-3-carboxylic acid 1-Cyclopropyl-6,7,8-trifluoro-1,4-dihydro-4-oxoquinoline-3-carboxylic acid (100 mg, 0.36 mmol) was reacted with 3-(4,5-dimethyl-1,2,3-triazol-1-yl)pyrrolidine hydrochloride (182 mg, 0.9 mmol) in 8 ml of dry pyridine in the presence of 137 mg (0.9 mmol) of DBU at 115° C. for five days. The small amount of the solid was filtered off and the supernatant was evaporated to dryness. To the residue, water and a few drops of acetonitrile were added. The solid was collected to afford after drying 125 mg (81%) of the desired product as a gray solid. m.p. 230–232 ° C. (dec). $^1$H NMR (CDCl$_3$) δ: 8.74 (s, 1H), 7.84 (d, J=13.2Hz, 1H), 5.07–4.8 (m, 1H), 4.4–3.85 (m, 5H), 2.8–2.14 (m, 8H, singlet at 2.29, 6H), 1.4–1.0 (m, 4H). Anal. calcd. for $C_{21}H_{12}F_2N_5O_3 \cdot \frac{1}{2} H_2O$: C, 57.52; H, 4.83; N, 15.97. Found: C, 57.68; H, 4.81; N, 15.68.

EXAMPLE 29

1-Cyclopropyl-6,8-difluoro-7-[3-(4-methyl-1,2,3-triazol-1-yl)pyrrolidin-1-yl]-1,4-dihydro-4-oxoquinoline-3-carboxylic acid 1-Cyclopropyl-6,7,8-trifluoro-1,4-dihydro-4-oxoquinoline-3-carboxylic acid (150 mg, 0.53 mmol) was reacted with 249 mg (1.33 mmol) of 3-(4-methyl-1,2,3-triazol-1-yl)pyrrolidine hydrochloride in the presence of 201 mg (1.33 mmol) of DBU in 15 ml of dry pyridine under nitrogen at 120° C. for 3 days. Small amounts of the solid present were removed by filtration, and the supernatant was concentrated under reduced pressure. Water and small amounts of acetonitrile were added to the residue and the grey solid was collected and dried to afford 180 mg (82%) of the desired product, m.p. 219°–220° C. $^1$H NMR (CDCl$_3$) δ: 8.73 (s, 1H), 7.85 (dd, J=13.7Hz, 1.9HZ, 1H), 7.42 (s, 1H), 5.4–5.3 (m, 1H), 4.4–3.7 (m, 5H), 2.7–2.5 (m, 2H), 2.37 (s, 3H), 1.4–1.05 (m, 4H). Anal. calcd. for $C_{20}H_{19}F_2N_5O_3$: C, 57.83; H, 4.57; N, 16.86. Found: C, 57.81; H, 4.60; N, 16.31.

EXAMPLE 30

5-Amino-1-cyclopropyl-6,8-difluoro-7-[3-(1,2,4-triazol-1-yl)pyrrolidin-1-yl]-1,4-dihydro-4-oxoquinoline-3-carboxylic acid To a suspension of 60 mg (0.2 mmol) of 5-amino -1-cyclopropyl-6,7,8-trifluoro-1,4-dihydro-4-oxoquinoline -3-carboxylic acid and 80 mg of 3-(1,2,4-triazol-1-yl)pyrrolidine hydrochloride in 3 ml of dry pyridine under nitrogen was added 140 mg (0.9 mmol) of DBU, and the suspension was heated at 95° C. for 22 h. The resulting orange solution was then evaporated to dryness, water was added to the residue, and the orange solid was collected and washed with methanol to give 50 mg (60%) of yellowish solid after drying in vac-oven, m.p. 240.3°-242-3° C. $^1$H NMR (TFA) $\delta$: 9.8 (s, 1H), 9.14 (s, 1H), 8.77 (s, 1H), 5.78-5.55 (m, 1H), 4.76-4.12 (m, 5H), 2.9-2.65 (m, 2H), 1.65-1.2 (m, 4H). Anal. calcd. for $C_{19}H_{18}F_2N_6O_3$: C, 54.81; H, 4.36; N, 20.17. Found: C, 54.52; H, 4.44; N, 20.00.

EXAMPLE 31

5-Amino-1-cyclopropyl-6,8-difluoro-7-[3-(1,2,3-triazol-1-yl)azetidin-1-yl]-1,4-dihydro-4-oxoquinoline-3-carboxylic acid A solution of 75 mg (0.25 mmol) of 5-amino-1-cyclopropyl-6,7,8-trifluoro-1,4-dihydro-4-oxoquinoline-3-carboxylic acid and 3-(1,2,3-triazol-1-yl)azetidine hydrochloride (99.7 mg, 0.625 mmol) in 3 ml of pyridine in the presence of 95 mg of DBU was heated at 75° C. overnight. The resulting suspension was evaporated to dryness and to the residue, water was added and the separated yellow solid was collected (99 mg, 98%), m.p. >330° C. (dec). $^1$H NMR (TFA) $\delta$: 9.1 (s, 1H), 8.74 (s, 1H), 8.6 (s, 1H), 6.2-5.98 (m, 1H), 5.55-5.05 (m, 4H), 4.45-4.15 (m, 1H), 1.65-1.2 (m, 4H). Anal. calcd. for $C_{18}H_{16}F_2N_6O_3$: C, 53.74; H, 4.01; N, 20.88. Found: C, 53.63; H, 3.99; N, 20.20.

EXAMPLE 32

1-Cyclopropyl-6,8-difluoro-7-[3-(1,2,4-triazol-1-yl)pyrrolidin-1-yl]-1,4-dihydro-4-oxoquinoline-3-carboxylic acid To a solution of 1-cyclopropyl-6,7,8-trifluoro -1,4-dihydro-4-oxoquinoline-3-carboxylic acid (70.75 mg, 0.25 mmol) and 3-(1,2,4-triazol-1-yl)pyrrolidine hydrochloride (100 mg) 3 ml of dry pyridine under nitrogen was added 152 mg (1 mmol) of DBU and the solution was heated at 95° C. overnight. The orange solution was then concentrated under reduced pressure and water was added to the residue and the solid was collected and dried to yield 50 mg (50%) of a gray solid, m.p. 219.7°-220.7° C. $^1$H NMR (TFA) $\delta$: 9.8 (s, 1H), 9.29 (s, 1H), 8.78 (s, 1H), 8.11 (d, J=12.5, 1H), 5.85-5.58 (m, 1H), 4.9-4.2 (m, 5H), 3.00-2.7 (m, 2H), 1.75-1.3 (m, 4H). Anal. calcd. for $C_{19}H_{17}F_2N_5O_3$: C, 56.86; H, 4.27; N, 17.45. Found: C, 56.80; H, 4.41; N, 17.48.

EXAMPLE 33

1-Cyclopropyl-6,8-difluoro-7-[3-(1,2,4-triazol-1-yl) pyrrolidin-1-yl]-1,4-dihydro-4-oxoquinoline-3-carboxylic acid methanesulfonate 1-cyclopropyl-6,8-difluoro-7-[3-(1,2,4-triazol -1-yl)pyrrolidin-1-yl]-1,4-dihydro-4-oxoquinoline-3-carboxylic acid (20 mg, 0.05 mmol) was dissolved in 2 ml of chloroform and to this was added 4 ml of methanesulfonic acid in chloroform. The suspension formed was stirred at room temperature for five hr. The solid was collected to yield 12 mg of white solid after drying very well in the oven, m.p. 208.5°-210° C. $^1$H NMR (CD$_3$OD) $\delta$: 9.54 (s, 1H), 8.78 (s, 1H), 8.64 (s, 1H), 7.81 (dd, 13.8, 2.3Hz, 1H), 5.47-5.3 (m, 1H), 4.5-3.8 (m, 5H), 2.88-2.5 (m, 2H), 2.7 (s, 3H), 1.4-1.1 (m, 4H). Anal. calcd. for $C_{20}H_{21}F_2N_5O_6S \cdot H_2O$: C, 46.60; H, 4.50; N, 13.59. Found: C, 46.75; H, 4.38; N, 13.51.

EXAMPLE 34

1-Cyclopropyl-6-fluoro-7-[3S-(1,2,3-triazol-1-yl)pyrrolidin-1-yl]-8-methoxy-1,4-dihydro-4-oxoquinoline -3-carboxylic acid To 50 mg (0.15 mmol) of ethyl 6,7-difluoro-1-cyclopropyl-8-methoxy-1,4-dihydro-4-oxoquinoline-3-carboxylate was added 1 ml of fluoroboric acid (50% in water) and the mixture was heated at 90°-100° C. for 3 hr. The solution was then poured into water and solid collected (60 mg). The white solid was dissolved in 1 ml of DMSO and to this solution was added 52 mg (0.3 mmol) of 3S-(1,2,3-triazol-1-yl)pyrrolidine hydrochloride and 46 mg (0.3 mmol) of DBU. The mixture was then heated at 90° C. for 42 hr. The reaction mixture was cooled to room temperature and water was added and solid collected. This solid was dissolved in 8 ml of 80% methanol and 0.25 ml of triethylamine was added and refluxed for 4 hr. The solution was cooled and the few particles were filtered. The supernatant was evaporated to dryness, and ethanol was added to the residue, the solid collected, washed with ether and dried to yield 10 mg of the desired product, m.p. 195°-197 ° C. $^1$H NMR (TFA) $\delta$: 9.34 (s, 1H), 8.68 (s, 1H), 8.57 (d, 1H), 8.09 (d, 13.2Hz, 1H), 5.95-5.8 (m, 1H), 4.85-4.3 (m, 4H), 4.2-4.0 (m, 1H), 3.79 (s, 3H), 3.1-2.7 (m, 2H), 1.7-1.1 (m, 4H).

EXAMPLE 35

1-Cyclopropyl-6-fluoro-7-[3-(1,2,3-triazol-1-yl) pyrrolidin-1-yl]-8-methoxy-1,4-dihydro-4-oxoquinoline -3-carboxylic acid Ethyl-6,7-difluoro-1-cyclopropyl-8-methoxy-1,4-dihydro-4-oxoquinoline-3-carboxylate was complexed with fluoroboric acid according to the procedure described in Example 34, and then reacted with 3-(1,2,3-triazol-1-yl)pyrrolidine under the same reaction conditions, followed by hydrolysis to yield the desired product, m.p. 200°-201° C. $^1$H NMR (TFA) $\delta$: 9.34 (s, 1H), 8.69 (d, 1H), 8.58 (d, 1H), 8.09 (d, 13.3HZ, 1H), 5.93-5.8 (m, 1H), 4.83-4.34 (m, 4H), 4.2-4.0 (m, 2H), 3.79 (s, 3H), 3.05-2.75 (m, 2H), 1.7-1.1 (m, 4H). Anal. calcd. for $C_{20}H_{20}FN_5O_4 \cdot \frac{1}{2} H_2O$: C, 56.87; H, 5.01; N, 16.58. Found: C, 56.86; H, 4.68; N, 16.24.

EXAMPLE 36

1-Cyclopropyl-6-fluoro-7-[3-(4-methyl-1,2,3-triazol-1-yl)pyrrolidin-1-yl]-8-methoxy-1,4-dihydro-4-oxoquinoline -3-carboxylic acid The borane complex prepared according to the Example 34 is reacted with 3-(4-methyl-1,2,3-triazol-1-yl)pyrrolidine and the resulting conjugated product was subjected to the same hydrolysis procedure to yield 10 mg of the desired product, m.p. 174°-176° C. $^1$H NMR (TFA) $\delta$: 9.34 (s, 1H), 8.39 (s, 1H), 8.08 (d, 13.4Hz, 1H), 5.84-5.16 (m, 1H), 4.78-4.18 (m, 4H), 4.2-4.0 (m, 1H), 3.78 (s, 3H), 3.08–2.7 (m, 2H), 2.67 (s, 3H), 1.75–1.05 (m, 4H). Anal. calcd. for $C_{21}H_{22}FN_5O_4$. 1 ½ $H_2O$: C, 55.50; H, 5.54; N, 15.41. Found: C, 55.73; H, 4.95; N, 14.63.

EXAMPLE 37

1-Cyclopropyl-6-fluoro-7-[3-(1,2,4-triazol-1-yl) pyrrolidin-1-yl]-8-methoxy-1,4-dihydro-4-oxoquinoline-3-carboxylic acid The borane complex of ethyl 6,7-difluoro-1-cyclopropyl-8-methoxy-1,4-dihydro-4-oxoquinoline-3-carboxylate (50 mg) was formed according to the procedure described for Example 34, and reacted in the same manner with 3-(1,2,4-triazol-1-yl)pyrrolidine hydrochloride. The product from this reaction was then hydrolyzed using triethylamine as described in Example 34 to yield the desired product, m.p. 221°–222° C. $^1$H NMR (TFA) δ: 9.82 (s, 1H), 9.34 (s, 1H), 8.79 (s, 1H), 8.08 (d, 13.3Hz, 1H), 5.85–5.64 (m, 1H), 4.8–4.3 (m, 4H), 4.25–4.0 (m, 1H), 3.81 (s, 3H), 3.0–2.7 (m, 2H), 1.7–1.1 (m, 4H).

EXAMPLE 38

N,N,N-Trimethyl-N-(2-hydroxyethyl)-ammonium-1-cyclopropyl-6,8-difluoro-7-[3-(4-methyl-1,2,3-triazol-1-yl)pyrrolidin-1-yl]-1,4-dihydro-4-oxoquinoline-3-carboxylate To a suspension of 1-cyclopropyl-6,8-difluoro-7-[3-(4-Methyl-1,2,3-triazol-1-yl)pyrrolidine-1-yl]-1,4-dihydro-4-oxoquinoline-3-carboxylic acid (415.5 mg, 1 mmol) in 2.5 ml of methanol and 0.8 ml water at room temperature was added slowly 0.31 ml Of 45% N,N,N-trimethyl-2-hydroxyethyl-ammonium hydroxide in methanol (1 mmol). The solution was stirred at room temperature for an additional hour. This was filtered and the supernatant was evaporated under reduced pressure at 30° C. The residue was crystallized from acetone-methanol to yield after drying 420 mg of off-white solid, m.p. 188.7°–190.7° C. $^1$H NMR (D2O) δ: 8.44 (s, 1H), 7.84 (bs, 1H), 7.62 (bd, 13.9Hz, 1H), 5.43–5.22 (m, 1H), 4.35–3.62 (m, 7H), 3.52 (t, 2H), 3.21 (s, 9H), 2.73–2.16 (m, 2H) 2.29 (s, 3H), 1.74–0.9 (m, 4H). Anal. calcd. for $C_{25}H_{32}F_2N_6O_4$ . ½ $H_2O$: C, 56.98; H, 6.31; N, 15.94. Found: C, 56.76; H, 6.26; N, 15.43.

EXAMPLE 39

N-(2-Hydroxyethyl)ammonium-1-cyclopropyl-6,8-difluoro-7[3-(4-methyl-1,2,3-triazol-1-yl)-pyrrolidin-1-yl]-1,4-dihydro-4-oxoquinoline-3-carboxylate A suspension of 2 0 mg (0.05 mmol) of 1-cyclopropyl-6,8-difluoro-7-[3-(4-methyl-1,2,3-triazol-1-yl) pyrrolidine-1-yl]-1,4-dihydro-4-oxoquinoline-3-carboxylic acid in 2 ml of ethanol was reacted with 3.054 mg (0.05 mmol) of ethanolamine at room temperature for 2 hr. Additional equivalent of ethanolamine was added and the reaction mixture was stirred overnight. The solid was then collected, m.p. 215.5°–216.8° C. $^1$H NMR (D2O) δ: 8.46 (s, 1H), 7.86 (bs, 1H), 7.68 (bd, 14Hz, 1H), 5.46–5.25 (m, 1H), 4.4–3.7 (m, 7H), 3.17–3.07 (m, 2H), 2.76–2.2 (m, 5H), 2.31 (s, 3H), 1.3–1.0 (m, 4H). Anal. calcd. for $C_{22}H_{26}F_2N_6O_4$ $H_2O$: C, 53.44; H, 5.71; N, 16.99. Found: C, 53.68; H, 5.93; N, 16.48.

EXAMPLE 40

N,N,N-Trimethyl-N-(2-hydroxyethyl)-ammonium-1-cyclopropyl-6,8-difluoro-7-[3-(1,2,4-triazol-1-yl)pyrrolidin-1-yl]-1,4-dihydro-4-oxoquinoline-3-carboxylate To a suspension of 100.25 mg (0.25 mmol) of 1-cyclopropyl-6,8-difluoro-7-[3-(1,2,4-triazol-1-yl) pyrrolidin-1-yl]-1,4-dihydro-4-oxoquinoline-3-carboxylic acid in 0.625 ml of methanol and 0.2 ml of water was added at room temperature slowly 0.075 ml of 45% choline in methanol. The solution was stirred at room temperature for an additional hour and after being through a cotton filter, the supernatant was evaporated to dryness under reduced pressure (30° C.). The residue was crystallized from acetone-methanol and dried to give 85 mg of off white solid, m.p. 193°–194° C. $^1$H NMR (CD3OD) δ: 8.61 (s, 1H), 8.42 (bs, 1H), 8.01 (s, 1H), 7.76 (dd, 14Hz, 1.8Hz, 1H), 5.3–5.15 (m, 1H), 4.3–3.75 (m, 7H), 3.5–3.44 (m, 2H), 3.21 (s, 9H), 2.62–2.45 (m, 2H), 1.22–1.02 (m, 4H). Anal. calcd. for $C_{24}H_{30}F_2N_6O_4$ $H_2O$: C, 55.16; H, 6.13; N, 16.07. Found: C, 54.46; H, 5.91; N, 15.82.

EXAMPLE 41

(−)-9-Fluoro-3 (S)-methyl-10-[3-(1,2,3-triazol-1-yl) pyrrolidin-1-yl]-7-oxo-2,3-dihydro-7H-pyrido-[1,2,3de]-1,4-benzoxazine-6-carboxylic acid To a suspension of 76 mg (0.27 mmol) of (−) -9,10-difluoro-3(S)-methyl-7-oxo-2,3-dihydro-7H -pyrido[1,2,3-de]-1,4-benzoxazine-6-carboxylic acid and 118 mg (0.675 mmol) of 3-(1,2,3-triazol-1-yl) pyrrolidine hydrochloride in 10 ml of dry acetonitrile was added 121 mg (0.81 mmol) of DBU. The reddish brown solution was refluxed for 31 hr. The solvent was then removed under reduced pressure. To the residue water was added and extracted with chloroform. The organic layer was then evaporated to dryness, and to the residue, water was added and solid collected to yield 10 mg of the desired product, m.p. 225°–229° C. $^1$H NMR (TFA) δ: 9.17 (s, 1H), 8.67 (s, 1H), 8.57 (s, 1H), 7.99 (d, 13.3Hz, 1H), 5.9–5.18 (m, 1H), 5.22–4.07 (m, 7H), 3.13–2.63 (m, 2H), 1.82 (s, 3H), 1.79 (s, 3H). Anal. calcd. for $C_{19}H_{18}N_5O_4F$ . ½ $H_2O$: C, 55.86; H, 4.69; N, 17.16. Found: C, 55.93; H, 4.59; N, 16.37.

EXAMPLE 42

(−)-9-Fluoro-3(S)-methyl-10-[3-(4-methyl-1,2,3-triazol-1-yl)pyrrolidin-1-yl]-7-oxo-2,3-dihydro-7H-pyrido-[1,2,3-de]-1,4-benzoxazine-6-carboxylic acid A solution of 70.25 mg (0.25 mmol) of (−)-9,10-difluoro-3(S)-methyl-7-oxo-2,3-dihydro-7H-pyrido[1,2,3-de]-1,4-benzoxazine-6-carboxylic acid and 141 mg (0.75 mmol) of 3-(4-methyl-1,2,3-triazol-1-yl)pyrrolidine hydrochloride in 3 ml of acetonitrile in the presence of 152.24 mg (1 mmol) of DBU was refluxed for 3 days under nitrogen atmosphere. The suspension was then evaporated and water was added to the residue and solid collected and washed with methanol to yield after drying 50 mg of the desired product, m.p. 241°–242° C. $^1$H NMR (TFA) δ: 9.16 (s, 1H), 8.37 (s, 1H), 7.99 (d, 13.3Hz, 1H), 5.75–5.6 (m, 1H), 5.15–4.1 (m, 7H), 3–2.6 (m, 2H), 2.67 (s , 3H), 1.8 (d, 6.8Hz, 3H). Anal. calcd. for $C_{20}H_{20}FN_5O_4$ . ½ $H_2O$: C, 56.87; H, 5.01; N, 16.58. Found: C, 57.30; H, 4.77; N, 16.75.

EXAMPLE 43

(−)-9-Fluoro-3(S)-methyl-10-[3-(1,2,4-triazol-1-yl) pyrrolidin-1-yl]-7-oxo-2,3-dihydro-7H-pyrido-[1,2,3-de]-1,4-benzoxazine-6-carboxylic acid A suspension of 70.25 mg (0.25 mmol) of (−) -9,10-difluoro-3(S)-methyl-7-oxo-2,3-dihydro-7H-pyrido [1,2,3-de]-1,4-benzoxazine-6-carboxylic acid and 87 mg (0.5 mmol) of 3-(1,2,4-triazol-1-yl)pyrrolidine hydrochloride in 3 ml of acetonitrile in the presence of 76 mg (0.5 mmol) DBU was stirred under nitrogen at reflux condition overnight. The yellow solution was then evaporated to dryness and to the residue, water was added and solid collected. The off-white solid was dissolved in chloroform and the small amounts of the suspension were filtered off. The supernatant was evaporated and to the residue, water was added and solid collected (60 mg), m.p. 229°–231° C. $^1$H NMR (CDCl$_3$) δ: 8.59 (s, 1H), 8.26 (s, 1H), 7.98 (s, 1H), 7.7 (d, 13.5Hz, 1H), 5.17–5.00 (m, 1H), 4.6–3.73 (m, 7H), 2.67–2.4 (m, 2H), 1.61 (d, 6.7Hz, 3H).

EXAMPLE 44

5-Amino-1-cyclopropyl-6,8-difluoro-7-[3-(4-amino-1,2,3-triazol-1-yl)pyrrolidin-1-yl]-1,4-dihydro-4-oxoquinoline -3-carboxylic acid A mixture of 5-amino-1-cyclopropyl-6,7,8-trifluoro-1,4-dihydro-4-oxoquinoline-3-carboxylic acid (100 mg, 0.67 mmol), 3-(4-amino-1,2,3-triazol-1-yl)pyrrolidine dihydrochloride (185 mg, 0.83 mmol) and diazabicycloundecane (127 mg, 0.83 mmol) in pyridine (3 ml) was heated at 110° C. for 24 hrs. Reaction mixture was concentrated to dryness under vacuum and residue was dissolved in water, extracted with methylene chloride, dried over sodium sulfate and concentrated to dryness. The solid residue thus obtained was crystallized from chloroform to brown solid. Yield 15 mg (10.4%), m.p. 210°–213° C. $^1$H NMR (TFA) δ: 1.22–1.58 (m, 4H), 2.70–2.90 (m, 2H), 4.06–4.54 (m, 5H), 5.48–5.60 (m, 1H), 7.79 (s, 1H), 9.14 (s, 1H).

EXAMPLE 45

1-Cyclopropyl-6,8-difluoro-7-[3-(4-amino1,2,3-triazol-1-yl)pyrrolidin-1-yl]-1,4-dihydro-4-oxoquinoline-3-carboxylic acid A mixture of 1-cyclopropyl-6,7,8-trifluoro -quinolone-3-carboxylic acid (75 mg, 0.26 mmol), 3-(4-amino-1,2,3-triazol-1-yl)pyrrolidine (145 mg, 0.65 mmol) and diazabicycloundecane (198 mg, 1.30 mmol) in acetonitrile (5 ml) was heated for 3 days at 110° C. Separated light brown solid was filtered, washed with water and then crystallized from methanol to give 55 mg (50.9%) of title compound, m.p. 221° C. $^1$H NMR (TFA) δ: 1.38–1.72 (m, 4H), 2.66–2.98 (m, 2H), 4.10–4.80 (m, 5H), 5.42–5.64 (m, 1H), 7.7–7.9 (m, 1H) 9.28 (s, 1H).

EXAMPLE 46

1-Cyclopropyl-6,8-difluoro-7-[3-(5-carboxy-1,2,3-triazol -1-yl)pyrrolidin-1-yl]-1,4-dihydro-4-oxoquinoline-3-carboxylic acid A mixture of 5-amino-1-cyclopropyl-6,7,8-trifluoro-1,4-dihydro-4-oxoquinoline-3-carboxylic acid (100 mg, 0.33 mmol), 3-(5-ethoxycarbonyl-1,2,3-triazol-1-yl)pyrrolidine hydrochloride (178 mg, 0.83 mmol) and diazabicycloundecane (127 mg, 0.83 mmol) was heated at 110° C. for 24 hrs. The mixture was concentrated, diluted with water and the separated solid was washed with water and acetonitrile. The solid was dried in air and redissolved in methanol (5 ml) and to it NaOH (20 mg) in water (5 ml) was added. The solution was heated at 90° C. for 6 hrs., cooled and pH lowered using 1N HCl to 4. The separated solid was filtered, recrystallized from methanol/ether, yield 20 mg (13.98%), m.p. 214° C. $^1$H NMR (TFA) δ: 1.30–1.62 (m, 4H), 2.70–3.0 (m, 2H), 3.74–4.80 (m, 5H), 5.60–5.70 (m, 1H), 8.86 (s, 1H), 9.14 (s, 1H).

EXAMPLE 47

1-Cyclopropyl-6,8-difluoro-7-[3-(5-aminomethyl-1,2,3-triazol-1-yl)pyrrolidin-1-yl]-1,4-dihydro-4-oxoquinoline-3-carboxylic acid A mixture of 1-cyclopropyl-6,7,8-trifluoro-1,4-dihydro-4-oxoquinoline (200 mg, 0.706 mmol), 5-aminomethyl- (1,2,3-triazol-1-yl)pyrrolidine dihydrochloride (585 mg, 2.46 mmol) and diazabicycloundecane (325 mg, 2.48 mmol) in pyridine (8 ml) was heated at 110° C. for 20 hrs, concentrated and the residue washed repeatedly with acetonitrile. The solid thus obtained was redissolved in chloroform and then washed with water, brine and dried using anhydrous sodium sulfate. Evaporation of chloroform yielded 120 mg (40.33%) of desired product, m.p 138° C. $^1$H NMR (TFA) δ: 1.30–1.70 (m, 4H), 2.72–3.05 (m, 2H), 4.20–4.67 (m, 5H), 4.73–4.95 (m, 1H), 5.15 (s, 2H), 5.93–6.17 (m, 1H), 8.12 (d, 1H), 8.88–9.30 (s, 1H).

EXAMPLE 48

1-Cyclopropyl-6,8-difluoro-7-[3-(4-carboxy-1,2,3-triazol -1-yl]pyrrolidin-1-yl]-1,4-dihydro-4-oxoquinoline-3-carboxylic acid A mixture of 1-cyclopropyl-6,7,8-trifluoro-1,4-dihydro-4-oxoquinoline-3-carboxylic acid (140 mg, 0.49 mmol), 3-(4-carboxy-1,2,3-triazol-1-yl)pyrrolidine hydrochloride (269 mg, 1.23 mmol) and diazobicycloundecane (187 mg, 1.23 mmol) in acetonitrile (5 ml) was heated at 80°–90° C. for four days. The reaction mixture was concentrated, diluted with water (10 ml) and pH brought down to 4.0 using 1M HCl. The separated solid was filtered and washed with water and crystallized from MeOH/ether to yellow solid. Yield 29 mg (13.2%), m.p. 222°–225° C. $^1$H NMR (CDCl$_3$+CD$_3$OD) δ: 1.11–1.42 (m, 4H), 3.88–4.30 (m, 4H), 4.40–4.48 (m, 1H), 5.35–5.55 (m, 1H), 7.8 (d, 1H), 8.41 (s, 1H), 8.79 (s, 1H).

EXAMPLE 49

1-Cyclopropyl-6,8-difluoro-7-[3-(4-phenyl-1,2,3-triazol-1-yl)pyrrolidin-1-yl]-1,4-dihydro-4-oxoquinoline-3-carboxylic acid A mixture of 1-cyclopropyl-6,7,8-trifluoro-1,4-dihydro-4-oxoquinoline-3-carboxylic acid (150 mg, 0.53 mmol), 3-(4-phenyl-1,2,3-triazol-1-yl)pyrrolidine hydrochloride (252 mg, 1.05 mmol) and diazobicycloundecane (160 mg, 1.05 mmol) in pyridine (5 ml) was heated at 110° C. for 20 hrs, concentrated and diluted with water. The separated solid was filtered, washed with water and crystallized from methanol. Yield: 55 mg (22.3%), m.p. 241.4° C. $^1$H NMR (TFA) δ: 1.34–1.73 (m, 4H), 2.82–3.09 (m, 2H), 4.20–4.95 (m, 5H), 5.73–5.92 (m, 1H), 7.5–7.92 (m, 4H), 8.15 (d, 1H), 8.80 (s, 1H), 9.30 (s, 1H).

EXAMPLE 50

5-Amino-1-cyclopropyl-6,8-difluoro-7-[3-(4-Phenyl-1,2,3-triazol-1-yl)pyrrolidin-1-yl]-1,4-dihydro-4-oxoquinoline-3-carboxylic acid A mixture of 5-amino-1-cyclopropyl-6,7,8-trifluoro-1,4-dihydro-4-oxo-quinoline-3-carboxylic acid (100 mg, 0.33 mmol), 3-(4-phenyl-1,2,3-triazol-1-yl)pyrrolidine hydrochloride (160 mg, 0.42 mmol) and diazobicycloundecane (102 mg, 0.67 mmol) in pyridine (5 ml) was heated at 90° C. for 20 hrs. The reaction mixture was concentrated and the residue was diluted with water. The separated solid was filtered, washed with water, methanol and then with $CHCl_3$, followed by acetonitrile to get 16 mg (10%) of title compound, m.p. 265° C. $^1H$ NMR (TFA) δ: 0.92–1.43 (m, 4H), 2.51–2.80 (m, 2H), 3.57–4.59 (m, 5H), 5.43–5.62 (m, 1H), 7.44 (dd, 5H), 8.50 (s, 1H), 8.84 (s, 1H).

EXAMPLE 51

1-Cyclopropyl-6,8-difluoro-5-methyl-7-[3-(4-Phenyl-1,2,3-triazol-1-yl)pyrrolidin-1-yl]-1,4-dihydro-4-oxoquinoline-3-carboxylic acid A mixture of 1-cyclopropyl-6,7,8-trifluoro-5-methyl-1,4-dihydro-4-oxo-quinoline-3-carboxylic acid (100 mg, 0.37mmol),3-(4-phenyl-1,2,3-triazol-1-yl)pyrrolidine hydrochloride (160 mg, 0.67 mmol) and diazobicycloundecane (102 mg, 0.67 mmol) in (5 ml) pyridine was heated at 90° C. for 24 hrs. The reaction mixture was concentrated and diluted with water. The separated solid was filtered and washed with water followed by ether and was crystallized from methanol. Yield: 89 mg (55%), m.p. 221.4° C. $^1H$ NMR (TFA) δ: 1.20–1.70 (m, 4H), 2.76–3.80 (m, 2H), 4.20–4.96 (m, 5H), 5.74–5.90 (m, 1H), 7.52 (dd, 5H), 8.70 (s, 1H), 9.27 (s, 1H).

EXAMPLE 52

1-Cyclopropyl-5,6,8-trifluoro-7-[3-(1,2,3-triazol-1-yl)pyrrolidin-1-yl]-1,4-dihydro-4-oxo-quinoline-3-carboxylic acid A mixture of ethyl 1-cyclopropyl-5,6,7,8-tetrafluoro-1,4-dihydro-4-oxo-quinoline-3-carboxylate (150 mg, 0.45 mmol), 3-(1,2,3-triazol-1-yl)pyrrolidine hydrochloride (216 mg, 1.24 mmol) and diazobicycloundecane (189 mg, 1.24 mmol) in pyridine (5 ml) was heated at 100° C. for 24 hrs. The reaction mixture was concentrated and water added to it. The separated solid was filtered, dried and crystallized from $CHCl_3$/EtOH mixture. The 50 mg of ester thus obtained was dissolved in methanol (10 ml) and aqueous NaOH (10 mg in 7 ml of water) was added. The mixture was heated under reflux for 4 hrs. The methanol was evaporated and the remaining aqueous solution was acidified to pH 5, the separated white solid filtered, washed with water and dried in the air. Yield: 22 mg (11%), m.p. 250°–253° C. $^1H$ NMR (TFA) δ: 1.25–1.70 (m, 4H), 2.75–3.10 (m, 2H), 4.18–4.95 (m, 5H), 5.72–5.95 (m, 1H), 8.56 (s, 1H), 8.70 (s, 1H), 9.27 (s, 1H).

EXAMPLE 53

1-Cyclopropyl-5-hydroxy-6,8-difluoro-7-[3-(1,2,3-triazol-1-yl)pyrrolidin-1-yl]-1,4-dihydro-4-oxoquinoline-3-carboxylic acid A mixture of ethyl 1-cyclopropyl-5-hydroxy-6,7,8-trifluoro-1,4-dihydro-4-oxo-quinoline-3-carboxylate (100 mg, 0.30 mmol) 3-(1,2,3-triazol-1-yl)pyrrolidine hydrochloride (106.42 mg, 0.61 mmol) and diazobicycloundecane (97 mg, 0.63 mmol) in pyridine (3 ml) was heated at 100° C. for 24 hrs. The reaction mixture was concentrated to dryness and the residue diluted with water. The separated yellow solid was filtered and purified on silica column using $CHCl_3$ as eluant. The purified ester (30 mg) was dissolved in methanol (20 ml) and to it aqueous NaOH (10 mg in 7 ml of water) was added. The solution was heated under reflux for 4 hrs. Methanol was evaporated by distillation and the aqueous solution was acidified using 1N HCl. The precipitated solid was collected by filtration, washed with water and dried at 40° C. under vacuum. Yield: 22 mg (17.25%). $^1H$ NMR (TFA) δ: 1.25–1.62 (m, 4H), 2.72–3.03 (m, 2H), 4.10–4.86 (m, 5H), 5.72–5.88 (m, 1H), 8.55 (s, 1H), 8.67 (s, 1H), 9.14 (s, 1H).

EXAMPLE 54

1-cyclopropyl-6,8-difluoro-7-[3-(1,2,3,4-tetrazol-2-yl)pyrrolidin-1-yl]-1,4-dihydro-4-oxoquinoline-3-carboxylic acid A solution of 1-cyclopropyl-6,7,8-trifluoro-1, 4-dihydro-4-oxo-quinoline-3-carboxylic acid (28.3 mg, 0.1 mmol), 3-(1,2,3,4-tetrazol-2-yl) pyrrolidine hydrochloride (35.1 mg, 0.2 mmol) and DBU (45.6 mg, 0.3 mmol) in acetonitrile (2 ml) was refluxed under nitrogen for 23 hrs. The solvent was then evaporated to dryness. The residue was diluted with water and extracted with chloroform. The organic extract was dried over $Na_2SO_4$, concentrated and the residue was crystallized from methanol-water. Yield: 12 mg, m.p. 192°–199° C. $^1H$ NMR ($CDCl_3$) δ: 8.7 (s, 1H), 8.5 (s, 1H), 7.8 (dd, 1H), 5.6–5.4 (m, 1H), 4.46–3.76 (m, 5H), 2.9–2.45 (m, 2H), 1.35–1.02 (m, 4H).

EXAMPLE 55

1-Cyclopropyl-6,8-difluoro-7-[3-(1,2,3,4-tetrazol-1-yl)pyrrolidin-1-yl]-1,4-dihydro-4-oxoquinoline-3-carboxylic acid A solution of 1-cyclopropyl-6,7,8-trifluoro-1,4-dihydro-4-oxo-quinoline-3-carboxylic acid (42.3 mg, 0.15 mmol), 3-(1,2,3,4-tetrazol-1-yl)pyrrolidinehydrochloride (53 mg, 0.3 mmol) and DBU (68 mg) in acetonitrile (5 ml) was refluxed under nitrogen and stirring for 23 hrs. The reaction mixture was concentrated and the residue was triturated with water. The separated solid was filtered, washed with acetonitrile and dried to yield 28 mg of the product, m.p. 268°–270° C. $^1H$ NMR (TFA) δ: 9.65 (bs, 1H), 9.28 (s, 1H), 8.1 (d, 1H), 5.85–5.65 (m, 1H), 4.9–4.15 (m, 5H), 3.0–2.7 (m, 2H), 1.70–1.25 (m, 4H). Anal. calcd. for $C_{18}H_{16}F_2N_6O_3 \cdot \frac{1}{2} H_2O$: C, 52.56; H, 4.17; N, 20.44. Found: C, 52.91; H, 3.84; N, 20.01.

EXAMPLE 56

1-Cyclopropyl-6,8-difluoro-7-[3-(1,2,3-triazol-1-yl)piperidin-1-yl]-1,4-dihydro-4-oxoquinoline-3-carboxylic acid To a suspension of 1-cyclopropyl-6,7,8-trifluoro-1,4-dihydro-4-oxoquinoline-3-carboxylic acid (50 mg, 0.18 mmol) and 3-(1,2,3-triazol-1-yl)piperidine-1-yl hydrochloride (83 mg, 0.44 mmol) in 3 ml of acetonitrile was added 67 mg (0.44 mmol) of DBU. The solution was heated at reflux under nitrogen for 16 hrs. The suspension was cooled and the solid collected, washed with water, dried to yield 50 mg of the title product, m.p.

239°–240° C. ¹H NMR (TFA) δ: 9.35 (s, 1H), 8.61 (s, 1H), 8.51 (s, 1H), 8.16 (d, J=10.6Hz, 1H), 5.45–5.15 (m, 1H), 4.7–3.55 (m, 5H), 2.85–2.05 (m, 4H), 1.8–1.3 (m, 4H).

EXAMPLE 57

5-Amino-1-cyclopropyl-6,8-difluoro-7-[3-(1,2,3-triazol-1-yl)piperidin-1-yl]-1,4-dihydro-4-oxoquinoline-3-carboxylic acid 3-(1,2,3-triazol-1-yl)pyridine hydrochloride (63 mg, 0.33 mmol) and DBU (77 mg, 0.5 mmol) were added to a suspension of 5-amino-1-cyclopropyl-6,7,8-trifluoro-1,4-dihydro-4-oxo-quinoline-3-carboxylic acid (50 mg, 0.18 mmol) in acetonitrile (5 ml). The reaction mixture was refluxed for 48 hrs and then concentrated under vacuo. The residue was diluted with water and thus separated solid was filtered, washed with water, acetonitrile and dried to give 30 mg of desired product. m.p. 252°–254° C.; ¹H NMR (TFA) δ: 9.36 (s, 1H), 8.65 (s, 1H), 8.53 (s, 1H), 5.28 (m, 1H), 3.60–4.66 (m, 5H), 2.10–2.58 (m, 4H), 1.32–1.68 (m, 4H).

EXAMPLE 58

1-Cyclopropyl-6,8-difluoro-5-methyl-7-[3-(1,2,3-triazol-1-yl)piperidin-1-yl]-1,4-dihydro-4-oxoquinoline-3-carboxylic acid 3-(1,2,3-triazol-1-yl)piperidine hydrochloride (63 mg, 0.33 mmol) and DBU (77 mg, 0.5 mmol) were added to a suspension of 5-methyl-1-cyclopropyl-6,7,8-trifluoro-1,4-dihydro-4-oxoquinoline-3-carboxylic acid (50 mg, 0.17 mmol) in acetonitrile (5 ml). The reaction mixture was refluxed under stirring for 66 hrs and then concentrated. The residue was diluted with water and thus separated solid was filtered, washed with water, acetonitrile and dried to give 35 mg of desired product. m.p. 227°–228.5° C.; ¹H NMR (TFA) δ: 9.35 (s, 1H), 8.53 (s, 1H), 8.65 (s, 1H), 5.30 (m, 1H), 4.60 (m, 1H), 3.55–4.35 (m, 4H), 2.90 (s, 3H), 2.08–2.75 (m, 4H), 1.30–1.55 (m, 4H).

EXAMPLE 59

1-Cyclopropyl-6,8-difluoro-7-[3-(1,2,4-triazol-1-yl)piperidin-1-yl]-1,4-dihydro-4-oxoquinoline-3-carboxylic acid 3-(1,2,4-triazol-1-yl)piperidine hydrochloride (300 mg, 1.59 mmol) and DBU (0.48 g, 3.18 mmol) were added to a suspension of 1-cyclopropyl-6,7,8-trifluoro-1,4-dihydro-4-oxoquinoline-3-carboxylic acid (180 mg, 0.63 mmol) in acetonitrile (15 ml). The reaction mixture was refluxed at 90° C. for 48 hrs and then concentrated under vacuum. The residue was diluted with water and aqueous solution was extracted with chloroform. The organic layer dried over Na₂SO₄, concentrated and the residue was diluted with water. The separated solid was filtered and washed with 2 ml of acetonitrile. Yield 13 mg, m.p. 217° C.; ¹H NMR (TFA) δ: 9.75 (s, 1H), 9.40 (s, 1H), 8.78 (s, 1H), 8.20 (d, 1H), 5.10 (m, 1H), 4.58 (m, 1H), 3.52–4.40 (m, 4H), 2.55 (m, 2H), 2.20 (m, 2H), 1.30–1.70 (m, 4H).

EXAMPLE 60

1-Cyclopropyl-6,8-difluoro-5-methyl-7-[4-(1,2,3-triazol-1-yl)piperidin-1-yl]-1,4-dihydro-4-oxoquinoline-3-carboxylic acid 4-(1,2,3-triazol-1-yl)piperidine hydrochloride (126 mg, 0.66 mmol) and DBU (130 mg, 0.85 mmol) were added to a suspension of 1-cyclopropyl-5-methyl-6,7,8-trifluoro-1,4-dihydro-4-oxoquinoline-3-carboxylic acid (100 mg, 0.34 mmol) in acetonitrile (10 ml). The reaction mixture was refluxed for 24 hrs and then concentrated to dryness. The reaction was diluted with water. The separated solid was filtered and washed with water, acetonitrile and dried to give 70 mg of desired product. m.p. 261°–263° C.; ¹H NMR (TFA) δ: 9.36 (s, 1H), 8.55 (s, 1H), 8.62 (s, 1H), 5.25 (m, 1H), 4.60 (m, 1H), 4.12 (m, 2H), 3.80 (m, 2H), 2.94 (s, 3H), 2.60 (m, 4H), 1.30–1.68 (m, 4H).

EXAMPLE 61

5-Amino-1-cyclopropyl-6,8-difluoro-7-[4-(1,2,3-triazol-1-yl)piperidin-1-yl]-1,4-dihydro-4-oxoquinoline-3-carboxylic acid 4-(1,2,3-triazol-1-yl)piperidine hydrochloride (126 mg, 0.66 mmol) and DBU (130 mg, 0.85 mmol) were added to a suspension of 5-amino-1-cyclopropyl-6,7,8-trifluoro-1,4-dihydro-4-oxoquinoline-3-carboxylic acid (100 mg, 0.34 mmol) in acetonitrile (10 ml). The reaction mixture was refluxed for 24 hrs and then concentrated to dryness. The residue was diluted with water and thus separated solid was filtered, washed with water, acetonitrile and dried to give 65 mg of the desired product. m.p. 274°–276° C.; ¹H NMR (TFA) δ: 9.38 (s, 1H), 8.64 (s, 1H), 8.52 (s, 1H), 5.25 (m, 1H), 4.60 (m, 1H), 4.15 (m, 2H), 3.80 (m, 2H), 2.65 (m, 4H), 1.34–1.70 (m, 4H).

EXAMPLE 62

Ethyl 1-cyclopropyl-6-fluoro-7-[3-(1,2,3-triazol-1-yl]piperidin-1-yl]-1,4-dihydro-4-oxo-1,8-naphthyridine-3-carboxylate 3-(1,2,3-triazol-1-yl)piperidine (150 mg, 0.96 mmol) was added to a solution of ethyl 1-cyclopropyl-6-fluoro-7-chloro-1,4-dihydro-4-oxo-1,8-naphthyridine-3-carboxylate (150 mg, 0.48 mmol) in a mixture of acetonitrile (10 ml) and pyridine (3 ml). The reaction mixture was heated at 100° C. for 6 hrs and then concentrated to dryness. The residue was diluted with water and thus solid separated was filtered, washed thoroughly with water and dried. Yield 90 mg, m.p. 205°–206° C.; ¹H NMR (CDCl₃) δ: 8.58 (s, 1H), 8.15 (d, 1H), 7.78 (s, 1H), 7.65 (s, 1H), 4.90 (m, 2H), 4.40 (m, 3H), 3.45 (m, 3H), 1.75–2.50 (m, 4H), 1.40 (t, 3H), 0.95–1.35 (m, 4H).

EXAMPLE 63

1-Cyclopropyl-6-fluoro-7-[3-(1,2,3-triazol-1-yl)piperidin-1-yl]-1,4-dihydro-4-oxo-1,8-naphthyridine-3-carboxylic acid A mixture of ethyl 1-cyclopropyl-6-fluoro-7-[3-(1,2,3-triazol-1-yl)piperidin-1-yl]-1,4-dihydro-4-oxo-1,8-naphthyridine-3-carboxylate (90 mg, 0.21 mmol) and 6N-HCl (5 ml) was heated to 100°–110° C. for 6 hrs. The mixture was concentrated and the residue was diluted with water. The pH of aqueous solution was adjusted to 7 by the addition of NH₄OH and thus separated solid was filtered, washed with water, acetonitrile and dried to give 30 mg of desired product. m.p. 251°–254° C.; ¹H NMR (TFA) δ: 9.25 (s, 1H), 8.65 (s, 1H), 8.55 (s, 1H), 8.22 (d, 1H), 5.37 (m, 1H), 5.15 (m, 1H), 4.38–4.75 (m, 2H), 4.10 (m, 2H), 2.45–2.85 (m, 2H), 2.00–2.40 (m, 2H), 1.22–1.65 (m, 4H).

EXAMPLE 64

Ethyl 1-cyclopropyl-6-fluoro-7-[4-(1,2,3-triazole-1-yl)piperidin-1-yl]-1,4-dihydro-4-oxo-1,8-naphthyridine-3-carboxylate 4-(1,2,3-triazol-1-yl)piperidine hydrochloride (225 mg, 1.2 mmol) and DBU (182 mg, 1.2 mmol) was added to a suspension of ethyl 1-cyclopropyl-6-fluoro-7-chloro-1,4-dihydro-4-oxo-1,8-naphthyridine-3-carboxylate (150 mg, 0.48 mmol) in a mixture of acetonitrile (10 ml) and pyridine (3 ml). The reaction mixture was heated at 100° C. for 5 hrs. The suspended solid was filtered and the filtrate was concentrated to dryness. The residue was triturated with water and separated solid was filtered, washed with water and dried to give 135 mg of desired product. m.p. 213°–214° C.; $^1$H NMR (CDCl$_3$) δ: 8.48 (s, 1H), 8.11 (d, 1H), 7.72 (s, 1H), 7.60 (s, 1H), 4.60–4.85 (m, 3H), 4.29–4.40 (q, 2H), 3.43–3.54 (m, 1H), 3.21–3.35 (m, 2H), 2.10–2.36 (m, 4H), 1.36 (t, 3H), 0.95–1.23 (m, 4H).

EXAMPLE 65

1-Cyclopropyl-6-fluoro-7-[4-(1,2,3-triazol-1-yl)piperidin-1-yl]-1,4-dihydro-4-oxo-1,8-naphthyridine-3-carboxylic acid A mixture of ethyl 1-cyclopropyl-6-fluoro-7-[4-(1,2,3-triazol-1-yl)piperidin-1-yl]-1,4-dihydro-4-oxo-1,8-naphthyridine-3-carboxylate (135 mg, 0.32 mmol) and 6N-HCl (6 ml) was heated at 110° C. for 18 hrs. The reaction mixture was concentrated and the residue was diluted with water. The pH of the suspension was adjusted to 7 by addition of NH$_4$OH and this separated solid was filtered, washed with water, CH$_3$CN and dried to give 60 mg of title product. m.p. 246°–248° C.; $^1$H NMR (TFA) δ: 9.25 (s, 1H), 8.65 (s, 1H), 8.52 (s, 1H), 8.25 (d, 1H), 5.35 (m, 3H), 4.12 (m, 1H), 3.75 (m, 2H), 2.40–2.85 (m, 4H), 1.25–1.70 (m, 4H).

EXAMPLE 66

1-Cyclopropyl-6-fluoro-8-methoxy-7-[3-(5-methyl-1,2,3-triazol-1-yl)pyrrolidin-1-yl]-1,4-dihydro-4-oxoquinoline-3-carboxylic acid 3-(5-methyl-1,2,3-triazol-1-yl)pyrrolidine hydrochloride (64 mg, 0.34 mmol) and DBU (77 mg, 0.51 mmol) was added to a suspension of 1-cyclopropyl-6,7-difluoro-8-methoxy-1,4-dihydro-4-oxoquinoline-3-carboxylic acid (50 mg, 0.17 mmol) in acetonitrile (5 ml). The reaction mixture was refluxed for 18 hrs and then concentrated to dryness. The residue was triturated with water and thus separated solid was filtered, washed with water, acetonitrile and dried to give 5 mg of title product. m.p. 226°–228° C.; $^1$H NMR (TFA) δ: 9.35 (s, 1H), 8.32 (s, 1H), 8.08 (d, 1H), 5.72 (m, 1H), 4.30–4.80 (m, 4H), 4.10 (m, 1H), 3.80 (s, 3H), 2.90 (m, 2H), 2.72 (s, 3H), 1.12–1.64 (m, 4H).

EXAMPLE 67

N,N,N-Trimethyl-N-(2-hydroxyethyl) ammonium 1-cyclopropyl -6-fluoro-8-methoxy-7-[3-1,2,3-triazol-1-yl[-yl]-1,4-dihydro-4-oxoquinoline-3-carboxylate 1-Cyclopropyl-6,7-difluoro-8-methoxy-7-[3-(1,2,3-triazol-1-yl)pyrrolidin-1-yl]-1,4-dihydro-4-oxoquinoline-3-carboxylic acid (1.032 g, 2.5 mmol) was suspended in 6.25 ml of methanol and 2 ml of water. To this was added 0.775 ml of choline in methanol and the resulting solution was stirred for one hr at room temperature. Filtration followed by evaporation gave a yellow oil which upon crystallization from acetone-ether yielded 1.266 g of the desired product. m.p. 187°–189° C. $^1$H NMR (CD$_3$OD) δ: 8.43 (s, 1H), 8.06 (d, 1Hz, 1H), 7.7 (d, 1Hz, 1H), 7.69 (d, 14.3Hz, 1H), 5.5–5.35 (m, 1H), 4.35–4.15 (m, 1H), 4.1–3.85 (m, 6H), 3.8–3.1 (m, 18H, among those singlets at 3.5, 3H, and 3.14, 9H), 2.75–2.55 (m, 2H), 1.25–0.85 (m, 4H). Anal. calcd. for C$_{25}$H$_{33}$FN$_6$O$_5$ . 1/2 H$_2$O; C, 57.14; H, 6.52; N, 15.98. Found: C, 57.19; H, 6.760: N, 15.63.

EXAMPLE 68

6,8-Difluoro-1-(2-fluoroethyl)-7-[3-(1,2,3-triazol-1-yl)pyrrolidin-1-yl]-1,4-dihydro-4-oxoquinoline-3-carboxylic acid 3-(1,2,3-triazol-1-yl)pyrrolidinehydrochloride (87 mg) and DBU (76 mg) were added to a suspension of 1-(2-fluoroethyl)-6,7,8-trifluoro-1,4-dihydro-4-oxoquinoline-3-carboxylic acid (72 mg, 0.25 mmol) in acetonitrile (5 ml). The reaction mixture was refluxed for 21 hrs, concentrated and the residue was diluted with water. The separated solid was filtered, washed with water and acetonitrile to give 35 mg of the title product. m.p. 240°–243° C. (dec). $^1$H NMR (TFA) δ: 9.76 (s, 1H), 9.08 (s, 1H), 8.73 (s, 1H), 8.12 (d, 13.7Hz, 1H), 5.8–5.6 (m, 1H), 5.4–4.1 (m, 9H), 3.0–2.65 (m, 2H). Anal. Calcd. for C$_{18}$H$_{16}$F$_3$N$_5$O$_3$ . 1/2 H$_2$O; C, 51.93; H, 4.12; N, 16.32. Found: C, 51.77; H, 3.84; N, 15.6.

EXAMPLE 69

(−)-9-Fluoro-3(S)-methyl-10-[4-(1,2,3-triazol-1-yl)piperidin-1-yl]-7-oxo-2,3-dihydro-7-H-pyrido-[1,2,3-de]-1,4-benzoxazine-6-carboxylic acid 4-(1,2,3-triazol-1-yl)piperidine hydrochloride (100 mg) and DBU (80 mg) were added to a suspension of (−)-9,10-difluoro-3(S)-methyl-7-oxo-2,3-dihydro-7H-pyrido [1,2,3-de]-1,4-benzoxazine-6-carboxylic acid in acetonitrile (5 ml). The reaction mixture was refluxed for 48 hrs followed by stirring at room temperature for an additional 48 hrs. The reaction mixture was concentrated and the residue was diluted with water. The separated solid was filtered, washed with water and dried to yield 30 mg of desired product. m.p. 254°–255° C. (dec). $^1$H NMR (TFA) δ: 9.4 (s, 1H), 8.67 (s, 1H), 8.57 (s, 1H), 8.16 (d, 11.43Hz, 1H), 5.6–5.1 (m, 2H), 5.0–4.7 (m, 2H), 4.45–4.05 (m, 4H), 3.1–2.6 (m, 4H), 1.86 (d, 6.3Hz, 3H). Anal. calcd. for C$_{20}$H$_{20}$FN$_5$O$_4$ . H$_2$O; C, 55.68; H, 5.14; N, 16.23. Found C, 55.88; H, 4.762; N, 15.92.

EXAMPLE 70

5-Amino-1-cyclopropyl-6-fluoro-8-methoxy-7-[3-(1,2,3-triazol-1-yl)pyrrolidin-1-yl]-1,4-dihydro-4-oxoquinoline-3-carboxylic acid 3-(1,2,3-triazol-1-yl)pyrrolidinehydrochloride (147 mg, 0.84 mmol) and DBU (128 mg, 0.84 mmol) were added to a suspension of 5-Amino-1-cyclopropyl-6,7-difluoro-8-methoxy-1,4-dihydro-4-oxoquinoline-3-carboxylic acid (100 mg, 0.33 mmol) in pyridine (5 ml). The reaction mixture was heated at 120° C. for 30 hrs, concentrated and the residue was triturated with water. The separated solid was filtered, washed with water and recrystallized from chloroform-hexane. Yield 40 mg; m.p. 208° C.; $^1$H NMR (TFA) δ: 9.39 (s, 1H), 8.70

(s, 1H), 8.57 (s, 1H), 5.88 (s, 1H), 4.43–4.73 (m, 4H), 4.10 (m, 1H), 3.79 (s, 3H), 2.92 (m, 2H), 1.12–1.58 (m, 4H).

EXAMPLE 71

5-Amino-1-cyclopropyl-6-fluoro-8-methoxy-7-[3-(4-methyl-1,2,3-triazol-1-yl)pyrrolidin-1-yl]-1,4-dihydro-4-oxoquinoline-3-carboxylic acid 3-(4-methyl-1,2,3-triazol-1-yl)pyrrolidine hydrochloride (159 mg, 0.85 mmol) were added to a suspension of 5-amino-1-cyclopropyl-6,7-difluoro-8-methoxy-1,4-dihydro-4-oxoquinoline-3-carboxylic acid (100 mg, 0.34 mmol) in pyridine (5 ml). The reaction mixture was heated at 120° C. for 30 hrs, concentrated and the residue was triturated with water. The separated solid was filtered, washed with water and recrystallized from chloroform-hexane. Yield 52 mg; m.p. 255.6°–256.2 ° C. $^1$H NMR (TFA) δ: 9.39 (s, 1H), 8.40 (s, 1H), 5.77 (s, 1H), 4.34–4.83 (m, 4H), 4.10 (m, 1H), 3.79 (s, 3H), 2.89 (m, 2H), 2.68 (s, 3H), 1.22–1.67 (m, 4H).

PREPARATION OF INTERMEDIATES

EXAMPLE A

N-Benzyl-3-(1,2,3-triazol-1-yl)-pyrrolidine

A solution of N-benzyl-3-azido-pyrrolidine (1.5 g, 0.0074 mol) in acetone was taken in a steel bomb and cooled in dry ice/acetone bath. To this cold solution acetylene (2.5 mg, 0.096 mol) was added under $N_2$ atmosphere. The sealed steel bomb was then heated in an oil bath at 75° C. for 20 h. The vessel was cooled again in dry ice/acetone bath and excess of acetylene released slowly, while the temperature rose to the room temperature (r.t.). The reaction mixture was concentrated to yellow-brown oil. Crude yield: 2.02 g. Crude compound was purified on silica gel column to obtain the title compound as a light yellow-brown oil. Yield: 1.02 g (60%). $^1$H NMR (CDCl$_3$) δ: 2.0–3.3 (m, 6H), 3.7 (S, 2H), 5.3 (m, 1H), 7.45 (s, 5H), 7.8 (s, 1H), 7.95 (s, 1H).

EXAMPLE B

3-{1,2,3-triazol-1-yl]-pyrrolidine hydrochloride

To a solution of N-benzyl-3-(1,2,3-triazol-1-yl) pyrrolidine (1 g, 0. 0044 mol), in methanol (50 ml) was added 10 % Pd/C (100 mg) and conc. HCl (1 ml). The suspension was hydrogenated at r.t. and 50 psi pressure for 20 h. The Pd/C was removed by filtration and the solution was concentrated. The residue was recrystallized from methanol/ether to obtain white crystalline title compound. Yield: 680 mg (89.45%). $^1$H NMR (D$_2$O) δ: 2.40–2.80 (m, 2H), 3.58–3.66 (m, 2H), 3.90–3.92 (d, 2H), 5.58–5.67 (m, 1H), 8.02 (d, 1H), 8.26 (d, 1H).

EXAMPLE C

N-(tert-butoxycarbonyl)-3S-(1,2,3-triazol-1-yl)pyrrolidine

A solution of N- (tert-butoxy carbonyl)-3S-azido pyrrolidine (9.1 g, 043 mmol [α$^{24}$$_D$= +40, MeOH) and acetylene (27 g/mmol) in dry acetone (100 ml) was heated at 75° C. for 24 hrs in a pressure reaction vessel. After release of an excess of acetylene, the reaction mixture was concentrated to give 10.1 g of crude oily product. The crude product was purified over silica gel using ethylacetate-hexane (4:1) as eluant. Yield 9.0 g (88%); [α]$_D$$^{24}$= +25° (MeOH) $^1$H NMR (CDCl$_3$) δ: 1.53 (S 9H), 2.53 (m, 2H), 3.80 (m, 4H), 5.26 (m, 1H), 7.70 (S, 1H), 7.80 (S, 1H).

EXAMPLE D

N-(tert-butoxycarbonyl)-3R-(1,2,3-triazol-1-yl)pyrrolidine

Prepared by the same procedure as described in Example C from reaction of N- (tert-butoxy carbonyl)-3R-azido pyrrolidine [α]$^{24}$$_D$= −37, MeOH) and acetylene. Yield 91%, [α]$_D$$^{24}$=25° (MeOH), $^1$H NMR (CDCl$_3$) δ: 1.50 (S, 9H), 2.50 (m, 2H), 3.80 (m, 4H), 5.26 (m, 1H), 7.63 (S, 1H), 7.76 (S, 1H).

EXAMPLE E 3S-(1,2,3-triazol-1-yl]-pyrrolidine hydrochloride

A solution of N-(tert.-butoxy carbonyl)-3S-1,2,3-triazol-1-yl)pyrrolidine (1.0 g, 4.2 mmol) in 20 ml methanol and 2.5 ml of conc. HCl was stirred at room temperature for 30 minutes. The reaction mixture was concentrated and the residue was crystallized from methanol: ether to give 800 mg of the title compound as hydrochloride. [α]$_D$ $^{24}$= − +8° (MeOH), m.p. 189°–92° C.; $^1$H NMR (CD$_3$OD) δ: 2.23 (m, 2H), 3.20 (t, 2H), 3.50 (d, 2H), 5.30 (m, 1H), 7.93 (S, 1H), 8.23 (S, 1H).

EXAMPLE F 3R-(1,2,3-Triazol-1-yl)pyrrolidine hydrochloride

Prepared by following the same procedure as described in example E from N-(tert.-butoxy carbonyl)-3R-(1,2,3-triazol-1-yl)-pyrrolidine. [α]$_D$$^{24}$= −8° (MeOH), m.p. 190°–193 ° C.; $^1$H NMR (CD$_3$OD) δ: 2.20 (m, 2H 3.18 (t, 2H), 3.48 (d, 2H), 5.28 (m, 1H), 7.57 (S, 1H), 7.80 (S, 1H).

EXAMPLE G trans 3-Hydroxy-4-(1,2,3-triazol-1-yl)-1-N-(tertbutoxycarbonyl)pyrrolidine A solution of trans 3-hydroxy-4-azido-1-N-(tert.-butoxy carbonyl)pyrrolidine (3.8 g, 17 mmol) in dry acetone (50 ml) was heated at 75°–80° C. for 40 hrs. After releasing the excess of acetylene, the reaction mixture was concentrated and the residue was purified on silica gel using ethyl acetate as eluant. Yield 3.66 g (87%) m.p. 91–93° C.; $^1$H NMR (CDCl$_3$) δ: 1.46 (S, 9H), 3.25–4.25 (m, 5H), 4.83 (m, 1H), 7.63 (S, 1H), 7.70 (S, 1H).

EXAMPLE H trans 3-Hydroxy-4-(1,2,3-triazol-1-yl) pyrrolidine hydrochloride

Prepared by following the same procedure as described in example E from trans 3-hydroxy-4-(1,2,3-triazol-1-yl)-1-N-(tert-butoxy carbonyl)pyrrolidine. Yield 89%, m.p. 170°–173° C.; $^1$H NMR (CD$_3$OD) δ: 3.00–3.80 (m, 4H), 4.33 (m, 1H), 5.00 (m, 1H), 7.66 (S, 1H), 7.96 (s, 1H).

EXAMPLE I trans3-[(Methylsulfonyl)oxy]-4-(1,2,3-triazol-1-yl)-1-N-(tert-butoxy carbonyl) pyrrolidine)

Methyl sulfonyl chloride (2.84 g, 24.8 mmole) was added slowly to an ice cooled solution of trans 3-hydroxy-4-(1,2,3-triazol-1-yl)-1-N-(tert.-butoxy carbonyl) pyrrolidine (3.16 g, 12.4 mmol) and triethylamine (4.36 ml, 31.3 mmol) in dry CH$_2$Cl$_2$ (10 ml). The reaction mixture was stirred under N$_2$ at room temperature for 22 hrs and washed with saturated NaHCO3 and brine solution. The dichloromethane layer was dried over Na2SO4 and concentrated to give the title product. Yield 4.0 g (97%). $^1$H NMR (CDCl3) δ: 1.5 (S, 9H), 3.07 (s, 3H), 4.07 (m, 4H), 5.43 (m, 2H), 7.70 (S, 1H), 7.90 (S, 1H).

EXAMPLE J cis 3-Azido-4-(1,2,3-triazol-1-yl)-1-N(tert-butoxycarbonyl)pyrrolidine A mixture of compound of example I (4.0 g, 0.012 mol), NH4Cl (0.86 g, 0.016 mol), and sodium azide (4.69 g, 0.072 mole) in a mixture of DMF (32 ml) and water (3.8 mol) was heated at 100° C. for 6 hrs. The reaction mixture was diluted with water and extracted with ethylacetate. The ethyl acetate extract was dried over Na2SO4 and concentrated. The residue was purified over silica gel using ethyl acetate: hexane (2:1) as eluant. Yield 2.85 (85%). $^1$H NMR (CDCl3) δ: 1.48 (S, 9H), 3.90 (m, 4H), 4.45 (m, 1H), 5.36 (m, 1H), 7.70 (S, 1H), 7.80 (S, 1H).

EXAMPLE K cis 3-Amino-4-(1,2,3-triazol-1-yl)-1-N-(tert-butoxy-carbonyl)-pyrrolidine A solution of compound of example J (2.85 g) in methanol (75 ml) was hydrogenated under 50 psi hydrogen pressure over 10% Pd/C (1.1 g) at room temperature for 18 hrs. The mixture was filtered through celite and concentrated to give the title compound. Yield 2.6 g (86%) $^1$H NMR (CDCl3) δ: 1.5 (S, 9H), 3.30 (m, 1H), 4.0 (m, 4H), 5.13 (m, 1H), 7.70 (s, 1H), 7.83 (s, 1H).

EXAMPLE L cis 3-Amino-4-(1,2,3-triazol-1-yl)pyrrolidine

A solution of compound of example K (1.0 g) in trifluoroacetic acid (4 ml) was stirred at room temperature under nitrogen for 10 minutes and concentrated. The residue was dissolved in methanol and treated with basic resin (ANGA-316) and filtered. The filtrate was concentrated and purified by column chromatography over neutral alumina using methanol/CHCl3 mixture as solvent. Yield 670 mg. $^1$H NMR (CD3OD) δ: 2.80 (m, 1H), 3.20–3.80 (m, 5H), 5.10 (m, 1H), 7.75 (s, 1H), 8.0 (S, 1H).

EXAMPLE M

N-Benzyl-3-(4,5-dimethyl-1,2,3-triazol-1-yl)pyrrolidine

To a solution of N-benzyl-3-azidopyrrolidine (2.02 g, 0.01 mole) in 30 ml of 98% ethanol was added 15 ml of butyne and heated in a sealed steel reaction vessel at 105°–110° C. for 24 hr. Removal of the solvent under reduced pressure afforded 2.55 g of the crude which contained 50% starting material. Chromatography over silica gel using hexane/ethyl acetate (1:1) as solvent yielded 0.88 g of the desired product. $^1$H NMR (CDCl3) δ: 7.36–7.2 (m, 5H), 4.95–4.8 (m, 1H), 3.7 (S, 2H), 3.2–3.1 (m, 1H), 2.93–2.76 (m, 3H), 2.48–2.3 (m, 2H), 2.24 (s, 3H), 2.21 (s, 3H).

EXAMPLE N 3-(4,5-Dimethyl-1,2,3-triazol-1-yl)pyrrolidine hydrochloride

10% Pd/C (0.5 g) was added to a solution of 0.86 g of N-benzyl-3-(4 , 5-dimethyl-1,2,3-triazol-1-yl) pyrrolidine in 50 ml of methanol, and 2 ml of 1N hydrochloric acid. The suspension was then hydrogenated at 50 psi pressure overnight. The Pd/C was removed by filtration through celite and the supernatant was evaporated to dryness and crystallized from methanol-ether to yield 0.5 g of the desired product. $^1$H NMR (D2O) δ: 5.75–5.6 (m, 1H), 4.14–3.9 (m, 2H), 3.8–3.6 (m, 2H), 2.86–2.4 (m, 8H, two singlets at 2.49 and 2.4).

EXAMPLE O

N-Benzyl-3-(4-methyl-1,2,3-triazol-1-yl)pyrrolidine and N-Benzyl-3-(5-methyl-1,2,3-triazol-1-yl)pyrrolidine A solution of 2 02 g (0 01 mole) of N-benzyl-3-azidopyrrolidine and 30 ml of 98% ethanol in a steel reaction vessel was cooled to −78 ° C. and into this was bubbled 17 g of the propyne. The sealed reaction vessel was then heated at 110° C. for 2.5 days. Removal of the solvent at reduced pressure resulted in 3 g of the crude product. Purification over silica gel (5% methanol ethyl acetate) afforded in the order of elution, 1.47 g of N-benzyl-3-(4-methyl-1,2,3-triazol-1-yl)pyrrolidine. $^1$H NMR (CDCl3) δ: 7.54 (s, 1H), 7.42–7.2 (m, 5H), 5.3–5.1 (m, 1H), 3.68 (s, 2H), 3.15–2.75 (m, 3H), 2.65–2.4 (m, 5H, singlet at 2.35) and 0.87 g of N-benzyl-3-(5-methyl-1,2,3-triazol-1-yl)pyrrolidine. $^1$H NMR (CDCl3) δ: 7.43 (s, 1H), 7.36–7.22 (m, 5H), 5.02–4.85 (m, 1H), 3.71 (s, 2H), 3.24–3.12 (s, 2H), 3.24–3.12 (m, 1H), 2.95–2.8 (m, 3H), 2.5–2.35 (m, 2H), 2.31 (s, 3H).

EXAMPLE P 3-(4-Methyl-1,2,3-triazol-1-yl)pyrrolidine hydrochloride

Prepared using the same procedure described in Example N by hydrogenating 1 g of N-benzyl-3-(4-methyl-1,2,3-triazol-1-yl)pyrrolidine. The yellow viscous liquid obtained after evaporation was crystallized from methanol ether to yield 0.82 g of white solid. $^1$H NMR (D2O) δ: 8.12 (S, 1H), 5.67–5.55 (m, 1H), 3.95 (d, 5.3 Hz, 2H), 3.67 (d, 6.26 Hz, 1H), 3.63 (d, 6.1 Hz, 1H). 2.85–2.45 (m, 2H), 2.42 (S, 3H).

EXAMPLE Q 3-(5-Methyl-1,2,3-triazol-1-yl)pyrrolidine hydrochloride

Hydrogenation of 0.87 g of the N-benzyl-3-(5-methyl-1,2,3-triazol-1-yl)pyrrolidine according to the procedure described for Example N afforded 0.708 g of the described product as a white salt after purification from methanol-ether. $^1$H NMR (D2O) δ: 7.63 (S, 1H), 5.7–5.5 (m, 1H), 4.25–3.6 (m, 4H), 2.87–2.37 (m, 5H, singlet at 2.51).

EXAMPLE R

N-Benzhydryl-3-azidoazetidine

To a solution of N-benzhydryl-3[(methyl sulphonyl)oxy]azetidine (5.04 16 mmol) in 180 ml of dimethylformamide and 30 ml of water was added 3.12 g (48 mmol) of sodium azide and 1.87 g (35 mmol) of ammonium chloride. The mixture was heated at 100° C. for 20 hr, cooled and diluted with water. This was extracted with methylene chloride and combined organic layers were washed with water, dried and evaporated to yield 6.49 g of the product (containing some DMF). $^1$H NMR (CDCl$_3$) δ: 7.40–7.09 (m, 10H), 4.35 (S, 1H), 4.02–3.83 (m, 1H), 3.46–3.12 (m, 2H), 3.05–2.91 (m, 2H).

EXAMPLE S

N-Benzhydryl-3-(1,2,3-triazol-1-yl) azetidine

To a solution of 1.05 g (3.98 mmol) of N-benzhydryl-3-azidoazetidine in 50 ml of acetone cooled to −78° C. in a steel reaction vessel was bubbled 36 g of acetylene. The sealed reaction vessel after warming up to room temperature was heated at 80° C. for 17 hr. The solution was then cooled to room temperature, filtered and evaporated to yield the crude product which after chromatography over silica gel (2.5% methanol chloroform) yielded 0.88 g (76%) of the desired product as a solid, m.p. 167°–168° C. $^1$H NMR (CDCl$_3$) δ: 7.88 (S, 1H), 7.73 (S, 1H), 7.55–7.07 (m, 10H), 5.35–5.1 (m, 1H), 4.53 (S, 1H), 3.76 (t, 2H), 3.5 (t, 2H).

EXAMPLE T 3-(1,2,3-Triazol-1-yl) azetidine hydrochloride

To a mixture of 0.88 g (3.03 mmol) of N-benzhydryl-3-(1,2,3-triazol-1-yl) azetidine in 25 ml of 98% ethanol was added 3 ml of 1N hydrochloric acid. To this solution was added 0.3 g of Pd/C (10%) and the mixture was then hydrogenated at 50 psi for 18 hr. After filtration of the Pd/C the solvent was removed under reduced pressure, and the residue was crystallized from methanol-ether to yield 0.25 g (51%) of the desired product m.p. 158°–160° C. $^1$H NMR (D$_2$O) δ 8.16 (S, 1H), 7.92 (S, 1H), 5.95–5.75 (m, 1H), 4.97–4.65 (m, 4H).

EXAMPLE U

N-Benzhydryl-3-(1,2,4-triazol-1-yl)azetidine

A suspension of N-benzhydryl-3-[(methylsulfonyl)oxy]azetidine (0.951 g, 3 mmol) and potassium-1,2,4-triazolide (0.69 g, 6.5 mmol) in 50 ml of dimethylformamide was heated at 85°–90° C. overnight. To this, water (200 ml) was added and extracted with ethyl acetate. The combined organic layers were washed with water, dried (Na$_2$SO$_4$) and evaporated to yield 0.9 g of the crude which upon purification over silica gel using ethyl acetate as solvent yielded 0.6 g of the desired product as a white solid. $^1$H NMR (CDCl$_3$) δ: 8.22 (s, 1H), 7.97 (s, 1H), 7.57–7.12 (m, 5H), 5.13–4.9 (m, 1H), 4.53 (s, 1H), 3.8–3.4 (m, 4H).

EXAMPLE V 3-(1,2,4-Triazol-1-yl) azetidine hydrochloride

To a mixture of N-benzhydryl-3-(1,2,4-triazol-1-yl) azetidine (0.6 g) in 20 ml of ethanol was added 2 ml of 1N hydrochloric acid followed by the addition of 0.6 g of Pd/C (10%). The mixture was hydrogenated at 50 psi for two days. After filtration and evaporation, the crude product was crystallized from methanol-ether to afford 0.235 g of white solid. $^1$H NMR (D$_2$O) δ: 9.14 (S, 1H), 8.57 (S, 1H), 5.97 (m, 1H), 4.8–4.5 (m, 4H).

EXAMPLE W

N-Benzyl-3-(1,2,4-triazol-1-yl]pyrrolidine

To a solution of 2.55 g (10 mmole) of N-benzyl-3-[(methyl-sulphonyl)oxy]pyrrolidine in 100 ml of dimethylformamide was added 3.21 g of potassium-1,2,4-triazolide and the reaction mixture was heated at 85°–90° C. overnight. The same work up and purification procedure described in Example U afforded 1.32 g (15% methanol-ethyl acetate as solvent) of the title product. $^1$H NMR (CDCl$_3$) δ: 8.3 (S, 1H), 7.93 (S, 1H), 7.6–7.1 (m, 5H), 5.2–4.6 (m, 1H), 3.67 (S, 2H), 3.23–2 (m, 6H).

EXAMPLE X 3-(1,2,4-Triazol-1-yl]pyrrolidine hydrochloride

The N-benzyl-3-(1,2,4-triazol-1-yl)pyrrolidine (1.3 g) was hydrogenated under similar conditions to Example V for 3 days to yield after crystallization from methanol-ether 1.08 g of white solid. $^1$H NMR (D$_2$O) δ: 9.24 (S, 1H), 8.51 (S, 1H), 5.68–5.5 (m, 1H), 3.97–3.5 (m, 4H), 2.86–2.4 (m, 2H).

EXAMPLE Y

N-benzyl-3-(4-ethoxy carbonyl-1,2,3-triazol-1-yl) pyrrolidine and N-benzyl-3-(5-ethoxy carbonyl-1,2,3-triazol-1-yl)pyrrolidine A mixture of N-benzyl-3-azido-pyrrolidine (5 g, 0.024 mmol) and ethylpropiolate (5 g, 0.051 mmol) in benzene (50 ml) heated under reflux for 48 hrs. Reaction solution was evaporated to dark brown oil, purified on silica gel column using ethylacetate, CHCl$_3$ and methanol to get N-benzyl-3-(5-ethoxycarbonyl-1,2,3-triazol-1-yl) pyrrolidine (1.5 g, 20.6%). $^1$H NMR (CDCl$_3$) δ: 1.37 (t, 3H), 2.42–2.58 (m, 2H), 2.71–3.01 (m, 3H), 3.20–3.32 (m, 1H), 3.73 (S, 2H), 4.35 (q, 2H), 5.72–5.88 (m, 1H), 7.2–7.4 (m, 5H), 8.12 (S, 1H). N-benzyl-3-(4-ethoxy carbonyl -1,2,3-triazol-1-yl)pyrrolidine (5 g, 68.7%). $^1$H NMR (CDCl$_3$) δ: 1.40 (t, 3H), 1.8–3.20 (m, 6H), 3.70 (S, 2H), 4.40 (q, 2H), 5.06–5.48 (m, 1H), 7.33 (S, 5H), 8.43 (S, 1H).

EXAMPLE Z

N-benzyl-3-(4-carboxy-1,2,3-triazol-1-yl)pyrrolidine hydrochloride

A solution of N-benzyl-3-(4-ethoxy carbonyl -1,2,3-triazol-1-yl)-pyrrolidine (5 g) in 5N HCl (200 ml) was heated under reflux at 110° C. for 16 hrs. The solution was evaporated under vacuum to dryness and the residue was crystallized from methanol/ether. Yield 3.6 g, 70.17%). $^1$H NMR (D$_2$O) δ: 2.11–2.72 (m, 2H), 3.30–3.90 (m, 4H), 4.27 (S, 2H), 5.18–5.48 (m, 1H), 7.30 (S, 5H), 8.30 (S, 1H).

EXAMPLE AA 3-(4-carboxy-1,2,3-triazol-1-yl)pyrrolidine hydrochloride

To a solution of N-benzyl-3-(4-carboxy-1,2,3-triazol-1-yl)pyrrolidine hydrochloride (1 g, 0.0033 mol) in methanol (50 ml) was added 10% Pd/C (100 mg) and conc. HCl (0.5 ml). The suspension was hydrogenated at r.t. and 50 psi pressure for 20 hrs. The Pd/C was removed by filtration and the solution was concentrated. The residue was recrystallized from methanol/ether to obtain white crystalline title compound. Yield: 650 mg (93.25%). $^1$H NMR (D$_2$O) δ: 2.51–3.56 (m, 2H), 3.62–3.75 (m, 2H), 3.92–4.00 (m, 2H), 5.52–5.67 (m, 1H), 8.67 (s, 1H).

EXAMPLE BB 3-(5-Ethoxy carbonyl-1,2,3-triazol-1-yl)pyrrolidine hydrochloride To a solution of N-benzyl-3-(5-ethoxy carbonyl -1,2,3-triazol-1-yl)pyrrolidine hydrochloride (2 g, 0.0061 mol) in methanol (100 ml) was added 10% Pd/C (200 mg) and concentrated HCl (1 ml). The suspension was hydrogenated at r.t. and 50 psi pressure for 20 hrs. The Pd/C was removed by filtration and the solution was concentrated. The residue was crystallized from methanol/ether to obtain crystalline white compound. Yield: 135 mg (93.29%). $^1$H NMR (D$_2$O) δ: 1.42 (t, 3H), 2.52–2.86 (m, 2H), 3.65–3.75 (m, 2H), 3.87–4.08 (m, 2H), 3.47 (q, 2H), 5.58–5.69 (m, 1H), 8.69 (s, 1H).

EXAMPLE CC

N-Benzyl-3-(4-phenyl-1,2,3-triazol-1-yl)pyrrolidine and N-Benzyl-3-(5-phenyl-1,2,3-triazol-1-yl)pyrrolidine A solution of N-benzyl-3-azido pyrrolidine (3 g, 0.0148 mol) and phenyl-acetylene (3 g, 0.0292 mol) in benzene (30 ml) was heated under reflux for 48 hrs. The reaction mixture was concentrated to oil from which the title compounds were isolated by column chromatography using silica gel and a mixture of CHCl$_3$, hexane, MeOH (4:4:1) as eluant. N-benzyl-3-(5-phenyl-1,2,3-triazol-1-yl)pyrrolidine was obtained as oil. Yield: 1 g (22.17%). $^1$H NMR (CDCl$_3$) δ: 2.32–2.51 (m, 2H), 2.88–3.13 (m, 2H), 3.80 (s, 2H), 5.00 (p, 1H), 7.20–7.53 (m, 10H), 7.67 (s, 1H). N-benzyl-3-(4-phenyl-1,2,3-triazol-1-yl)pyrrolidine, oil, yield 3.0 g. $^1$H NMR (CDCl$_3$) δ: 2.05–2.22 (m, 1H), 2.30–2.69 (m, 2H), 2.75–3.25 (m, 3H), 5.20–5.33 (m, 1H), 7.23–7.51 (m, 8H), 7.81–7.92 (m, 2H), 8.06 (s, 1H).

EXAMPLE DD 3-(4-phenyl-1,2,3-triazol-1-yl)pyrrolidine hydrochloride

A suspension of N-benzyl-3-(4-phenyl-1,2,3-triazol)-pyrrolidine (2.0 g), concentrated HCl (0.5 ml) and 10% Pd/C (200 mg) in methanol was hydrogenated following the procedure given in Example B. Yield: 1.32 g. $^1$H NMR (D$_2$O) δ: 2.35–2.72 (m, 2H), 3.57 (z, 2H), 3.84 (d, 2H), 5.35–5.45 (m, 1H), 7.35–7.65 (m, 5H), 8.23 (s, 1H).

EXAMPLE EE

N-Benzyl-3-(4-hydrazino carbonyl-1,2,3-triazol-1-yl)pyrrolidine

A suspension of N-benzyl-3-(4-ethoxy carbonyl -1,2,3-triazol-1-yl)pyrrolidine (5.6 g, 0.0186 mol) and NH$_2$NH$_2$ H$_2$O (2.36 g, 0.067 mol) in water (1.6 ml) was heated at 120° C. for 10 hrs. The reaction mixture was then cooled to r.t. and stirred with 15 ml of ether. The separated solid was filtered and washed with water. The white solid thus obtained was dried in the oven at 40° C. Yield: 3.8 g (71.29%), m.p. 122.6° C. $^1$H NMR (CDCl$_3$) δ: 1.96–2.14 (m, 1H) 2.36–3.15 (m, 5H), 3.7 (s, 2H), 4.05 (bs, 2H), 5.20–5.34 (m, 1H), 7.3 (s, 5H), 8.24 (s, 1H), 8.39 (s, 1H).

EXAMPLE FF

N-Benzyl-3-(4-azido carbonyl-1,2,3-triazol-1-yl)pyrrolidine

N-benzyl-3-(4-hydrazinocarbonyl-1,2,3-triazol -1-yl)pyrrolidine (3.6 g, 0.0125 mol) was dissolved in hot water (40 ml) and then cooled to 0° C. To the cooled suspension NaNO$_2$ (950 mg, 0.0137 mol in 3 ml of water) was added dropwise and then glacial AcOH (7 ml) was added to the reaction mixture was stirred at 0° C. for 15 min. Reaction mixture was then neutralized by the addition of saturated NaHCO$_3$. The separated white solid was filtered and washed with water, dried in vacuum oven. Yield: 3.73 g (100%), m.p. 160° C. $^1$H NMR (CDCl$_3$) δ: 1.95–2.15 (m, 1H), 2.37–2.83 (m, 3H), 2.94–3.22 (m, 2H), 3.70 (d, 2H), 5.75–5.87 (m, 1H), 7.30 (s, 5H), 8.47 (s, 1H).

EXAMPLE GG

N-Benzyl-3-(4-t-butoxycarbonyl-amino-1,2,3-triazol-1-yl)pyrrolidine

A solution of N-benzyl-3-(4-azido carbonyl -1,2,3-triazol-1-yl)pyrrolidine (1 g, 2.91 mmol) in t-butanol (15 ml) was refluxed for 15 hrs. The reaction mixture was evaporated to dryness. Pure title compound was obtained as an oil by purification on silica gel column using CHCl$_3$/MeOH as eluant. Yield: 700 mg (60.86%). $^1$H NM (CDCl$_3$) δ: 1.52 (s, 9H), 2.41–2.65 (m, 2H), 2.77–3.11 (m, 4H), 3.70 (s, 2H), 3.56–3.73 (m, 1H), 7.30 (s, 5H), 7.94 (S, 1H).

EXAMPLE HH

N-Benzyl-3-(4-amino-1,2,3-triazol-1-yl)pyrrolidine dihydrochloride

A solution of N-benzyl-3-(4-t-butoxy carbonyl amino-1,2,3-triazol-1-yl)pyrrolidine (100 mg, 0.291 mmol) and concentrated HCl (0.5 ml) in methanol (5 ml) was stirred at r.t for 30 min. The solution was evaporated to dryness and the residue was crystallized from methanol/ether to obtain the title compound as a solid. Yield: 90 mg (98.9%) $^1$H NMR (D$_2$O) δ: 2.52–3.0 (m, 2H), 3.55–4.70 (m, 4H), 4.60 (s, 2H), 5.50–5.76 (m, 1H), 7.60 (s, 1H), 8.03 (s, 1H).

EXAMPLE II 3-(4-amino-1,2,3-triazol-1-yl)pyrrolidinedihydrochloride

To a solution of N-benzyl-(4-t-butoxy carbonyl amino-1,2,3-triazol-1-yl)-pyrrolidine-dihydrochloride (700 mg) in methanol 5% Pd/C (200 mg) was added. The suspension was hydrogenated at r.t. and 50 psi pressure over 30 hrs. The Pd/C was removed by filtration and the solution was concentrated. The residue was crystallized from methanol/ether to a white solid. Yield: 440 mg (95.8%). $^1$H MNR (TFA) δ: 2.70–3.16 (m, 2H), 3.8–4.50 (m, 4H), 5.60–6.15 (m, 1H), 8.12 (s, 1H). The title compound was also obtained by hydrogenation of N-benzyl-(4-amino -1,2,3-triazol-1-yl)pyrrolidine hydrochloride in a yield of 92% following the procedure as given above.

EXAMPLE JJ

N-Benzyl-3-(1,2,3,4-tetrazol-1-yl)pyrrolidine and N-Benzyl-3-(1,2,3,4-tetrazol-2-yl)pyrrolidine A suspension of N-benzyl-3-[(methylsulphonyl)oxy]-pyrrolidine (2.2 g, 9.37 mmol) and sodium 1,2,3,4-tetrazolide (1.8 g, 19.6 mmol) in 50 ml of dimethylformamide was heated at 85–90° C. overnight. The reaction mixture was worked up the same as described in Example U. The crude product was purified over silica gel using hexane, ether and ethyl acetate as eluant to afford in order of elution 0.413 g of N-benzyl-3-(1,2,3,4-tetrazol-2-yl) pyrrolidine as an oil. $^1$H NMR (CDCl$_3$) δ: 8.51 (s, 1H), 7.37–7.17 (m, 5H), 5.51–5.35 (m, 1H), 3.8–3.65 (q, 2H), 3.3–2.4 (m, 6H); and .26 g of N-benzyl-3-(1,2,3,4-tetrazol-1-yl)pyrrolidine as an oil. $^1$H NMR (CDCl$_3$) 6 : 8.88 (s, 1H), 7.4–7.2 (m, 5H), 5.35–5.2 (m, 1H), 3.83–3.6 (q, 2H), 3.2–2.3 (m, 5H), 2.15–2.00 (m, 1H).

EXAMPLE KK 3-(1,2,3,4-tetrazol-2-yl)pyrrolidine hydrochloride

The N-benzyl-3-(1,2,3,4-tetrazol-2-yl) pyrrolidine (0.4 g) was hydrogenated under similar conditions as described for Example B to yield 280 mg of title product as hydrochloride salt after crystallization with methanol ether. $^1$H NMR (D20) δ : 8.84 (s, 1H), 6.05–5.86 (m, 1H), 4.18–3.87 (m, 2H), 3.8–3.6 (m, 2H), 2.94–2.55 (m, 2H).

EXAMPLE LL 3-(1,2,3,4-tetrazol-1-yl)pyrrolidine hydrochloride

The N-benzyl-3-(1,2,3,4-tetrazol-1-yl)pyrrolidine (0.214 g) was hydrogenated under similar conditions as described for Example B to yield 80 mg of the title product as hydrochloride salt. $^1$H NMR (D$_2$O) δ: 9.31 (s, 1H), 5.32–5.63 (m, 1H), 4.02–3.85 (m, 2H), 3.8–3.56 (m, 2H), 2.88–2.44 (m, 4H).

EXAMPLE MM 1-(tert-Butoxy carbonyl)-3-(1,2,4-triazol)piperidine

Potassium 1,2,4-triazolide (19.5 g) was added to a solution of 1-(tert-butoxy carbonyl) -3-[(methylsulphonyl) oxy]piperidine (15.00 g) in DMF (175 ml). The reaction mixture was heated at 80° C. for 16 hrs, then cooled, diluted with water and extracted with ethyl acetate. The organic extract was dried over Na$_2$SO$_4$ and concentrated. The residue was chromatographed over silica gel, gave 3.6 g of title product as pale yellow oil. $^1$H NMR (CDCl$_3$) δ: 8.28 (s, 1H), 7.94 (s, 1H), 4.00–4.40 (m, 2H), 3.85 (m, 1H), 3.45 (m, 1H), 3.05 (m, 1H), 2.15 (m, 2H), 1.55–1.88 (m, 2H), 1.44 (s, 9H).

EXAMPLE NN 3-(1,2,4-Triazole)piperidine hydrochloride

Concentrated HCL (1.6 ml) was added to a solution of 1-(tert-butoxy carbonyl)-3-(1,2,4-triazole)piperidine (1.00 g) in methanol (8 ml). The reaction mixture was stirred at room temperature under nitrogen for 2 hrs, and then concentrated to dryness. The residue was crystallized from methanol-ether. The pale yellow solid was filtered and dried. Yield: 300 mg; $^1$H NMR (D$_2$O) δ: 9.6 (S, 1H), 8.7 (s, 1H), 5.1 (m, 1H), 3.1–3.85 (m, 5H), 1.85–2.45 (m, 4H).

EXAMPLE OO 1-(tert-Butoxy-carbonyl)-3-azidopiperidine

Sodium azide (6.96 g, 0.107 mol) and ammonium chloride (2.13 g, 0.0399 mol) were added to a solution of 1-(tert-butoxy carbonyl)3-[(methylsulphonyl)oxy]piperidine (10 g, 0.0358 mol) in DMF (75 ml) and water (12.5 ml). The mixture was heated overnight at 125° C. under stirring, cooled and diluted with water and extracted with chloroform. The organic layer was washed with water, dried over Na$_2$SO$_4$ and concentrated to give 4.6 g of thin reddish brown oil. $^1$H NMR (CDCl$_3$) δ: 2.80–4.30 (m, 5H), 1.60–2.20 (m, 4H), 1.50 (s, 9H).

EXAMPLE PP 1-(tert-Butoxycarbonyl)-3-(1,2,3-triazol-1-piperidine

Acetylene (10 g) was condensed in a −70° C. cooled solution of 3-azido-1-(tert-butoxy carbonyl)piperidine (4.57 g, 0.0177 mol) in acetone (100 ml) in a steel reaction vessel. The steel reaction vessel was heated at 120° C. for 28 hrs, cooled, unreacted acetylene was removed and the remaining solvent was concentrated under vacuo. The residue was chromatographed over silica gel using ethylacetate:hexane (2:1) as eluant to give 3.23 g of white solid pure product. $^1$H NMR (CDCl$_3$) δ: 7.77 (s, 1H), 7.70 (s, 1H), 2.80–4.86 (m, 5H), 2.06–2.53 (m, 2H), 1.62–2.00 (m, 2H), 1.50 (s, 9H).

EXAMPLE QQ 3-(1,2,3-Triazol-1-yl) piperidine hydrochloride

Concentrated HCL (7.0 ml) was added to a solution of 1-(tert-butoxy carbonyl)-3-(1,2,3-triazol-1-yl)piperidine (3.23 g) in methanol (35 ml) and stirred at room temperature for 3 hrs. The reaction mixture was concentrated to dryness and the residue was crystallized from methanol-ether to give 2.0 g of pure product as hydrochloride. $^1$H NMR (CO$_3$OD) δ: 8.44 (s, 1H), 8.15 (s, 1H), 5.18 (m, 1H), 3.75 (m, 2H), 3.10–3.45 (m, 2H), 2.38 (m, 2H), 2.08 (m, 2H).

The structure of the intermediates and of compounds of the invention were established by the modes of synthesis and by extensive high field nuclear magnetic resonance spectral techniques.

The compounds of the first aspect of the present invention showed antibacterial activity when tested by the standard broth microdilution method as described in the NCCLS document M7-A2. Approved standard: Method for Dilution Antimicrobial Susceptibility Tests for Bacteria that Grow Aerobically - Second Edition, 1990. The test organisms were obtained from ATCC and clinical laboratories. The 96-well microtitre plates containing 100 ml of serially diluted test compounds in Mueller Hinton Broth (MHB) (conc. range 64–0.004 μg/ml) were inoculated with 100 ml of bacterial suspension in MHB so that an inoculum size of $5 \times 10^5$ cfu/ml was achieved. The plates were shaken gently and incubated at 35° C. for 18 hr after which the minimum inhibitory concentrations (MIC, μg/ml) at which no visible microbial growth occurred were recorded.

The compounds of the invention display antibacterial activity when tested by the broth microdilution method as described in the NCCLS publications M7-A, M11-A and M17-P of the year 1985. For aerobic microorganisms, a cation supplemented Mueller Hinton Broth (BBL) was used whereas the Anaerobe Broth MIC (Difco) was used for anaerobic microorganisms. An agar Dilution method was employed for certain aerobic microorganisms using Mueller Hinton II Agar (BBL) and a Cathra multipoint inoculating device which delivered $10^4$ cfu/spot of the inoculum on the agar surface. MICs were read after 16–18 hours and 48 hours of incubation in case of microbes growing aerobically and anaerobically respectively.

By use of the above method, the following minimum inhibitory concentration values (MICs in μg/ml) were obtained: Table 1, against microbes growing aerobically; Table 2, against microbes growing anaerobically; Table 3, against methicillin resistant Staphylococcus aureus and quinoline resistant-methicillin resistant Staphylococcus aureus.

TABLE 1

In vitro Antimicrobial Activity Against Aerobes MIC (μg/ml)

| Example No. | Staphylococcus aureus S-127 | Escherichia coli S-63 | Enterobacter cloacae S-11 | Klebsiella pneumoniae S-80 | Pseudomonas aeruginosa S-67 |
|---|---|---|---|---|---|
| 2 | ≦.06 | .5 | 4 | 2 | 4 |
| 4 | ≦.06 | 1 | 2 | 2 | 8 |
| 5 | ≦.03 | .12 | .50 | .25 | 4 |
| 6 | ≦.03 | .12 | .5 | .25 | 4 |
| 7 | .008 | .03 | .25 | .25 | 2 |
| 12 | .008 | .03 | .25 | .25 | 2 |
| 13 | .008 | .03 | .25 | .25 | 2 |
| 14 | ≦.015 | .25 | 2 | 1 | 8 |
| 15 | .015 | .25 | 2 | 1 | 8 |
| 16 | .015 | .25 | 2 | 1 | 8 |
| 17 | 1 | .5 | 4 | 1 | 8 |
| 18 | .5 | .25 | 1 | .5 | 8 |
| 19 | .5 | 1 | 4 | 1 | 16 |
| 20 | — | .25 | 4 | 4 | 4 |
| Sparfloxacin | .06 | ≦.015 | .12 | .03 | 1 |
| Ciprofloxacin | .25 | ≦.015 | .015 | .03 | .25 |

TABLE 2

In vitro Antimicrobial Activity Against Anaerobes MIC (μg/ml)

| Microbes | Example No. 1 | 12 | 14 | SPAR | CIP |
|---|---|---|---|---|---|
| Bacteroides fagilis AN-2 | 1 | 1 | >64 | 2 | 16 |
| Fusobacterium mortiferum AN-13 | 06 | .06 | 2 | .50 | 16 |
| Propionobacterium acne AN-17 | ≦.03 | .06 | .06 | 1 | .50 |
| Peptostreptococcus asaccharolyticus AN-16 | .06 | .06 | .12 | 4 | 4 |
| Streptococcus intermedius AN-19 | .06 | .12 | .06 | .50 | 1 |

SPAR = Sparfloxacin, CIP = Ciprofloxacin

TABLE 3

In vitro Antimicrobial Activity Against Methicillin Resistant S. aureus (MRSAs) and Quinoline Resistant MRSAs (QRMRSAs)

| Example No. | MRSA (6 C.I.) MIC range (μg/ml) | QRMRSA (8 C.I.) |
|---|---|---|
| 11 | .004–.008 | .50–2 |
| 12 | .004–.008 | .50–2 |
| 14 | .008–.03 | 1–8 |
| 15 | .008–.015 | 1–16 |
| Sparfloxacin | .03–.12 | 4–16 |
| Ciprofloxacin | .25–.50 | 16–>64 |
| Tosufloxacin | .015–.03 | 2–16 |

C.I. = Clinical Isolates

In another test procedure, the compounds of the present invention showed antibacterial activity when tested by the standard broth microdilution method as described in the NCCLS document M7-A2. Approved standard: Method for Dilution Antimicrobial Susceptibility Tests for Bacteria that Grow Aerobically - Second Edition, 1990. The test organisms were obtained from ATCC and clinical laboratories. The 96-well microtitre plates containing 100 ml of serially diluted test compounds in Mueller Hinton Broth (MHB) (conc. range 64–0.03 μg/ml) were inoculated with 100 ml of bacterial suspension in MHB so that an inoculum size of $5 \times 10^5$ cfu/ml was achieved. The plates were shaken gently and incubated at 35° C. for 18 hr after which the minimum inhibitory concentrations (MIC, μg/ml) at which no visible microbial growth occurred were recorded.

The abbreviations for the test organisms used in Table 1 below are as follows:

Ec. (S-63) Escherichia coli
Ecl. (S-130) Enterobacter cloacae
Pa. (S-67) Pseudomonas aeruginosa
Kp. (S-80) Klebsiella pneumoniae
Pr. (S-121) Providencia rettgeri
Sa. (S-127) Staphylococcus aureus
Sa (S-127M Staphylococcus aureus, quinolone resistant ANTIMICROBIAL ACTIVITY (MIC, μg/ml)

Microbroth Dilution (MHB); Inoculum, $5 \times 10^5$ cfu/ml; Incubation 35 C/18 hr

| Example No. | Ec. S-63 | Ecl. S-130 | Pa. S-67 | Kp. S-80 | Pr. S-121 | Sa. S-127 | Sa. 127M |
|---|---|---|---|---|---|---|---|
| 2 | .5 | 4 | 4 | 2 | 1 | ≦.06 | ND |
| 5 | .12 | .5 | 4 | .25 | 2 | .125 | .5 |
| 7 | 1 | 2 | 32 | 2 | 2 | 8 | 64 |
| 8 | 1 | 2 | 8 | 2 | 1 | ≦.06 | ND |
| 9 | .12 | .5 | 4 | .12 | .25 | .06 | ND |
| 10 | .06 | .12 | 1 | .12 | .12 | .015 | .06 |
| 11 | .03 | .12 | 2 | .25 | .25 | ≦.004 | ≦.015 |
| 12 | .06 | .5 | 2 | .25 | .25 | ≦.015 | ≦.06 |
| 13 | .03 | .125 | 1 | .06 | .125 | ≦.004 | ≦.015 |
| 14 | .25 | 2 | 8 | 1 | 1 | .015 | .06 |
| 15 | .25 | 1 | 4 | 1 | 1 | .03 | .06 |
| 17 | .5 | 2 | 8 | 1 | 1 | 1 | ND |
| 18 | .25 | 1 | 8 | .5 | 1 | .5 | 1 |
| 19 | 1 | 4 | 16 | 1 | 2 | .5 | 2 |
| 20 | .5 | 4 | 4 | 4 | ND | .25 | .5 |
| 21 | .06 | .25 | 2 | .25 | .12 | .015 | .015 |
| 22 | .25 | 1 | 4 | .5 | 2 | .125 | .5 |

-continued

| Example No. | Ec. S-63 | Ecl. S-130 | Pa. S-67 | Kp. S-80 | Pr. S-121 | Sa. S-127 | Sa. 127M |
|---|---|---|---|---|---|---|---|
| 23 | — | — | — | — | — | .03 | — |
| 24 | .25 | .25 | 4 | .5 | .25 | ≦.015 | .12 |
| 25 | .12 | .25 | 4 | .5 | .5 | ≦.015 | ≦.015 |
| 26 | .12 | .25 | 4 | .5 | .5 | ≦.015 | ≦.015 |
| 27 | .06 | .25 | 2 | .25 | .25 | ≦.015 | .03 |
| 28 | .25 | 2 | 8 | 1 | 1 | .03 | .06 |
| 29 | .25 | 1 | 4 | .5 | 2 | .125 | .25 |
| 30 | .12 | ND | ND | ND | ND | ≦.015 | ND |
| 31 | .06 | .25 | 2 | .25 | .5 | ≦.03 | .03 |
| 32 | .12 | .25 | 4 | .5 | .25 | .03 | .06 |
| 34 | .12 | .5 | 2 | .25 | .5 | ≦.015 | ≦.015 |
| 35 | .12 | .5 | 4 | .25 | .12 | ≦.03 | ≦.03 |
| 36 | .12 | 1 | 8 | 1 | 2 | ≦.015 | ≦.015 |
| 37 | .5 | .5 | 8 | .5 | .5 | .5 | 1 |
| 38 | .25 | .5 | 4 | .25 | .25 | ≦.015 | .03 |
| 40 | .5 | 2 | 8 | 1 | 1 | .06 | .25 |
| 41 | .25 | 1 | 8 | 1 | 1 | .12 | .5 |
| 42 | .25 | 1 | 8 | 1 | 1 | .03 | .12 |
| 43 | 1 | 1 | 8 | 1 | .5 | 1 | .5 |
| 44 | .12 | — | — | — | — | .03 | — |
| 45 | .5 | 1 | 4 | 1 | 1 | .25 | 1 |
| 46 | 16 | 32 | >32 | 32 | 32 | 8 | 8 |
| 47 | .5 | .25 | .8 | 1 | 1 | 25 | — |
| 48 | .25 | — | — | — | — | — | 1 |
| 49 | .25 | 1 | 32 | 1 | .015 | .015 | .015 |
| 50 | .25 | 16 | >32 | .5 | .015 | .015 | .015 |
| 51 | 1 | 4 | 16 | 4 | .015 | .015 | .015 |
| 52 | .5 | .50 | 8 | .5 | .12 | .25 | .25 |
| 53 | 1 | 2 | 16 | 1 | .06 | .25 | .25 |
| 54 | .06 | — | 2 | .12 | .12 | ≦.03 | ≦.03 |
| 55 | .06 | — | 2 | .25 | .12 | .06 | — |
| 56 | .12 | 1 | 8 | 2 | 2 | >.03 | <.03 |
| 57 | .03 | .5 | 4 | .5 | .25 | ≦.015 | ≦.015 |
| 58 | .06 | 1 | 4 | .5 | .5 | ≦.015 | ≦.015 |
| 59 | .25 | 2 | 8 | 1 | 2 | ≦.015 | .06 |
| 60 | .25 | 2 | 16 | 1 | .5 | ≦.015 | ≦.015 |
| 61 | 1 | 16 | >32 | 16 | 16 | .012 | .5 |
| 63 | .25 | 1 | 16 | .5 | 4 | .5 | .12 |
| 65 | .5 | 2 | 16 | 1 | 2 | .5 | .12 |
| 66 | .12 | 1 | 4 | 1 | 2 | <.03 | <.03 |
| 68 | .5 | 1 | 16 | 2 | 2 | .5 | 4 |
| 69 | .5 | 2 | 32 | 1 | 2 | .12 | .5 |
| 70 | .06 | .5 | 8 | .25 | 1 | ≦.004 | ≦.004 |
| 71 | 0.06 | 1.0 | 16 | 1.0 | 1.0 | 0.004 | ≦0.008 |
| CPLX | ≦.008 | .03 | .25 | .015 | .015 | .25 | 8 |
| NFLX | .06 | .12 | 1 | .12 | 1 | 1 | 16 |
| NFLX-Ch | .06 | .25 | 1 | .25 | .12 | 2 | 16 |

ND = Not Done

For Anaerobic microorganisms, an agar Dilution method was employed using Mueller Hinton II Agar (BBL) and a Cathra multipoint inoculating device which delivered $10^4$ cfu/spot of the inoculum on the agar surface. MICs were read after 16–18 hours of incubation of microbes growing aerobically.

By use of the above method, the following minimum inhibitory concentration values (MICs in μg/ml) were obtained: reported in Table 2.

TABLE 2

In Vitro Antimicrobial Activity Against Anaerobes MIC (μg/ml)

| Microbes | Example No. | | | SPAR | CIP |
|---|---|---|---|---|---|
| | 11 | 12 | 14 | | |
| Bacteroides fagilis AN-2 | 1 | 1 | >64 | 2 | 16 |
| Fusobacterium mortiferum AN-13 | .06 | .06 | 2 | .50 | 16 |
| Propionobacterium acne AN-17 | <=.03 | .06 | .06 | 1 | .50 |
| Peptostreptococcus asaccharolyticus AN-16 | .06 | .06 | .12 | 4 | 4 |
| Streptococcus intermedium AN-19 | .06 | .12 | .06 | .50 | 1 |

TABLE 2-continued

In Vitro Antimicrobial Activity Against Anaerobes MIC (μg/ml)

| Microbes | Example No. | | | SPAR | CIP |
|---|---|---|---|---|---|
| | 11 | 12 | 14 | | |

SPAR = Sparfloxacin, CIP = Ciprofloxacin

While the invention has been particularly shown and described in reference to preferred embodiments, it will be understood by those skilled in the art that changes in form and details may be made without departing from the spirit and scope of the invention. For example, the compounds disclosed and described could be used in compositions to disinfect surfaces in environments where food is prepared.

What is claimed is:

1. A 7-substituted-6-fluoro-1,4-dihydro-4-oxo-quinoline-3-carboxylic acid compound of the formula:

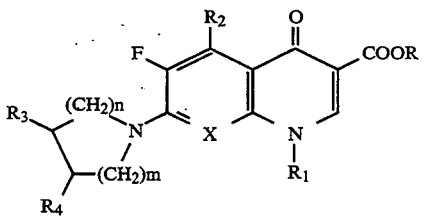

I wherein R is hydrogen or $C_1$–$C_4$ alkyl group; $R_1$ is (i) a $C_3$–$C_6$ cycloalkyl group which may be substituted with one or two halogen atoms, (ii) a phenyl group which may be substituted with one or two halogen atoms, or (iii) a $C_1$–$C_4$ alkyl group which may be substituted with one or two halogen atoms; $R_2$ is hydrogen, a halogen atom, a $C_1$–$C_4$ alkyl group, a hydroxy group or an amino group;

$R_3$ is hydrogen, a hydroxy or an amino group;

$R_4$ is a 1,2,3-triazol-1-yl group, a 1,2,4-triazol-1-yl group, a 1,2,3,4-tetrazol-1-yl group or a 1,2,3,4-tetrazol-2-yl group, each of which may have 1 to 2 substituents selected from the group consisting of $C_1$–$C_4$ alkyl, COOH, $CH_2NH_2$, amino and phenyl groups; and X is CH, C—F or C—$OCH_3$; m is 1 or 2; n is 0, 1 or 2;

or a pharmaceutically acceptable salt of any compound, recited above.

2. A compound of formula I as set forth in claim 1, wherein said $C_3$–$C_6$ cycloalkyl group is selected from the group consisting of cyclopropyl, cyclobutyl, cyclopentyl and cyclohexyl.

3. A compound of formula I as set forth in claim 1, wherein R, $R_1$ and $R_2$ are the same or different and are selected from the group consisting of methyl, ethyl, propyl, isopropyl, butyl, isobutyl and t-butyl.

4. A compound of formula I as set forth in claim 1, wherein said one or two halogen atoms are the same or different and are selected from the group consisting of chlorine, bromine and fluorine.

5. A compound of formula I as set forth in claim 1 wherein one carbon atom is an asymmetric carbon atom, and said compound is an optically active D isomer.

6. A compound of formula I as set forth in claim 1 wherein one carbon atom is an asymmetric carbon atom, and said compound is an optically active L isomer.

7. A composition comprising an optically active racemic mixture of D isomer and L isomer, comprising a compound of formula I as set forth in claim 1 wherein one carbon atom is an asymmetric carbon atom.

8. A compound of formula I as set forth in claim 1 wherein two carbon atoms are asymmetric carbon atoms, and said compound is a stereoisomer having cis form.

9. A compound of formula I as set forth in claim 1 wherein two carbon atoms are asymmetric carbon atoms, and said compound is a stereoisomer having trans form.

10. A composition comprising a racemic mixture of cis and trans forms of a compound of formula I as set forth in claim 1 wherein two carbon atoms are asymmetric carbon atoms.

11. A 7-substituted-6-fluoro-1,4-dihydro-4-oxo-quinoline-3-carboxylic acid compound of the formula

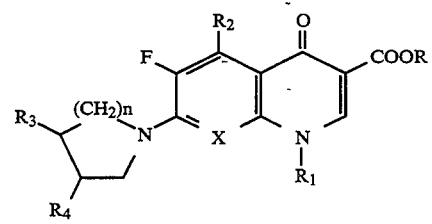

wherein
R is hydrogen or a $C_1$–$C_4$ alkyl group;
$R_1$ is a $C_1$–$C_4$ alkyl group which is unsubstituted or substituted with one or two halogen atoms, a $C_3$–$C_6$ alicyclic hydrocarbon group which is unsubstituted or substituted with one or two halogen atoms, or a phenyl group which is unsubstituted or substituted with one or two halogen atoms, amino group or methoxy group;
$R^2$ is hydrogen, a halogen, a $C_1$–$C_4$ alkyl group, $NR^5R^6$, OH, $OC_1$–$C_4$ alkyl or

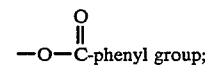

$R^3$ is hydrogen, $C_1$–$C_4$ alkyl, $C_3$–$C_6$ cycloalkyl, halo, COOR, $CH_2COOR$, $NR^5R^6$, $CH_2NR^5R^6$, OH, $OC_1$–$C_4$ alkyl, $COCH_3$ or phenyl;
n=0, 1, or 2;
wherein $R^4$ is

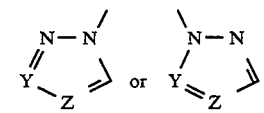

Y and Z are N or CH, provided that at least one of Y and Z is N, so that $R_4$ forms a 1,2,3-triazol-1-yl, a 1,2,4-triazol-1-yl, a 1,2,3,4-tetrazol-1-yl or a 1,2,3,4-tetrazol-2-yl ring, optionally substituted by halogen, $C_1$–$C_4$ alkyl, $C_3$–$C_6$ cycloalkane, $CH_2COOR$, $CSC_1$–$C_4$ alkyl, $NR^5$ $R^6$, $CH_2NR^5R^6$ or phenyl; and $R^5$ and $R^6$ are hydrogen, a $C_1$–$C_4$ alkyl group, or a $C_3$–$C_6$ cycloalkyl group; X is C—F, CH, C—$CH_3$, C—$CF_3$ or C—$OCH_3$;

or a pharmaceutically acceptable salt thereof.

12. A compound according to claim 1, wherein $R_1$ is phenyl, 4-fluorophenyl, 2,4-difluorophenyl, 2,4-dimethoxyphenyl or 4-aminophenyl.

13. A compound according to claim 11, wherein $R_1$ is a $C_1$–$C_4$ alkyl group, a $C_3$–$C_6$ alicyclic hydrocarbon group, or a phenyl group, any of said groups being optionally substituted by chloro, fluoro, bromo, methoxy or amino.

14. A compound according to claim 11, wherein n=1 and the compound has an asymmetric carbon atom on the pyrrolidine ring, and the compound is the R isomer, or the S isomer.

15. A compound according to claim 11, wherein n=1 and the compound has two asymmetric carbon atoms on the pyrrolidine ring, and the compound is a stereoisomer structure of the cis or trans configuration.

16. A 7-substituted-6-fluoro-1,4-dihydro-4-oxoquinoline-3-carboxylic acid compound of the formula:

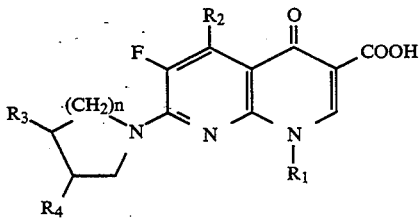

wherein

R₁ is a $C_3$-$C_6$ cycloalkyl group or a phenyl group which may be substituted by one or two halogen atoms;

R₂ is hydrogen, a halogen atom, a $C_1$-$C_4$ alkyl group, a hydroxy group or an amino group;

R₃ is hydrogen, hydroxy or amino;

R₄ is a 1,2,3-triazol-1-yl group, a 1,2,4-triazol-1-yl group, a 1,2,3,4-tetrazol-1-yl group or a 1,2,3,4-tetrazol-2-yl group, each of which may have 1 to 2 substituents selected from the group consisting of $C_1$-$C_4$ alkyl, COOH, $CO_2NH_2$, amino and phenyl groups;

X is CH, C—F or C—$OCH_3$;

n is 0, 1 or 2;

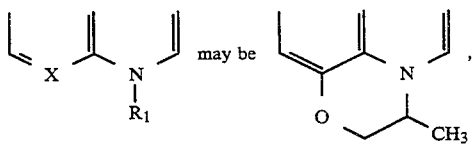

or a pharmaceutically acceptable salt thereof.

17. 1-cyclopropyl-6-fluoro-7-[(3-1,2,3,-triazol-1-yl)pyrrolidin-1-yl[-1,4-dihydro -4-oxo-quinoline-3-carboxylic acid according to claim 11.

18. 1-cyclopropyl-6,8-difluoro-7-[3-(1,2,3-triazol-1-yl)pyrrolidin -1-yl]-1,4-dihydro-4-oxo-quinoline-3-carboxylic acid according to claim 11.

19. 5-Amino-1-cyclopropyl-6,8-difluoro-7-[3-(1,2,3-triazol-1-yl) -pyrrolidin-1-yl]-1,4-dihydro-4-oxo-quinoline-3-carboxylic acid according to claim 11.

20. 5-Amino-1-cyclopropyl-6,8-difluoro-7-[3S-(1,2,3-triazol-1-yl) -pyrrolidin-1-yl]-1,4-dihydro-4-oxo-quinoline-3-carboxylic acid according to claim 11.

21. 5-Amino-1-cyclopropyl-6,8-difluoro-7-[3R-(1,2,3-triazol-1-yl) pyrrolidin-1-yl]-1,4-dihydro-4-oxo-quinoline-3-carboxylic acid according to claim 11.

22. 5-Amino-1-(2,4-difluorophenyl)-6,8-difluoro-7-[3-(1,2,3-triazol -1-yl)pyrrolidin-1-yl]-1,4-dihydro-4-oxoquinoline-3-carboxylic acid according to claim 11.

23. 5-Amino-1-(2,4-difluorophenyl)-6,8-difluoro-7-[3S-(1,2,3-triazol-1-yl)pyrrolidin -1-yl]-1,4-dihydro-4-oxo-quinoline-3-carboxylic acid according to claim 11.

24. 5-Amino-1-(2,4-difluorophenyl)-6,8-difluoro-7-[3R-(1,2,3-triazol-1-yl)pyrrolidin -1-yl]-1,4-dihydro-4-oxo-quinoline-3-carboxylic acid according to claim 11.

25. 7-[cis 3-Amino-4-(1,2,3-triazol-1-yl)pyrrolidin-1-yl]-1-cyclopropyl-6,8-difluoro-1,4-dihydro-4-oxo-quinoline-3-carboxylic acid according to claim 11.

26. 5-Amino-7-[cis 3-amino-4-(1,2,3-triazol-1-yl)pyrrolidin-1-yl]-1-cyclopropyl-6,8-difluoro-1,4-dihydro-4-oxo-quinoline-3-carboxylic acid according to claim 11.

27. 5-Amino-7-[cis 3-amino-4-(1,2,3-triazol-1-yl)pyrrolidin -1-yl]-1-(2,4-difluorophenyl)-6,8-difluoro-1,4-dihydro-4-oxo-quinoline -3-carboxylic acid according to claim 11.

28. 5-Amino-7-[trans 3-hydroxy-4-(1,2,3-triazol-1-yl)-pyrrolidin-1-yl]-1-cyclopropyl-6,8-difluoro-1,4-dihydro-4-oxo-quinoline-3-carboxylic acid according to claim 11.

29. 6,8-Difluoro-1-(4-fluorophenyl)-7-[3-(1,2,3-triazol-1-yl) -pyrrolidin-1-yl]-1,4-dihydro-4-oxo-quinoline-3-carboxylic acid according to claim 11.

30. A pharmaceutical composition suitable for treating bacterial infections comprising an antibacterial amount of a compound of claim 11 and a pharmaceutically acceptable carrier.

31. A method for treating a bacterial infection in humans which comprises administering to a human having a bacterial infection an antibacterially effective amount of a compound of claim 11.

32. A method for treating a bacterial infection in humans which comprises administering to a human having a bacterial infection an antibacterially effective amount of a compound of claim 16.

33. A pharmaceutical composition suitable for treating bacterial infections comprising an antibacterial amount of a compound of claim 17 and a pharmaceutically acceptable carrier.

34. A method for treating a bacterial infection in humans which comprises administering to a human having a bacterial infection an antibacterially effective amount of the compound of claim 17.

35. 1-Cyclopropyl-6,8-difluoro-5-methyl-7-[3-(4-methyl-1,2,3-triazol-1-yl)pyrrolidine-1-yl]-1,4-dihydro-4-oxoquinoline-3-carboxylic acid, according to claim 11.

36. 1-Cyclopropyl-6,8-difluoro-5-methyl-7-[3-(1,2,4-triazol-1-yl)pyrrolidine -1-yl]-1,4-dihydro-4-oxoquinoline-3-carboxylic acid, according to claim 11.

37. 1-Cyclopropyl-6,8-difluoro-5-methyl-7-[3-(1,2,3-triazol-1-yl)pyrrolidine -1-yl]-1,4-dihydro-4-oxoquinoline-3-carboxylic acid, according to claim 11.

38. 1-Cyclopropyl-6,8-difluoro-7-[3-(4,5-dimethyl-1,2,3-triazol-1-yl)pyrrolidine -1-yl]-1,4-dihydro-4-oxoquinoline-3-carboxylic acid, according to claim 11.

39. 1-Cyclopropyl-6-fluoro-7-[3S-(1,2,3-triazol-1-yl)pyrrolidine-1-yl] -8-methoxy-1,4-dihydro-4-oxoquinoline-3-carboxylic acid, according to claim 11.

40. 1-Cyclopropyl-6-fluoro-7-[3-(1,2,3-triazol-1-yl)pyrrolidine-1-yl]-8-methoxy-1,4-dihydro-4-oxoquinoline-3-carboxylic acid, according to claim 11.

41. 1-Cyclopropyl-6-fluoro-7-[3-(4-methyl-1,2,3-triazol-1-yl)pyrrolidine-1-yl]-8-methoxy-1,4-dihydro-4-oxoquinoline-3-carboxylic acid, according to claim 11.

42. 1-Cyclopropyl-6-fluoro-7-[3-(1,2,3-triazol-1-yl)pyrrolidine-1-yl]-8-methoxy-1,4-dihydro-4-oxoquinoline-3-carboxylic acid, according to claim 11.

43. 1-Cyclopropyl-6,8-difluoro-7-[3-(1,2,3-triazol-1-yl)piperidine-1-yl]-1,4-dihydro-4-oxoquinoline-3-carboxylic acid, according to claim 11.

44. A 7-substituted-6-fluoro-1,4-dihydro-4-oxoquinoline-3-carboxylic acid compound of the formula:

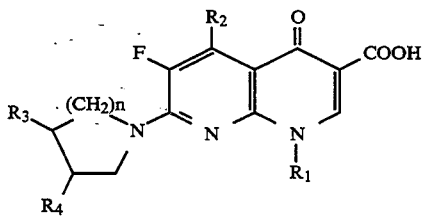

wherein

R₁ is (1) a $C_3$-$C_6$ cycloalkyl group which may be substituted by one or two halogen atoms, methoxy groups or amino groups, or (2) a phenyl group which may be substituted by one or two halogen atoms, methoxy groups or amino groups;

R₂ is hydrogen, a halogen tom, a $C_1$-$C_4$ alkyl group, a hydroxy group or an amino group;

R₃ is hydrogen, hydroxy or amino;

R₄ is a 1,2,3-triazol-1-yl group, a 1,2,4-triazol-1-yl group, a 1,2,3,4-tetrazol-1-yl or a 1,2,3,4-tetrazol-2-yl group, each of which may have 1 to 2 substituents selected from the group consisting of $C_1$-$C_4$ alkyl, COOH, $CH_2NH_2$, amino and phenyl groups; and X is CH, C—F or C—$OCH_3$;

n is 0, 1 or 2;

or a pharmaceutically acceptable salt thereof.

45. A compound according to claim 44, wherein R₁ is phenyl, 4-fluorophenyl, 2,4-difluorophenyl, 2,4-dimethoxyphenyl or 4-aminophenyl.

46. A compound according to claim 44, wherein R₁ is optionally substituted by chloro, fluoro, bromo, methoxy or amino.

47. A compound according to claim 44, wherein n = 1 and the compound has an asymmetric carbon atom on the pyrrolidine ring, and the compound is the R isomer, or the S isomer.

48. A compound according to claim 44, wherein n = 1 and the compound has two asymmetric carbon atoms on the pyrrolidine ring, and the compound is a stereoisomer structure of the cis trans configuration.

49. A pharmaceutical composition suitable for treating bacterial infections comprising an antibacterial amount of a compound of claim 44 and a pharmaceutically acceptable carrier.

50. A method for treating a bacterial infection in humans which comprises administering to a human having a bacterial infection in antibacterially effective amount of a compound of claim 44.

51. A 7-(Substituted triazolyl pyrrolidin-1-yl) 4-oxo-quinoline-3-carboxylic acid derivative of formula I:

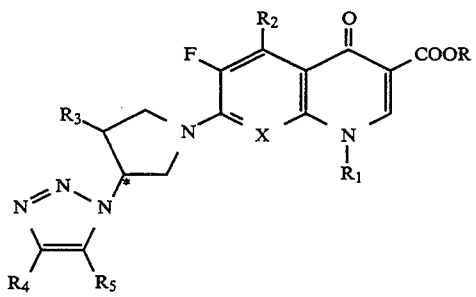

wherein;

R is hydrogen or a $C_1$-$C_4$ alkyl group;

R₁ is a $C_1$-$C_4$ alkyl group which is unsubstituted or substituted with one or two halogen atoms, or a $C_3$-$C_6$ alicyclic group which is unsubstituted or substituted with one or two halogen atoms, or a $C_6$ aromatic hydrocarbon group which is unsubstituted or substituted with one or two halogen atoms, amino group or methoxy group;

R₂ is hydrogen, halogen, $C_1$-$C_4$ alkyl group or NHR₆;

R₃ is hydrogen, OR₆, fluorine, $CH_3$ or NHR₆;

R₄ and R₅ are independently hydrogen, —COOH, $CH_2OH$, $CH_2NHR_6$, NHR₆ or $CH_3$;

R₆ is hydrogen, $C_1$-$C_4$ alkyl group or cycloalkyl group; and

X is C—F, CH, C—$CH_3$, C—$CF_3$ or C—$OCH_3$, or pharmaceutically acceptable salts.

52. The derivative of claim 51 wherein R₁ is selected from the group consisting of phenyl, 4-fluorophenyl, 2,4-difluorophenyl, 2,4-dimethoxyphenyl and 4-aminophenyl.

53. The derivative of claim 51 wherein R₁ is a $C_1$-$C_4$ alkyl group, a $C_3$-$C_6$ alicyclic hydrocarbon group, or a phenyl group, any of said groups being optionally substituted by chlorine, fluorine, bromine, methoxy or amino.

54. The derivative of claim 51, wherein said derivative has an asymmetric carbon atom on the pyrrolidine ring, and the derivative is the D isomer, or the L isomer.

55. The derivative of claim 51, wherein said derivative has two asymmetric carbon atoms on the pyrrolidine ring, and the derivative is a stereoisomer structure of the cis or trans configuration.

56. A 7-(substituted triazolyl pyrrolidin-1 yl)4-oxo-quinoline-3-carboxylic acid derivative of the formula I

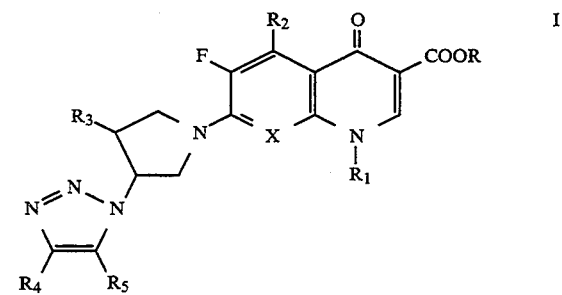

wherein,

R is hydrogen;

R₁ is ethyl, cyclopropyl, 4-fluorophenyl or 2,4-difluorophenyl;

R₂ is hydrogen, F or $NH_2$;

R₃ is hydrogen, $NH_2$ or OH;

R₄ and R₅ are hydrogen; and

X is CF, CH, C—$CH_3$, C—$CF_3$ or C—$OCH_3$, or a pharmaceutically acceptable salt thereof.

57. 1-cyclopropyl-6-fluoro-7-(3-1,2,3-triazol-1-yl)pyrrolidin -1-yl]-1,4-dihydro-4-oxo-quinoline-3-carboxylic acid according to claim 51.

58. A pharmaceutical composition suitable for treating bacterial infections comprising an antibacterial amount of a compound of claim 51 and a pharmaceutically acceptable carrier.

59. A method for treating a bacterial infection in humans which comprises administering to a human having a bacterial infection an antibacterially effective amount of a compound of claim 51.

60. A derivative as recited in claim 51, wherein at least one of said one or two halogen atom sin chlorine, bromine, or fluorine, and said derivative includes the D isomer, or the L isomer, and when $R_3$ is not hydrogen, including the cis isomer or the trans isomer.

61. A composition comprising a mixture of the R isomer and the S isomer of a compound as recited in claim 14.

62. A composition comprising cis isomer and trans isomer of a compound as recited in claim 15.

63. A composition comprising the R isomer and the isomer of a compound as recited in claim 47.

64. A composition comprising the cis isomer and the trans isomer of a compound as recited in claim 48.

65. A composition comprising the D isomer and the L isomer of a compound as recited in claim 54.

66. A composition comprising the cis isomer and the trans isomer of a derivative as recited in claim 55.

67. A composition comprising the D isomer and the L isomer of a derivative as recited in claim 60.

68. A compound a recited in claim 40, wherein said compound is an S isomer with positive rotation.

* * * * *